US008642086B2

(12) United States Patent
Coady et al.

(10) Patent No.: US 8,642,086 B2
(45) Date of Patent: Feb. 4, 2014

(54) ANTIMICROBIAL COMPOSITIONS, METHODS OF PREPARATION THEREOF, AND USES THEREOF

(75) Inventors: Daniel Joseph Coady, San Jose, CA (US); Kazuki Fukushima, San Jose, CA (US); James Lupton Hedrick, Pleasanton, CA (US); Yi Yan Yang, Singapore (SG)

(73) Assignees: International Business Machines Corporation, Armonk, NY (US); Agency for Science, Technology and Research, Singapore (SG)

( * ) Notice: Subject to any disclaimer, the term of this patent is extended or adjusted under 35 U.S.C. 154(b) by 40 days.

(21) Appl. No.: 13/077,005

(22) Filed: Mar. 31, 2011

(65) Prior Publication Data

US 2012/0251607 A1 Oct. 4, 2012

(51) Int. Cl.
*A61K 9/00* (2006.01)
*A61K 31/765* (2006.01)
(52) U.S. Cl.
USPC ....................................... 424/486; 424/78.17
(58) Field of Classification Search
None
See application file for complete search history.

(56) References Cited

U.S. PATENT DOCUMENTS

| | | | |
|---|---|---|---|
| 4,981,696 | A | 1/1991 | Loomis |
| 6,251,967 | B1 | 6/2001 | Perichaud |
| 6,361,787 | B1 | 3/2002 | Shaheen |
| 6,413,539 | B1 | 7/2002 | Shalaby |
| 6,541,033 | B1 | 4/2003 | Shah |
| 6,762,162 | B1 | 7/2004 | Valpey, III |
| 6,800,278 | B1 | 10/2004 | Perrault |
| 7,776,359 | B1 | 8/2010 | Hennink |
| 2007/0185008 | A1 | 8/2007 | Hennink |
| 2008/0118546 | A1 | 5/2008 | Thatcher |
| 2008/0131512 | A1 | 6/2008 | Hennink |
| 2008/0226722 | A1 | 9/2008 | Van Tomme |
| 2008/0260795 | A1* | 10/2008 | Baughman et al. ............ 424/423 |
| 2009/0281249 | A1 | 11/2009 | Thatcher |
| 2010/0003327 | A1 | 1/2010 | Thatcher |
| 2010/0166863 | A1 | 7/2010 | Shen |
| 2010/0196494 | A1 | 8/2010 | Van Beek |
| 2011/0150977 | A1* | 6/2011 | Hedrick et al. ............... 424/450 |
| 2011/0151566 | A1 | 6/2011 | Hedrick et al. |
| 2012/0283391 | A1* | 11/2012 | Venkatraman et al. ....... 525/411 |

FOREIGN PATENT DOCUMENTS

| | | |
|---|---|---|
| EP | 0481042 B1 | 10/1991 |
| EP | 2204397 A2 | 7/2007 |
| WO | 9960852 A1 | 12/1999 |
| WO | 2008018796 A2 | 2/2008 |

OTHER PUBLICATIONS

Fujiwara, et al., "Novel Thermo-Responsive Formation of a Hydrogel by Stereo-Complexation between PLLA-PEG-PLLA and PDLA-PEG-PDLA Block Copolymers," Macromol. Biosci. 2001, 1, 204-208.
Hiemstra, et al., "Stereocomplex Mediated Gelation of PEG-(PLA)2 and PEG-(PLA)8 Block Copolymers," Macromol. Symp. 2005, 224, 119-131.
Jiang, et al., "Water-Soluble Thermoresponsive Polylactides," Macromolecules 2008, 41, 318-324, published on Web Apr. 2, 2005.
Li, et al., "Synthesis, Characterization, and Stereocomplex-Induced Gelation of Block Copolymers Prepared by Ring-Opening Polymerization of L(D)-Lactide in the Presence of Poly(ethylene glycol)," Macromolecules 2003, 36, 8008-8014.
Liu, et al., "Biodegradable poly(ethylene glycol)—peptide hydrogels with well-defined structure and properties for cell delivery," Biomaterials 30 (2009) 1453-1461.
Liu, et al., "Synthetic hydrogels for controlled stem cell differentiation," Soft Matter, 2010, 6, 67-81.
Lutolf, et al., "Cell- Responsive Synthetic Hydrogels," Adv. Mater. 2003, 15, No. 11, 888-891.
Lutz, et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules 2006, 39, 893-896, Published on Web Dec. 21, 2005.
Malkoch, et al., "Structurally Diverse Dendritic Libraries: A Highly Efficient Functionalization Approach Using Click Chemistry," Macromolecules 2005, 38, 3663-3678, Published on Web Apr. 2, 2005.
Mespouille, et al., Soft Matter, 2009, 5, 4878-4892.
Metters, et al., "Network Formation and Degradation Behavior of Hydrogels Formed by Michael-Type Addition Reactions," Biomacromolecules 2005, 6, 290-301, Published on Web Nov. 13, 2004.
Mukose, et al., "Hydrogel Formation between Enantiomeric B-A-B-Type Block Copolymers of Polylactides (PLLA or PDLA: A) and Polyoxyethylene (PEG: B); PEG-PLLA-PEG and PEG-PDLA-PEG," Macromol. Biosci. 2004, 4, 361-367.
Shu, et al., "In situ crosslinkable hyaluronan hydrogels for tissue engineering," Biomaterials 25 (2004) 1339-1348.
USPTO, Non-Final Office Action mailed Jun. 20, 2013, U.S. Appl. No. 13/333,930, Coady et al., filed Dec. 21, 2011.

* cited by examiner

*Primary Examiner* — Susan Tran
*Assistant Examiner* — Jessica Worsham
(74) *Attorney, Agent, or Firm* — Michael R. Roberts

(57) ABSTRACT

A composition of matter comprises a cationic polymer comprising a polycarbonate chain fragment, the polycarbonate chain fragment comprising a repeat unit comprising a side chain moiety containing a quaternary amine group; and a non-charged polymer comprising a polyester chain segment and a poly(alkylene oxide) chain segment; wherein i) the cationic polymer and the non-charged polymer are amphiphilic and biocompatible, ii) the cationic polymer and the non-charged polymer form a mixed complex by non-covalent interactions in water, and iii) the mixed complex is a more effective antimicrobial agent against at least a Gram-negative microbe compared to the cationic polymer and the non-charged polymer alone when tested using otherwise identical conditions.

44 Claims, 20 Drawing Sheets

Ex. 49                    20.0μm

Ex. 50                    20.0μm

Ex. 51                    20.0μm

Ex. 45C                   20.0μm

SEM Images of E. Coli in PEG1L10 Hydrogel (Magnification 15k, 35k)

SEM Images of E. Coli in Cationic Hydrogel
(Magnification 15k, 25k, 20k)

ANTIMICROBIAL COMPOSITIONS, METHODS OF PREPARATION THEREOF, AND USES THEREOF

BACKGROUND

The present invention relates to antimicrobial compositions, methods of preparation thereof, and uses thereof, and more specifically to antimicrobial mixed complexes formed by non-covalent interactions of a cationic polymer and a non-charged polymer.

Aqueous hydrogels have gained attention in the field of medicine, particularly in wound healing and regenerative medicine. Of particular interest are hydrogels formed by materials that have a lower critical solution temperature (LCST) in water. As one example, heating an aqueous solution of an LCST material to a temperature at or above the critical temperature can produce a high viscosity thermoreversible gel, which when cooled below the critical temperature, restores the relatively low viscosity solution phase.

Hydrogels can also be formed by mixtures of materials. Fujiwara et al., "Novel Thermo-Responsive Formation of a Hydrogel by Stereo-Complexation between PLLA-PEG-PLLA and PDLA-PEG-PDLA Block Copolymers," Macromolecular Bioscience (2001), vol. 1, pgs. 204-208, have prepared thermally responsive gels from mixtures of poly(L-lactide)-b-poly(ethylene oxide)-b-poly(L-lactide) triblock copolymers with poly(D-lactide)-b-poly(ethylene oxide)-b-poly(D-lactide) triblock copolymers. In aqueous solution the soluble polymer mixtures transform into gels at temperatures in the proximity of body temperature (about 37° C.). These gels are limited with respect to their application owing to their poor mechanical properties and limited functionality.

Providing materials having expanded functionality and utility for antimicrobial and/or gene binding applications remains an ongoing need.

SUMMARY

Accordingly, a first composition of matter is disclosed, comprising:
a cationic polymer comprising a polycarbonate chain fragment, the polycarbonate chain fragment comprising a repeat unit comprising a side chain moiety containing a quaternary amine group; and
a non-charged polymer comprising a polyester chain segment and a poly(alkylene oxide) chain segment;
wherein i) the cationic polymer and the non-charged polymer are amphiphilic and biocompatible, ii) the cationic polymer and the non-charged polymer form a mixed complex by non-covalent interactions in water, and iii) the mixed complex is a more effective antimicrobial agent against at least a Gram-negative microbe compared to the cationic polymer and the non-charged polymer alone when tested using otherwise identical conditions.

A method is disclosed, comprising contacting a microbe with the above-described first composition, thereby killing the microbe.

A loaded complex is disclosed comprising i) the above-described first composition and ii) a drug and/or a gene.

Another method is disclosed, comprising forming an aqueous mixture of the above-described first composition, the aqueous mixture an effective antimicrobial agent against at least a Gram-negative microbe.

Another method is disclosed, comprising:
forming an aqueous first mixture containing a cationic polymer comprising a polycarbonate chain fragment, the polycarbonate chain fragment comprising a repeat unit comprising a side chain quaternary amine group;
forming an aqueous second mixture containing a non-charged polymer comprising a polyester chain segment and a poly(alkylene oxide) chain segment; and
combining the first mixture and the second mixture, thereby forming a third mixture comprising a mixed complex of the cationic polymer and the non-charged polymer bound by non-covalent interactions;
wherein i) the cationic polymer and the non-charged polymer are amphiphilic and biocompatible, and ii) the mixed complex is a more effective antimicrobial agent against at least a Gram-negative microbe compared to the cationic polymer alone and the non-charged polymer alone when tested under otherwise identical conditions.

A second composition of matter is disclosed, comprising:
a cationic triblock copolymer having an ABA block structure, wherein a block A is a hydrophobic peripheral block, and a block B is a hydrophilic cationic core block; and
a non-charged triblock copolymer having a FEF block structure, wherein block E is a hydrophilic non-charged core block, and block F is a peripheral hydrophobic block;
wherein i) the non-charged triblock copolymer and the cationic triblock copolymer are amphiphilic and biocompatible, ii) the non-charged triblock copolymer and the cationic triblock copolymer form a mixed complex by non-covalent interactions in water, and iii) the mixed complex is a more effective antimicrobial agent against at least a Gram-negative microbe compared to the cationic triblock copolymer alone and the non-charged triblock copolymer alone when tested using otherwise identical conditions.

Another loaded complex is disclosed, comprising i) the above-described second composition and ii) a drug and/or a gene.

Another method is disclosed, comprising contacting a microbe with the above-described second composition, thereby killing the microbe.

Another method is disclosed, comprising forming an aqueous mixture of the above-described second composition, the aqueous mixture an effective antimicrobial agent against at least a Gram-negative microbe.

Another method is disclosed, comprising:
forming an aqueous first mixture of a cationic triblock copolymer having an ABA block structure, wherein a block A is a peripheral hydrophobic block, and a block B is a hydrophilic cationic core block;
forming an aqueous second mixture of a non-charged triblock copolymer having a FEF block structure, wherein a block E is a hydrophilic core block, and a block F is a peripheral hydrophobic block; and
combining the first mixture and the second mixture, thereby forming a third mixture comprising a mixed complex of the cationic triblock copolymer and the non-charged triblock copolymer bound by non-covalent interactions;
wherein i) the non-charged triblock copolymer and the cationic triblock copolymer are amphiphilic and biocompatible, and ii) the mixed complex is a more effective antimicrobial agent against at least a Gram-negative microbe compared to the cationic triblock copolymer alone and the non-charged triblock copolymer alone when tested under otherwise identical conditions.

Also disclosed is an article comprising a medical device in contact with the above-described second composition.

The above-described and other features and advantages of the present invention will be appreciated and understood by those skilled in the art from the following detailed description, drawings, and appended claims.

DETAILED DESCRIPTION

Figure 1A:
FIG. 1A is a photograph of a solution of Example 28C containing equal amounts of the two cationic triblock copolymers, PCC3 (Example 23) and PCC4 (Example 24), before heating.

Compositions having enhanced antimicrobial activity are disclosed. The compositions comprise a mixed complex of a cationic polymer and a non-charged polymer. The cationic polymer and the non-charged polymer are bound by non-covalent interactions in the mixed complex. The cationic and non-charged polymers are biocompatible, amphiphilic materials that can be stored and packaged separately before combining them to form the antimicrobial composition. A "biocompatible" material is defined herein as a material capable of performing with an appropriate host response in a specific application. The mixed complex can be in the form of a powder or an aqueous mixture. The cationic polymer and/or the non-charged polymer preferably comprise at least one stereospecific repeat unit. The cationic polymer is enzymatically biodegradable. The non-charged polymer can be substantially or wholly enzymatically biodegradable. In water, the mixed complexes can have the form of a nanoparticulate micelle solution and/or a supramolecular hydrogel. The mixed complexes have strong antimicrobial activity and gene binding capability, making them potentially useful for many medical applications.

The toxicity of the mixed complexes toward at least a Gram-negative microbe is super-additive, exceeding that of the cationic polymer alone and the non-charged polymer alone when tested using otherwise identical conditions. Surprisingly, the mixed complexes can be toxic to at least a Gram negative microbe (e.g., *Escherichia coli*) when the cationic polymer and the non-charged polymer individually are not effective antimicrobial agents against the Gram-negative microbe. Herein, a material is "not effective" as an antimicrobial agent if the material performs about the same as the phosphate buffered saline (PBS) control solution, and/or has a minimum inhibitory concentration (MIC) greater than 25,000 mg/L. In an embodiment, the mixed complexes are toxic to a Gram-negative microbe and a Gram-positive microbe selected from the group consisting of bacteria, fungi, yeasts, and combinations thereof. A method comprises contacting a microbe with the composition in the form of a dry powder or an aqueous mixture, thereby killing the microbe.

Also disclosed is a process for treating a surface, comprising i) forming a mixed complex by non-covalent interactions of a cationic polymer and a non-charged polymer; and ii) and contacting a surface with the mixed complex, wherein the mixed complex is an effective antimicrobial agent against a Gram-negative microbe.

The mixed complex can also serve as a carrier for genes and drugs in the form of a loaded complex, thereby providing a therapeutic agent capable of two or more independent biological functions (e.g., antimicrobial function, gene and/or drug delivery function, cell recognition function, artificial skin function, etc.).

Another general process for treating a cell and/or a surface comprises i) forming a loaded complex comprising a cationic polymer, a non-charged polymer, and a biologically active cargo material bound by non-covalent interactions; and ii) contacting the cell and/or the surface with the loaded complex. In an embodiment, the cargo material is a gene, the loaded complex enters a cell, the gene is released by the loaded complex within the cell, and the gene is expressed by the cell. In another embodiment, the cargo material is a drug.

The cationic polymer and the non-charged polymer can independently be a random copolymer or a block copolymer. Even more specifically, the cationic polymer comprises a polycarbonate chain fragment that includes a repeat unit comprising a side chain quaternary amine group that forms a mixed complex by non-covalent interactions in water with the non-charged polymer. In another embodiment, the cationic polymer comprises a first stereospecific repeat unit and the non-charged polymer comprises a second stereospecific repeat unit.

The cationic polymer and the non-charged polymer can independently be a linear polymer or a branched polymer, such as a star polymer. A star polymer can comprise three or more independent polymer arms emanating from a central core.

The cationic polymer has a net positive charge resulting from cationic groups that are covalently bound to the cationic polymer, or a mixture of cationic groups (e.g., quaternary amine) and anionic groups (e.g., carboxylate) that are covalently bound to the cationic polymer. Preferably, the cationic polymer contains no anionic groups that are covalently bound to the cationic polymer before contact with a cell. The cationic groups can independently contain a nitrogen bonded to four carbons (quaternary amine), a sulfur bonded to three carbons (sulfonium group), or a phosphorous bonded to four carbons (phosphonium group). The cationic polymer can comprise a mixture of the foregoing cationic functional groups. In an embodiment, the cationic functional group is a side chain moiety.

In a preferred embodiment, the cationic polymer comprises a repeat unit comprising a cationic side chain moiety comprising a quaternary amine group. Preferably, the covalently bound cationic group has a negative charged counterion that is not covalently bound to the cationic polymer before contacting a cell. Non-limiting exemplary negative charged counterions include chloride, bromide, iodide, acetate, benzoate, benzene sulfonate, and toluene sulfonate. The cationic polymer can comprise a mixture of negative charged counterions.

The non-charged polymer (including cationic block copolymer and cationic triblock copolymer mentioned below) preferably contains no cationic groups and no anionic groups before contact with a cell.

Block Copolymers.

In a more specific embodiment, the cationic polymer and the non-charged polymer are block copolymers capable of forming a mixed complex in aqueous solution by non-covalent interactions. The cationic block copolymer comprises a hydrophilic cationic block and a hydrophobic block. The hydrophobic block of the cationic block copolymer can comprise a first stereospecific repeat unit. The non-charged block copolymer comprises a non-charged hydrophilic block and a hydrophobic block. The hydrophobic block of the non-charged block copolymer can comprise a second stereospecific repeat unit. The hydrophilic block and the hydrophobic block of the cationic block copolymer are enzymatically biodegradable. The hydrophobic block of the non-charged block copolymer is also enzymatically biodegradable. The hydrophilic block of the non-charged block copolymer is biocompatible, and in a preferred embodiment, is also enzymatically biodegradable. In an embodiment, the hydrophilic block of the cationic block copolymer comprises a repeat unit having a cationic side chain moiety comprising a quaternary amine group.

The cationic block copolymer and the non-charged block copolymer can independently comprise one or more hydrophobic blocks and one or more hydrophilic blocks. Preferably, at least one hydrophilic block of the cationic block copolymer comprises a side chain moiety comprising a quaternary amine. The one or more hydrophilic blocks of the non-charged block copolymer preferably have no repeat units comprising a charged group prior to contact with a cell.

In another embodiment, at least one hydrophobic block of the cationic block copolymer comprises a first stereospecific repeat unit. In another embodiment, at least one hydrophobic block of the non-charged block copolymer comprises a second stereospecific repeat unit. The first and the second stereospecific repeat units can be the same or different chemical structures. A stereospecific repeat unit comprises an asymmetric tetravalent carbon and does not have a superposable mirror image. The stereospecific repeat unit can comprise one or more asymmetric tetravalent carbons, each independently having an R or S stereoconfiguration. In an embodiment, at least one asymmetric tetravalent carbon of the stereospecific repeat unit is a backbone carbon of the hydrophobic block.

In an even more specific embodiment, the cationic block copolymer and the non-charged block copolymer are triblock copolymers comprising two peripheral hydrophobic blocks and a core hydrophilic block. The triblock copolymers are amphiphilic biocompatible materials. The cationic triblock copolymer is biodegradable. The non-charged triblock copolymer can be substantially or wholly biodegradable. The triblock copolymers can comprise one or more stereospecific repeat units. In an embodiment, the core hydrophilic block of the cationic triblock copolymer comprises a repeat unit comprising a side chain moiety comprising a quaternary amine. The core hydrophilic block of the non-charged triblock copolymer has substantially no repeat units comprising a charged group. In an embodiment, at least one of the peripheral hydrophobic blocks of the cationic triblock copolymer comprises a first stereospecific repeat unit. In another embodiment, at least one of the peripheral hydrophobic blocks of the non-charged triblock copolymer comprises a second stereospecific repeat unit. In another embodiment, both of the hydrophobic blocks of the cationic triblock copolymer comprise the first stereospecific repeat unit, and both of the hydrophobic blocks of the non-charged triblock copolymer comprise the second stereospecific repeat unit.

The hydrophilic and hydrophobic blocks of the cationic and non-charged triblock copolymers can be prepared by sequential organocatalyzed ring opening polymerization (ROP) of cyclic carbonyl monomers. The ring-opening method allows precise control of the molecular weight of the polymer, achieves a low polydispersity and high stereospecificity, and is compatible with a variety of functional groups. Examples of cyclic carbonyl monomers include cyclic carbonate monomers and cyclic esters (lactones), including lactides and glycolide, that ring-open to form polymers comprising carbonate and ester repeat units, respectively.

The cationic triblock copolymer and the non-charged triblock copolymer form a mixed complex in aqueous solution. The mixed complex can be in the form of a micelle and/or a hydrogel (also referred to as "gel"). The micelle solution and/or the hydrogel can be a transparent (i.e., clear), translucent, or opaque mixture. The micelles can be amorphous particles. Alternatively, the micelles and/or the hydrogels can have a geometric particle morphology such as a sphere, rod, fiber, plate, cube, or another geometric shape. The micelles and/or the hydrogels can comprise particles having a combination of geometric shapes.

The aqueous solution of the mixed complex can be heat thickening, meaning the aqueous mixture has a higher viscosity at 32° C. to 40° C. compared to the viscosity at ambient temperature (18° C. to 28° C.).

The cationic triblock copolymer and the non-charged triblock copolymer can form a supermolecular hydrogel in water. The hydrogel can comprise one or more morphologies of the mixed complex. No restriction is placed on the viscosity of the hydrogel or the micelle solution, providing the hydrogel and/or the micelle solution are suitable for use as an antimicrobial agent. The hydrogel can have the viscosity of a liquid, a viscous liquid, a cream, or a rigid gel. The hydrogel can be thermoreversible or non-thermoreversible. The hydrogel can be shear thinning, meaning the viscosity of the hydrogel can decrease by subjecting the hydrogel to a shearing force (e.g., rapid stirring), and increase again by removing the shearing force. The hydrogel can form at ambient temperature or a higher temperature after mixing together an aqueous mixture of the cationic triblock copolymer and an aqueous mixture of the non-charged triblock copolymer. In an embodiment, an aqueous mixture containing the cationic triblock copolymer and the non-charged triblock copolymer forms a micelle solution at ambient temperature, which transforms to a hydrogel when heated to a temperature of 32° C. to 40° C. (e.g., human body temperature of 37° C.). In another embodiment, the hydrogel is shear thinning In another embodiment, the aqueous mixture of the cationic triblock copolymer and the non-charged triblock copolymer is a hydrogel at ambient temperature.

Herein, a "stereospecific repeat unit" i) has a non-superposable mirror image and ii) comprises one or more asymmetric tetravalent carbons. Each asymmetric tetravalent carbon is assigned an R or S symmetry based on Cahn-Ingold-Prelog (CIP) symmetry rules. For example, if the hydrophobic block contains a stereospecific first repeat unit having one asymmetric tetravalent carbon, then the first repeat unit can be present in the hydrophobic block substantially as the R stereoisomer or substantially as the S stereoisomer, meaning the stereoisomer can be present in a stereoisomeric purity of 90% to 100%, 94% or more, or more particularly 98% to 100%. In another example, if the stereospecific repeat unit has two asymmetric tetravalent carbons, the stereospecific repeat unit can be present in the hydrophobic block substantially as the R,R stereoisomer, substantially as the R,S stereoisomer, substantially as the S,S stereoisomer, or substantially as the S,R stereoisomer.

A "stereospecific cyclic carbonyl monomer" i) has a non-superposable mirror image and ii) comprises one or more asymmetric tetravalent carbons. The stereospecific cyclic carbonyl monomer has a stereoisomeric purity of 90% or more, and more particularly 98% or more. In an embodiment, at least one of the asymmetric tetravalent carbons of the stereospecific cyclic carbonyl monomer is a ring carbon that becomes a polymer backbone carbon in a ring opening polymerization.

"Restricted metals" herein include ionic and nonionic forms of beryllium, magnesium, calcium, strontium, barium, radium, aluminum, gallium, indium, thallium, germanium, tin, lead, arsenic, antimony, bismuth, tellurium, polonium, and metals of Groups 3 to 12 of the Periodic Table. Metals of Groups 3 to 12 of the Periodic Table include scandium, titanium, vanadium, chromium, manganese, iron, cobalt, nickel, copper, zinc, yttrium, zirconium, niobium, molybdenum, technetium, ruthenium, rhodium, palladium, silver, cadmium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, actinium, thorium, protactinium, uranium, neptunium, plutonium, americium, curium, berkelium, californium, einsteinium, fermium, mendelevium, nobelium, lawrencium, rutherfordium, dubnium, seaborgium, bohrium, hassium, meitnerium, darmstadtium, roentgenium, and copernicium. Each one of the foregoing restricted metals can have a concentration in the antimicrobial composition of 0 parts to 100 ppm (parts per million), 0 parts to 100 ppb (parts per billion), or 0 parts to 100 ppt (parts per trillion). Preferably, each one of the foregoing restricted metals has a concentration of 0 parts in the antimicrobial composition (i.e., the concentration is below detection limits). In an embodiment, the chemical formula of the cationic first material and the chemical formula of the non-charged second material of the disclosed compositions contain none of the above restricted metals.

No restriction is placed on the concentration of boron, silicon, or any individual alkali metal in the antimicrobial composition as long as the antimicrobial properties of the mixed complex are not adversely affected.

The term "biodegradable" is defined by the American Society for Testing and Materials as a degradation caused by biological activity, especially by enzymatic action, leading to a significant change in the chemical structure of the material. For purposes herein, a material is "biodegradable" if it undergoes 60% biodegradation within 180 days in accordance with ASTM D6400. Herein, a material is "enzymatically biodegradable" if the material can be degraded (e.g., depolymerized) by a reaction catalyzed by an enzyme.

The term "carrier" in the following description refers to the mixed complex comprising the cationic triblock copolymer and the non-charged triblock copolymer. The carrier can have the form of a micelle solution or a hydrogel. The carrier is a biologically active material and can be use alone (e.g., by applying the carrier as a liquid antimicrobial agent to a wound surface and allowing the aqueous mixture to form a hydrogel at about human body temperature, or about 37° C.). A loaded complex comprising the carrier and a biologically active cargo material can have additional biological function and/or an enhanced biological function. The cargo can be any biologically active substance that forms a loaded complex with the carrier, providing the loaded complex has desirable and useful properties. For example, the loaded complex can enter a cell by endocytosis, and the loaded complex can release the biologically active substance at a desired stage within the cell or tissues (in the case where the active substance is the cell). Biologically active substances include cells, biomolecules (e.g., DNA, genes, peptides, proteins, enzymes, lipids, phospholipids, and nucleotides), natural or synthetic organic compounds (e.g., drugs, dyes, synthetic polymers, oligomers, and amino acids), inorganic materials (e.g., metals and metal oxides), radioactive variants of the foregoing, and combinations of the foregoing.

"Biologically active" means the referenced material can alter the chemical structure and/or activity of a cell in a desirable manner, or can selectively alter the chemical structure and/or activity of a cell type relative to another cell type in a desirable manner. As an example, one desirable change in a chemical structure can be the incorporation of a gene into the DNA of the cell. A desirable change in activity can be the expression of the transfected gene. Another change in cell activity can be the induced production of a desired hormone or enzyme. Alternatively, a desirable change in activity can be the selective death of one cell type over another cell type. No limitation is placed on the relative change in cellular activity caused by the biologically active substance, providing the change is desirable and useful. Moreover, no limitation is placed on the cargo, providing the cargo induces a useful cellular response when released from the loaded complex.
Cationic Triblock Copolymer.

Using "A" to represent a hydrophobic block and "B" to represent a hydrophilic block comprising a cationic repeat unit, the cationic triblock copolymer can have an ABA triblock structure, comprising a hydrophilic cationic core block B, and two peripheral hydrophobic Blocks A. In this example, the two peripheral blocks A are substantially identical to one another. In an embodiment, hydrophobic blocks A comprise a stereospecific repeat unit. In another embodiment, hydrophilic block B comprises a polycarbonate chain segment, and the polycarbonate chain segment comprises a repeat unit having a side chain moiety comprising a quaternary amine group.

Alternatively, the cationic triblock copolymer can have a BAB triblock structure, wherein the two peripheral blocks B are hydrophilic and core block A is hydrophobic. In this example, the two peripheral blocks B are substantially identical to one another with respect to composition, number average molecular weight, charge density, types of repeat units, and arrangement of repeat units.

Using "C" to represent a different hydrophobic block, the cationic triblock copolymer can have an ABC triblock structure, wherein peripheral blocks A and C are hydrophobic. Blocks A and C can differ in chemical structure, average molecular weight, hydrophobicity, stereospecificity, and/or stereochemical purity.

Using "D" to represent a different hydrophilic block, the cationic triblock copolymer can have a DAB triblock structure, wherein peripheral blocks D and B are hydrophilic peripheral blocks. Blocks D and B can differ in chemical structure, average molecular weight, hydrophilicity, charge density, quaternary amine structure, stereospecificity, and/or stereochemical purity. Optionally, block B and/or block D can comprise a cationic stereospecific repeat unit comprising an asymmetric tetravalent carbon. In an embodiment, the asymmetric tetravalent carbon is a backbone carbon.

In a preferred embodiment, the cationic triblock copolymer has an ABA triblock structure, wherein core block B is hydrophilic, peripheral blocks A are hydrophobic, and peripheral blocks A are substantially identical. The peripheral blocks can be optionally endcapped to avoid unwanted side reactions. The endcap group can comprise additional functionality that can be biologically active.

The methods that follow are directed to the formation of the cationic triblock copolymer having a hydrophilic core block. The methods are meant to be illustrative and non-limiting. The term "first cyclic carbonyl monomer" refers to a cyclic carbonyl monomer comprising a monovalent leaving group capable of reacting with a tertiary amine to form a moiety comprising a quaternary amine. The term "second cyclic carbonyl monomer" refers to a cyclic carbonyl monomer that is used to form the hydrophobic blocks. The second cyclic carbonyl monomer can be stereospecific.

A precursor triblock copolymer for the cationic triblock copolymer can be prepared in a single pot by a sequential block synthesis (i.e., Monomer→B→ABA). In this example, the core block B is formed first. In this instance, Block B contains a central chain fragment comprising a residue of a dinucleophilic initiator for the ring opening polymerization. A method comprises i) forming a reaction mixture comprising a first cyclic carbonyl monomer comprising a leaving group capable of reacting with a tertiary amine to form a quaternary amine, an organocatalyst, an optional solvent, and an optional accelerator, and a dinucleophilic initiator for a ring opening polymerization; ii) polymerizing by a ring opening reaction the first cyclic carbonyl monomer, thereby forming a second mixture comprising a first polymer comprising two living chain ends; iii) adding to the second mixture a second cyclic carbonyl monomer, the second cyclic carbonyl monomer optionally being stereospecific; iv) initiating ring opening polymerization of the second cyclic carbonyl monomer at each of the two living chain ends of the first polymer, thereby forming a precursor triblock copolymer; v) optionally endcapping the precursor triblock copolymer; and vi) treating the precursor triblock copolymer or the endcapped precursor triblock copolymer with the tertiary amine, thereby forming a cationic triblock copolymer. The cationic triblock copolymer comprises a first hydrophobic peripheral block and a second hydrophobic peripheral block, which are optionally stereospecific. The cationic triblock copolymer comprises a hydrophilic core block comprising i) a central chain fragment comprising a residue of the dinucleophilic initiator and ii) a hydrophilic repeat unit comprising a side chain moiety comprising a quaternary amine group. The cationic triblock copolymer has an ABA block structure as described further above. The method is further illustrated in Scheme 1 below and in the Examples.

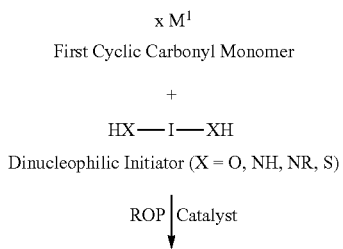

Scheme 1.

x M$^1$

First Cyclic Carbonyl Monomer

+

HX—I—XH

Dinucleophilic Initiator (X = O, NH, NR, S)

ROP | Catalyst

-continued

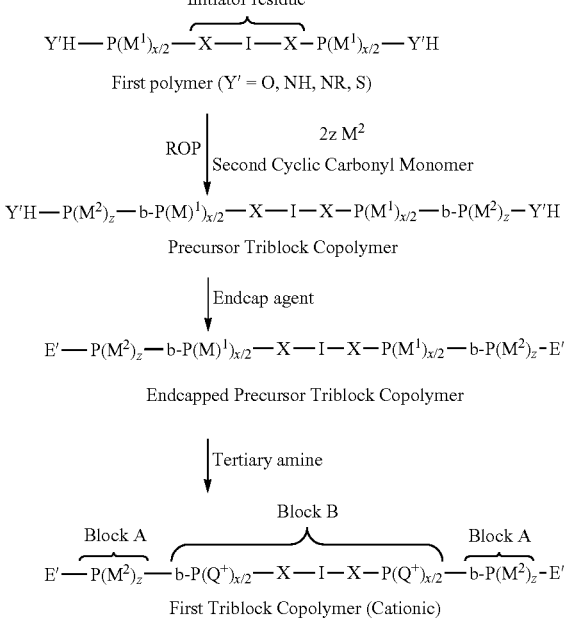

XH—I—XH is a dinucleophilic initiator (i.e., has two nucleophilic groups XH for initiating a ring opening polymerization), wherein I is a divalent carbon-containing group, and X=O, NH, NR, or S, wherein R is a monovalent carbon containing substituent. In an embodiment, the initiator is a monomeric or an oligomeric material comprising 1 to 5 repeat units. The core block is formed first using $M^1$. $M^1$ is a first cyclic carbonyl monomer comprising a leaving group capable of reacting with a tertiary amine to form a quaternary amine. HX—I—XH initiates a first ROP of $M^1$ catalyzed by an organocatalyst, thereby forming a first polymer, HY'—P$(M^1)_{x/2}$-X—I—X—P$(M^1)_{x/2}$-Y'H having two living ends. X—I—X is a residue of the initiator, the X groups are backbone heteroatoms originating from the nucleophilic initiator group, each P$(M^1)_{x/2}$-Y'H group represents a chain of ring opened polymer of $M^1$ attached to the heteroatom of the initiator fragment, and Y'H is a nucleophilic group at each living end of the first polymer chain. The Y'H groups in Scheme 1 can independently be an alcohol, amine or a thiol group (Y'=O, NH, NR, S). R in the NR group of Y' is a carbon bearing substituent. Second cyclic carbonyl monomer $M^2$, which is optionally stereospecific, is added to the reactor. $M^2$ is used to simultaneously form two substantially identical hydrophobic peripheral blocks. Y'H—P$(M^1)_{x/2}$-X—I—X—P$(M^1)_{x/2}$-Y'H initiates ring opening polymerization of $M^2$ in a second ROP. The second ROP produces a precursor triblock copolymer, Y'H—P$(M^2)_z$-P$(M^1)_{x/2}$-X—I—X—P$(M^1)_{x/2}$-P$(M^2)_z$-Y'H having two living ends, wherein P$(M^2)_z$-Y'H represents a block of ring opened polymer of $M^2$ and Y'H is a nucleophilic group at each living end of the precursor triblock copolymer chain. The notation "-b-" represents a block boundary. In this example, the precursor triblock copolymer is endcapped to form E'-P$(M^2)_z$-P$(M^1)_{x/2}$-X—I—X—P$(M^1)_{x/2}$-P$(M^2)_z$-E', wherein E' represents an endcap group. The endcapped precursor triblock copolymer is treated with a tertiary amine to form the cationic triblock copolymer E'-P$(M^2)_z$-P$(Q^+)_{x/2}$-X—I—X—P$(Q^+)_{x/2}$-P$(M^2)_z$-E', wherein P$(Q^+)_{x/2}$-X—I—X—P$(Q^+)_{x/2}$ represents the cationic core block comprising a side chain quaternary amine group. In this example Block B includes the initiator fragment X—I—X. Blocks A do not include the two endcap groups, as these can differ in each Block A.

The precursor block copolymer for the cationic triblock copolymer can be prepared in a single pot by synthesizing a peripheral block first (i.e., monomer→A→AB→ABA). For consistency with Scheme 1, the cyclic carbonyl monomer $M^2$, which is optionally stereospecific, is used again to form the hydrophobic block, but is polymerized before the first cyclic carbonyl monomer $M^1$. A method comprises i) forming a reaction mixture comprising a second cyclic carbonyl monomer, which is optionally stereospecific, an organocatalyst, an optional solvent, and an optional accelerator, and a mono-nucleophilic initiator for a ring opening polymerization; ii) polymerizing by a ring opening reaction the second cyclic carbonyl monomer, thereby forming a second mixture comprising a first polymer comprising one living chain end; iii) adding to the second mixture a first cyclic carbonyl monomer comprising a leaving group capable of reacting with a tertiary amine to form a quaternary amine; iv) initiating a ring opening polymerization of the first cyclic carbonyl monomer with the first copolymer, thereby forming a third mixture comprising a second polymer comprising one living chain end; v) adding to the third mixture a the second cyclic carbonyl monomer; vi) initiating ring opening polymerization of the second cyclic carbonyl monomer with the second polymer, thereby forming a precursor triblock copolymer; vii) optionally endcapping the precursor triblock copolymer; and viii) treating the precursor triblock copolymer or the endcapped precursor triblock copolymer with the tertiary amine, thereby forming a cationic triblock copolymer. The cationic triblock copolymer comprises a) a first hydrophobic peripheral block optionally comprising a first stereospecific repeat unit, b) a second hydrophobic peripheral block optionally comprising the first stereospecific repeat unit, and c) a hydrophilic core block comprising a repeat unit comprising a side chain quaternary amine group. In the example in which $M^2$ is stereospecific, the first and second hydrophobic peripheral blocks comprise the first stereospecific repeat unit. Alternatively, the first and second hydrophobic peripheral blocks can comprise different stereospecific repeat units. This method is further illustrated in Scheme 2.

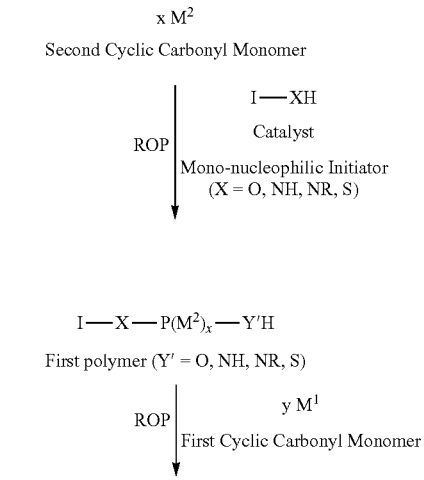

-continued

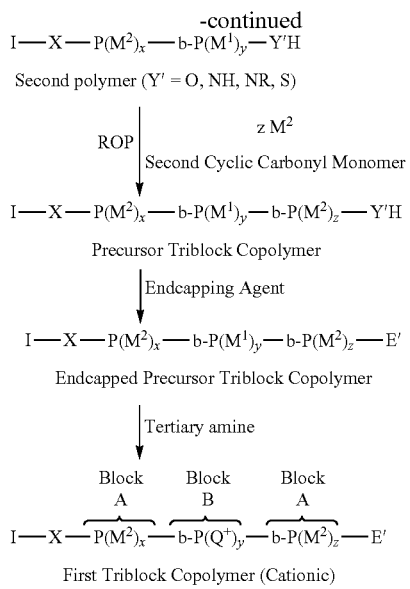

I—XH is mono-nucleophilic initiator (i.e., has one nucleophilic group XH for initiating a ring opening polymerization), wherein I is a monovalent carbon-containing group, and X=O, NH, NR, or S, wherein R is a monovalent carbon containing substituent. In an embodiment, the initiator is a monomeric or an oligomeric material comprising 1 to 5 repeat units. $M^2$ is a second cyclic carbonyl monomer, which is optionally stereospecific. In this example, $M^2$ is used to form both hydrophobic peripheral blocks A. A first portion of $M^2$ is added to the reactor. I—XH initiates polymerization of $M^2$ in a first ROP catalyzed by an organocatalyst, thereby forming a living first polymer, I—X—P$(M^2)_x$-Y'H, wherein I—X— is a residue of the initiator, X is a backbone heteroatom originating from the nucleophilic initiator group, P$(M^2)_x$-Y'H represents a block of ring opened polymer of $M^2$, and Y'H is a nucleophilic group at the living end of the first polymer chain. The Y'H groups in Scheme 2 can independently be an alcohol, amine or a thiol group (Y'=O, NH, NR, S). R in the NR group of Y' is a carbon bearing substituent. $M^1$ is added to the reactor to form the core block. $M^1$ is a first cyclic carbonyl monomer comprising a leaving group capable of reacting with a tertiary amine to form a quaternary amine. I—X—P$(M^2)_x$-Y'H initiates polymerization of $M^1$ in a second ROP. The second ROP produces a living second polymer, I—X—P$(M^2)_x$-b-P$(M^1)_y$-Y'H, wherein P$(M^1)_y$-Y'H represents a block of ring opened polymer of $M^1$ and Y'H is a nucleophilic group at the living end of the second polymer chain. Another portion of $M^2$ is added to the reactor ($M^2$ can optionally be substituted with a different stereospecific cyclic carbonyl monomer, as stated above, to produce an ABC block structure). I—X—P$(M^2)_x$-b-P$(M^2)_y$-Y'H initiates polymerization of $M^2$ in a third ROP, thereby forming precursor triblock copolymer I—X—P$(M^2)_x$-b-P$(M^1)_y$-b-P$(M^2)_z$-Y'H. In this example, the precursor triblock copolymer is endcapped to form I—X—P$(M^2)_x$-b-P$(M^1)_y$-b-P$(M^3)_z$-E', wherein E' is an endcap group. The endcapped precursor triblock copolymer is treated with a tertiary amine, thereby forming a cationic triblock copolymer I—X—P$(M^1)_x$-b-P$(Q^+)_y$-b-P$(M^1)_z$-E, wherein P$(Q^+)_y$ represents the cationic core block comprising a side chain quaternary amine group. In this example, the Blocks A do not include the initiator fragment and do not include the endcap group.

A third method of preparing the cationic triblock copolymer utilizes a pre-formed dinucleophilic polymeric initiator for ring opening polymerization. The polymeric initiator can be derived by a ring opening polymerization or another type of polymerization. The polymeric initiator comprises a repeat unit comprising a side chain leaving group capable of reacting with a tertiary amine to form a quaternary amine. A method comprises i) forming a reaction mixture comprising a stereospecific first cyclic carbonyl monomer, an organocatalyst, an optional solvent, and an optional accelerator, and a dinucleophilic polymeric initiator for a ring opening polymerization, wherein the polymeric initiator comprises a) two chain ends, wherein each chain end comprises a nucleophilic group capable of initiating a ring opening polymerization, and b) a repeat unit comprising a side chain leaving group capable of reacting with a tertiary amine to form a quaternary amine; ii) polymerizing by a ring opening reaction a second cyclic carbonyl monomer, which can optionally be stereospecific, thereby forming a precursor triblock copolymer; iii) optionally endcapping the precursor triblock copolymer; and iv) treating the precursor triblock copolymer or the endcapped precursor triblock copolymer with a tertiary amine, thereby forming a cationic triblock copolymer. The cationic triblock copolymer comprises a) a first hydrophobic peripheral block comprising a hydrophobic repeat unit that can optionally be stereospecific, b) a second hydrophobic peripheral block comprising the hydrophobic repeat unit that can optionally be stereospecific, and c) a hydrophilic core block comprising a repeat unit comprising a side chain quaternary amine.

Alternatively, the polymeric initiator comprises a repeat unit comprising a side chain quaternary amine group. A method comprises i) forming a reaction mixture comprising a hydrophobic cyclic carbonyl monomer (i.e., second cyclic carbonyl monomer) that can optionally be stereospecific, an organocatalyst, an optional solvent, and an optional accelerator, and a dinucleophilic polymeric initiator for a ring opening polymerization, wherein the polymeric initiator comprises a) two chain ends, wherein each chain end comprises a nucleophilic group capable of initiating a ring opening polymerization, and b) a repeat unit comprising a side chain quaternary amine, ii) polymerizing by a ring opening reaction the hydrophobic cyclic carbonyl monomer, thereby forming a cationic triblock copolymer, and iii) optionally endcapping the cationic triblock copolymer. The cationic triblock copolymer comprises a) a first hydrophobic peripheral block comprising a hydrophobic repeat unit that can optionally be stereospecific, b) a second hydrophobic peripheral block comprising the hydrophobic repeat unit that can optionally be stereospecific, and c) a hydrophilic core block comprising a repeat unit comprising a side chain quaternary amine.

A cyclic carbonyl monomer comprising a pendant quaternary amine group can be used to prepare the cationic triblock copolymer. However, these monomers are more difficult to prepare, are less stable, and the corresponding polymers tend to be more polydisperse. Therefore, the quaternization reaction is preferably performed after the ring-opening polymerizations.

Non-charged Triblock Copolymer.

Using "E" to represent a non-charged hydrophilic block and "F" to represent a hydrophobic block, the non-charged triblock copolymer can have a FEF triblock structure hydrophilic core block E, and the two peripheral hydrophobic blocks F that are substantially identical to one another. Alternatively, the non-charged triblock copolymer can have an EFE triblock structure, comprising two peripheral hydrophilic blocks E and a hydrophobic core block F. Hydrophilic blocks E comprise a non-charged hydrophilic repeat unit. Hydrophilic blocks E can be substantially identical to one another.

Using "G" to represent a different hydrophobic block, the non-charged triblock copolymer can have a GEF triblock structure, comprising peripheral hydrophobic block G and peripheral hydrophobic block F. Block G and block F can differ in chemical structure, average molecular weight, hydrophobicity, stereospecificity, and/or stereochemical purity.

Using "H" to represent a different hydrophilic block, the non-charged triblock copolymer can have a HFE triblock structure, comprising hydrophilic peripheral block E and hydrophilic peripheral block H. Block E and block H can differ in chemical structure, average molecular weight, hydrophilicity, stereospecificity, and/or stereochemical purity. Optionally, hydrophilic blocks E and/or H can comprise a stereospecific repeat unit comprising one or more asymmetric tetravalent carbons. In an embodiment, at least one of the asymmetric tetravalent carbons is a backbone carbon.

In a preferred embodiment, the non-charged triblock copolymer has a FEF triblock structure, comprising hydrophilic core block E and peripheral hydrophobic blocks. Hydrophobic peripheral blocks F can be substantially identical. Optionally, peripheral hydrophobic blocks F can be endcapped. The endcap group can comprise additional functionality that can be biologically active (e.g., a galactose group for targeting liver cells).

The non-charged triblock copolymer can be prepared using a sequential block synthetic approach as discussed above for the cationic triblock copolymer, omitting a quaternization step. The hydrophilic block can be formed by a ring opening polymerization or a different polymerization process.

In a specific embodiment, the non-charged triblock copolymer has an FEF triblock structure comprising a hydrophilic poly(alkylene oxide) core block E, and two substantially identical peripheral hydrophobic blocks F comprising a hydrophobic repeat unit, which is optionally stereospecific. A method comprises i) forming a reaction mixture containing a hydrophobic cyclic carbonyl monomer that is optionally stereospecific, an organocatalyst, an optional solvent, an optional accelerator, and a hydrophilic dinucleophilic polyether initiator for a ring opening polymerization, wherein the polyether initiator comprises a) two living chain ends, each of the two ends comprising a nucleophilic group for initiating a ring opening polymerization and b) an alkylene oxide repeat unit, and ii) polymerizing by a ring opening reaction the hydrophobic cyclic carbonyl monomer, thereby forming a non-charged triblock copolymer. The non-charged triblock copolymer can optionally be endcapped. In an embodiment, block F of the non-charged triblock copolymer is a stereospecific homopolymer or copolymer of D-lactide or L-lactide, and block E comprises a poly(ethylene oxide) chain segment derived from a poly(ethylene glycol) initiator.

When stereospecific repeat units are used, the hydrophobic blocks A and/or C of the cationic triblock copolymer can be formed from different stereospecific cyclic carbonyl monomers, from different stereoisomers of a given cyclic carbonyl monomer that comprises one or more asymmetric tetravalent carbons, or from the same stereoisomer of a given cyclic carbonyl monomer that comprises one or more asymmetric tetravalent carbons.

Similarly, the hydrophobic blocks F and/or G of the non-charged triblock copolymer can be formed from different stereospecific cyclic carbonyl monomers, from different stereoisomers of a given cyclic carbonyl monomer that comprises one or more asymmetric tetravalent carbons, or from the same stereoisomer of a given cyclic carbonyl monomer that comprises one or more asymmetric tetravalent carbons.

Likewise, the stereospecific repeat unit(s) of the hydrophobic blocks A (and/or C) of the cationic triblock copolymer can be a different stereospecific chemical structure, can be a different stereoisomer of a given chemical structure, or can be the same stereoisomer of a given chemical structure compared to the stereospecific repeat unit(s) of a hydrophobic block F (and/or G) of the non-charged triblock copolymer.

In a specific embodiment, the cationic triblock copolymer has an ABA triblock structure, the non-charged triblock copolymer has an FEF triblock structure, and block A and block F comprise repeat units that are different stereoisomers of the same chemical structure. As an example, block A can comprise a repeat unit comprising the R,R stereoisomer of a ring opened cyclic ester monomer having two asymmetric carbon centers (e.g., D-lactide), whereas block F can comprise the S,S stereoisomer (e.g., L-lactide), or vice versa.

Expanding on the above example using D-lactide and L-lactide, stereospecific polyester chain segments can be formed by a ring opening polymerization that comprise isotactic poly(D-lactide) (PDLA) or isotactic poly(L-lactide) (PLLA). The stereostructures of D-lactide (R,R symmetry), poly(D-lactide), L-lactide (S,S symmetry), and poly(L-lactide) are shown below.

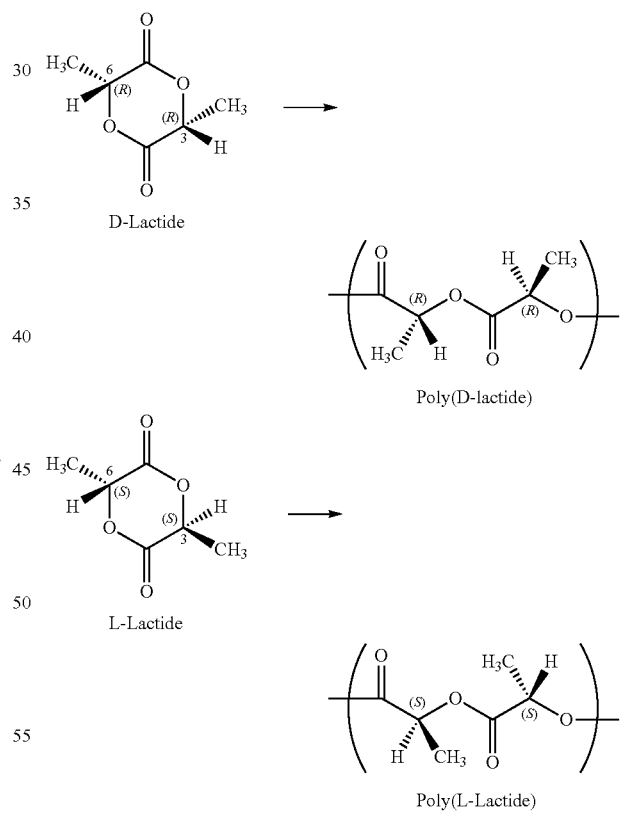

D-Lactide

Poly(D-lactide)

L-Lactide

Poly(L-Lactide)

The asymmetric carbon centers labeled 3 and 6 have R or S symmetry in accordance with CIP rules, as shown. The mirror image structure of D-lactide is not superposable. Thus, tetrads of poly(D-lactide) can have one type of R,S symmetry: RRRR. Likewise, the mirror image structure of L-lactide is not superposable, and tetrads of poly(L-lactide) can have one type of R,S symmetry: SSSS. Meso-lactide has the following R,S symmetry.

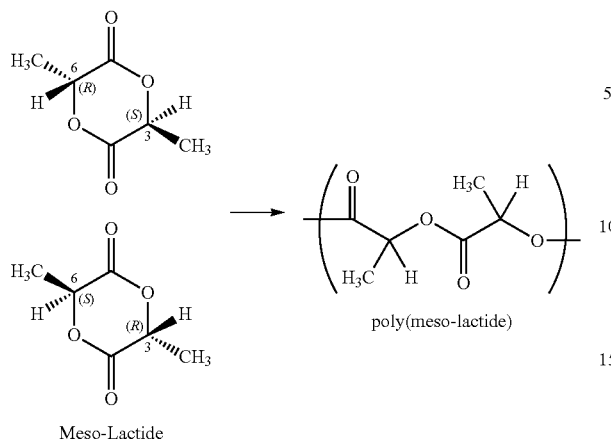

Meso-Lactide → poly(meso-lactide)

The two cyclic structures shown for meso-lactide are superposable mirror image structures. Meso-lactide undergoes ring opening polymerization to form poly(meso-lactide) having syndiotactic diads in each repeat unit, and heterotactic tetrads. That is, diads of poly(meso-lactide) can have RS or SR symmetry. Tetrads of poly(meso-lactide) can have the following R,S symmetry: RSRS, RSSR, SRRS, and SRSR.

A stereospecific repeat unit is preferably present in the cationic triblock copolymer and/or the non-charged triblock copolymer in a stereochemical purity of 90% or more, 94% or more, and more particularly 98% to 100%.

In an embodiment, block A (and/or block C) of the cationic triblock copolymer comprises a poly(L-lactide) chain and block F (and/or block G) of the non-charged triblock copolymer comprises a poly(D-lactide) chain segment. In an embodiment, block A (and/or block C) of the cationic triblock copolymer comprises a poly(D-lactide) chain segment and block F (and/or block G) of the non-charged triblock copolymer comprises a poly(L-lactide) chain segment.

Cyclic Carbonyl Monomers.

For consistency with Schemes 1 and 2, in the following description of cyclic carbonyl monomers, "first cyclic carbonyl monomer" refers to a cyclic carbonyl monomer comprising a monovalent leaving group capable of reacting with a tertiary amine to form a quaternary amine. The first cyclic carbonyl monomer can be stereospecific or non-stereospecific. "Second cyclic carbonyl monomer" refers to a cyclic carbonyl monomer that is used to form the hydrophobic blocks and is optionally stereospecific. The second cyclic carbonyl monomer can comprise one or more stereospecific asymmetric tetravalent carbons, particularly in the ring which is opened during ring opening polymerization. Additional cyclic carbonyl monomers can be selected as diluents for the first and/or the second cyclic carbonyl monomers in order to adjust, for example, hydrophobicity and/or hydrophilicity. Diluent cyclic carbonyl monomers can be stereospecific or non-stereospecific.

The first, second and diluent cyclic carbonyl monomers can be selected independently from compounds of the general formula (1):

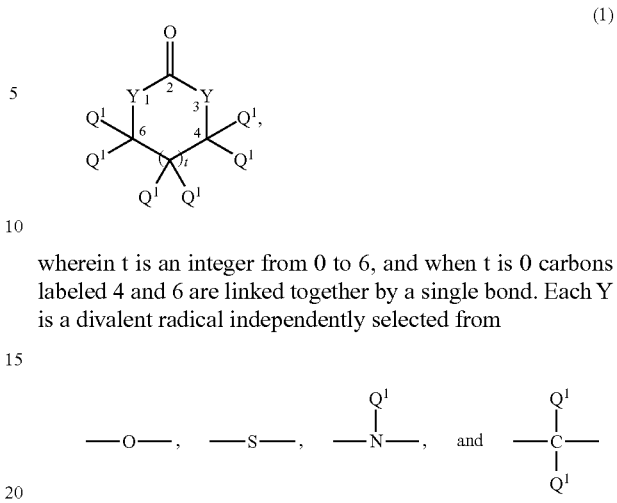

(1)

wherein t is an integer from 0 to 6, and when t is 0 carbons labeled 4 and 6 are linked together by a single bond. Each Y is a divalent radical independently selected from

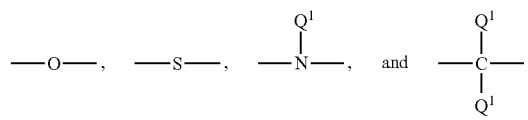

where the dash "-" indicates the point of attachment. The latter two groups are also expressed herein as —N($Q^1$)- and —C($Q^1$)$_2$-. Each $Q^1$ is a monovalent radical independently selected from the group consisting of hydrogen, halides, alkyl groups comprising 1 to 30 carbons, aryl groups comprising 6 to 30 carbon atoms, and groups having the structure

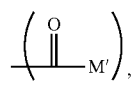

wherein M' is a monovalent radical selected from the group consisting of —$R^1$, —O$R^1$, —N(H)($R^1$), —N($R^1$)$_2$, and —S$R^1$, where the dash represents the point of attachment, and each $R^1$ is a monovalent radical independently selected from the group consisting of alkyl groups comprising 1 to 30 carbons and aryl groups comprising 6 to 30 carbons. One or more $Q^1$ groups can further comprise a monovalent leaving group capable of reacting with a tertiary amine to form a moiety comprising a quaternary amine (i.e., a positive charged quaternary ammonium ion bonded to four carbons). Non-limiting examples of monovalent leaving groups include halides in the form of an alkyl halide (e.g., alkyl chloride, alkyl bromide, or alkyl iodide), sulphonate esters (e.g., tosylate or mesylate esters), and epoxides. Each $Q^1$ group can independently be branched or non-branched. Each $Q^1$ group can also independently comprise one or more additional functional groups selected from the group consisting of ketones, aldehydes, alkenes, alkynes, cycloaliphatic rings comprising 3 to 10 carbons, heterocylic rings comprising 2 to 10 carbons, ethers, amides, esters, and combinations of the foregoing functional groups. A heterocyclic ring can comprise oxygen, sulfur and/or nitrogen. Two or more $Q^1$ groups can together form a ring. A first cyclic carbonyl monomer of formula (1) comprises one or more $Q^1$ groups comprising a monovalent leaving group capable of reacting with a tertiary amine to form a moiety comprising a quaternary amine. The first cyclic carbonyl monomer can be stereospecific or non-stereospecific. A second cyclic carbonyl monomer of formula (1) is hydrophobic, and optionally comprises one or more stereospecific asymmetric tetravalent carbons.

A ring opened polymer formed with a cyclic carbonyl monomer of formula (1) can have a backbone functional group selected from the group consisting of polyesters, poly-carbonates, polyureas, polycarbamates, polythiocarbamates, polydithiocarbonates, and combinations thereof, which have a repeat structure as shown in (Table 1):

TABLE 1

| Polyester | 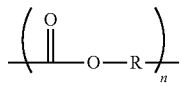 |
| --- | --- |
| Polycarbonate | 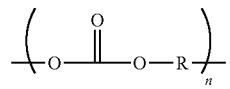 |
| Polyurea | 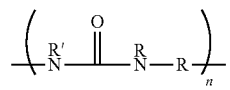 |
| Polycarbamate | 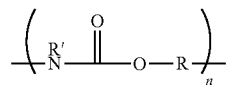 |
| Polythiocarbamate | 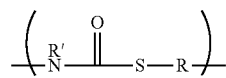 |
| Polythiocarbonate | 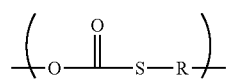 |
| Polydithiocarbonate | 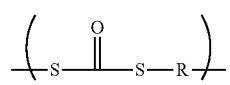 |

The ring opened polymer chain formed with a cyclic carbonyl monomer of formula (1) has a repeat unit having the general formula (2):

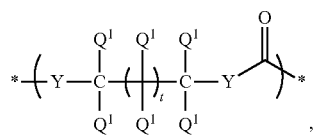

(2)

wherein Y, t, and $Q^1$ are defined as above.

The first, second and diluent cyclic carbonyl monomers can be selected independently from compounds of the general formula (3):

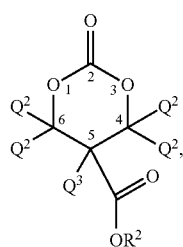

(3)

wherein $Q^2$ is a monovalent radical independently selected from the group consisting of hydrogen, halides, alkyl groups comprising 1 to 30 carbons, aryl groups comprising 6 to 30 carbon atoms, and groups having the structure

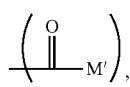

wherein M' is a monovalent radical selected from the group consisting of $-R^1$, $-OR^1$, $-N(H)(R^1)$, $-N(R^1)_2$, and $-SR^1$, wherein each $R^1$ is a monovalent radical independently selected from the group consisting of alkyl groups comprising 1 to 30 carbons and aryl groups comprising 6 to 30 carbons, $R^2$ is a monovalent radical independently selected from the group consisting of alkyl groups comprising 1 to 30 carbons and aryl groups comprising 6 to 30 carbons, and $Q^3$ is a monovalent radical selected from the group consisting of hydrogen, alkyl groups having 1 to 30 carbons, and aryl groups having 6 to 30 carbons. In an embodiment, each $Q^2$ is hydrogen, $Q^3$ is a methyl or ethyl group, and $R^2$ is an alkyl group comprising 1 to 30 carbons. A first cyclic carbonyl monomer of formula (3) comprises an $R^2$ group comprising a monovalent leaving group capable of reacting with a tertiary amine to form a moiety comprising a quaternary amine. A second cyclic carbonyl monomer of formula (3) comprises one or more stereospecific asymmetric tetravalent carbons, particularly carbons labeled 4, 5, and 6 in formula (3)).

The ring opened polymer chain formed with a cyclic carbonyl monomer of formula (3) has a backbone carbonate repeat unit having the general formula (4):

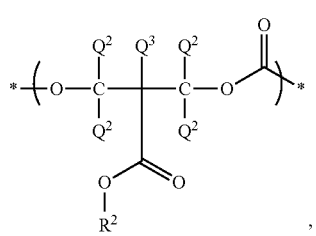

(4)

wherein $Q^2$, $Q^3$, and $R^2$ are defined as above.

The first, second and diluent cyclic carbonyl monomers can be selected from cyclic esters of the general formula (5):

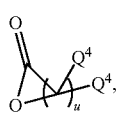

(5)

wherein u is an integer from 1 to 8, each $Q^4$ is a monovalent radical independently selected from the group consisting of hydrogen, halides, alkyl groups comprising 1 to 30 carbons, aryl groups comprising 6 to 30 carbon atoms, and groups having the structure

where M' is a monovalent radical selected from the group consisting of —R¹, —OR¹, —N(H)(R¹), —N(R¹)₂, and —SR¹, wherein each R¹ is a monovalent radical independently selected from the group consisting of alkyl groups comprising 1 to 30 carbons and aryl groups comprising 6 to 30 carbons. The lactone ring can optionally comprise a carbon-carbon double bond; that is, optionally, a

group of formula (5) can independently represent a

group. The lactone ring can also comprise a heteroatom such as oxygen, nitrogen, sulfur, or a combination thereof; that is, optionally a

group of formula (5) can independently represent a —O—, —S—, —N(H)—, or an —N(R¹)— group, wherein R¹ has the same definition as above. A first cyclic carbonyl monomer of formula (5) comprises one or more Q⁴ groups comprising a monovalent leaving group capable of reacting with a tertiary amine to form a moiety comprising a quaternary amine. A second cyclic carbonyl monomer of formula (5) comprises one or more stereospecific asymmetric tetravalent carbons, particularly in the lactone ring.

The ring opened polymer chain formed with a cyclic carbonyl monomer of formula (5) has a backbone ester repeat unit having the general formula (6):

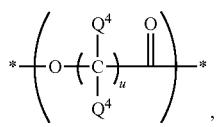
(6)

wherein Q⁴ and u are defined as above.

The first, second and diluent cyclic carbonyl monomers can be selected from a dioxane dicarbonyl monomers of the general formula (7):

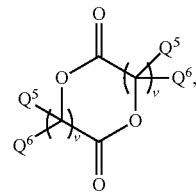
(7)

wherein each $Q^5$ is a monovalent radical independently selected from the group consisting of hydrogen, halides, carboxy groups, alkyl groups comprising 1 to 30 carbons, aryl groups comprising 6 to 30 carbon atoms, and groups having the structure

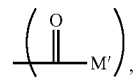

where each v is independently an integer from 1 to 6, M' is a monovalent radical selected from the group consisting of —R¹, —OR¹, —NH(R¹)₂, and —SR¹, wherein each R¹ is a monovalent radical independently selected from the group consisting of alkyl groups comprising 1 to 30 carbons and aryl groups comprising 6 to 30 carbons, each $Q^6$ is a monovalent group independently selected from the group consisting of hydrogen, alkyl groups having 1 to 30 carbons, and aryl groups having 6 to 30 carbons. A first cyclic carbonyl monomer of formula (7) comprises one or more Q⁵ groups and/or a Q⁶ groups comprising a monovalent leaving group capable of reacting with a tertiary amine to form a moiety comprising a quaternary amine. A second cyclic carbonyl monomer of formula (7) comprises one or more stereospecific asymmetric tetravalent carbons, more particularly one or more carbons of the dioxane dicarbonyl ring. In an embodiment, the second cyclic carbonyl monomer comprises a compound of formula (7) wherein each v is 1, each Q⁵ is hydrogen, and each Q⁶ is an alkyl group comprising 1 to 6 carbons. In an embodiment, the second cyclic carbonyl monomer is D-lactide or L-lactide.

The ring opened polymer chain formed with a cyclic carbonyl monomer of formula (7) has a backbone ester repeat unit having the general formula (8):

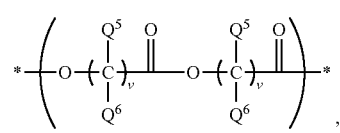
(8)

wherein Q⁵, Q⁶, and v are defined as above.

Examples of cyclic carbonyl monomers of formulas (1) or (3) having a monovalent leaving group in the form of an alkyl halide include the cyclic monomers of Table 2.

TABLE 2

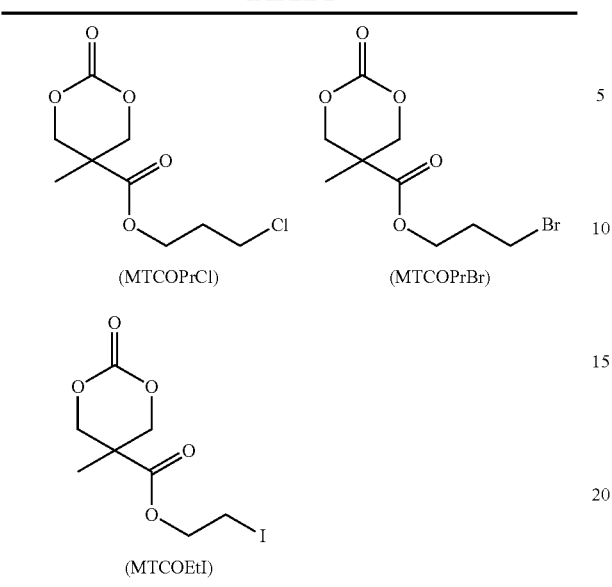

Additional examples of cyclic carbonyl monomers of formula (1) and (3) include the compounds of Table 3. These can be used, for example, as diluent comonomers in the ring-opening polymerization of the halide containing monomers of Table 2, to form a block A comprising a random copolymer chain.

TABLE 3

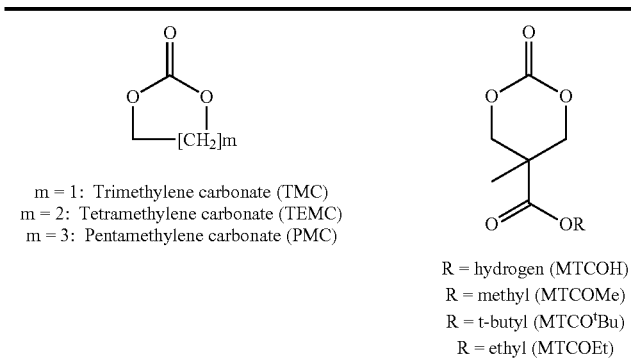

m = 1: Trimethylene carbonate (TMC)
m = 2: Tetramethylene carbonate (TEMC)
m = 3: Pentamethylene carbonate (PMC)

R = hydrogen (MTCOH)
R = methyl (MTCOMe)
R = t-butyl (MTCO$^t$Bu)
R = ethyl (MTCOEt)

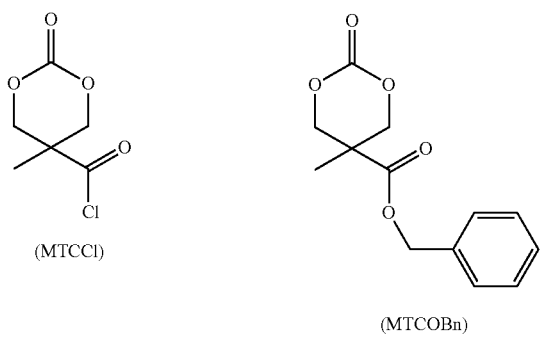

TABLE 3-continued
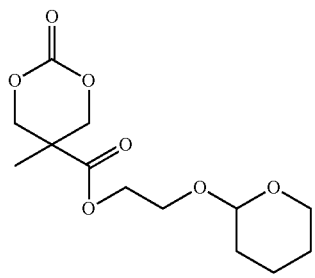 [SMILES: CC1(C(=O)OCCOC2CCCCO2)COC(=O)OC1] 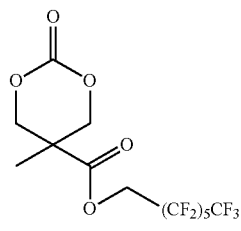
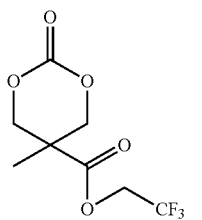
(MTCTFE)
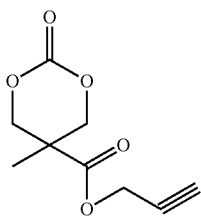
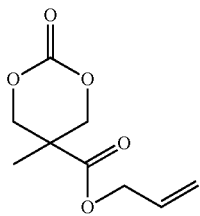 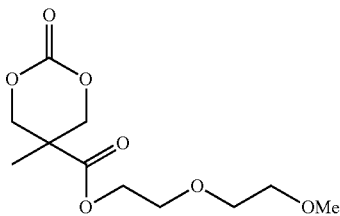 [SMILES: COCCOCCOC(=O)C1(C)COC(=O)OC1]
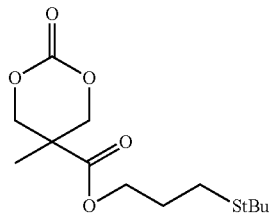 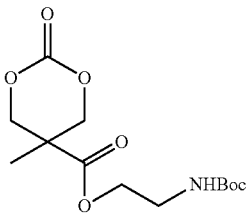 [SMILES: CC(C)(C)OC(=O)NCCOC(=O)C1(C)COC(=O)OC1]
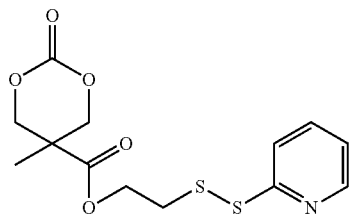 [SMILES: CC1(C(=O)OCCSSc2ccccn2)COC(=O)OC1] 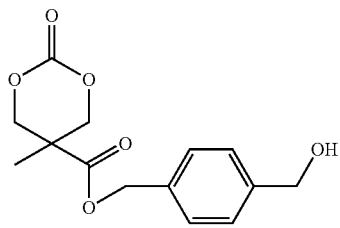 [SMILES: CC1(C(=O)OCc2ccc(CO)cc2)COC(=O)OC1]
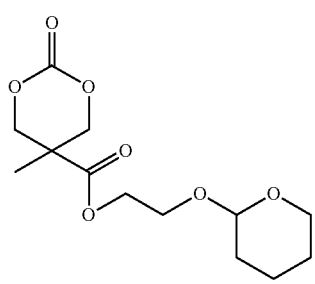 [SMILES: CC1(C(=O)OCCOC2CCCCO2)COC(=O)OC1] 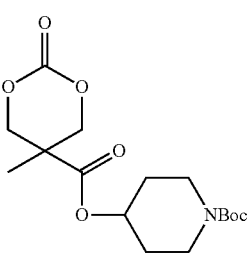 [SMILES: CC(C)(C)OC(=O)N1CCC(OC(=O)C2(C)COC(=O)OC2)CC1]

TABLE 3-continued

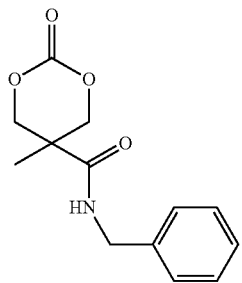 [SMILES: CC1(C(=O)NCc2ccccc2)COC(=O)OC1]
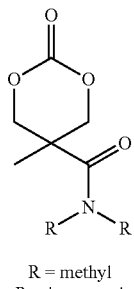

R = methyl
R = iso-propyl

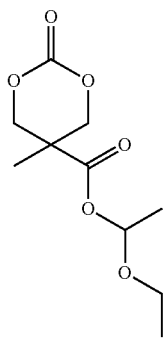

(MTCOEE)

Examples of cyclic carbonyl monomers of formula (5) include the compounds of Table 4, and stereospecific versions thereof, where feasible, comprising one or more stereospecific asymmetric ring carbons.

TABLE 4

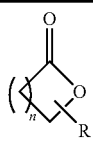
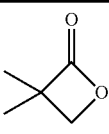

R = H; n = 1: beta-Propiolactone (b-PL)
R = H; n = 2: gamma-Butyrolactone (g-BL)
R = H; N = 3: delta-Valerolactone (d-VL)
R = H; n = 4: epsilon-Caprolactone (e-CL)
R = CH$_3$; n = 1: beta-Butyrolactone (b-BL)
R = CH$_3$; n = 2: gamma-Valerolactone (g-VL)

Pivalolactone
(PVL)

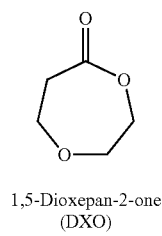
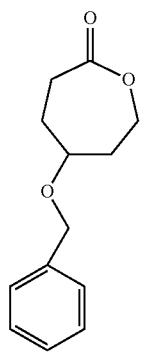

1,5-Dioxepan-2-one
(DXO)

5-(Benzyloxy)oxepan-2-one
(BXO)

TABLE 4-continued
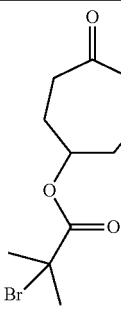
7-Oxooxepan-4-yl 2-bromo-2-methylpropanoate (BMP-XO)
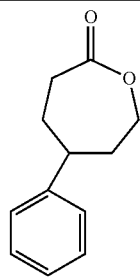
5-Phenyloxepan-2-one (PXO)
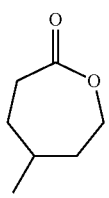
5-Methyloxepan-2-one (MXO)
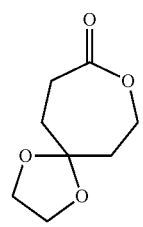
1,4,8-Trioxa(4,6)spiro-9-undecane (TOSUO)
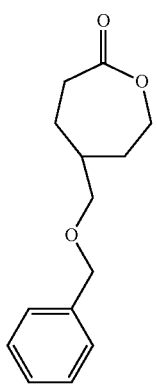
5-(Benzyloxymethyl)oxepan-2-one (BOMXO)
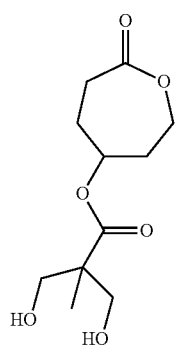
7-Oxooxepan-4-yl 3-hydroxy-2-(hydroxymethyl)-2-methylpropanoate (OX-BHMP)
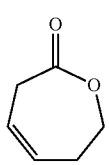
(Z)-6,7-Dihydrooxepin-2(3H)-one (DHXO)
Examples of cyclic carbonyl monomers of formula (7) include the compounds of Table 5.

TABLE 5

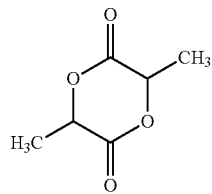

D-Lactide (DLA),
L-Lactide (LLA), or
racemic Lactide, 1:1 D:L forms (DLLA)

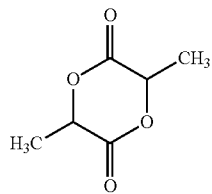

meso-Lactide (MLA)
(two opposite centers of asymmetry,
R and S)

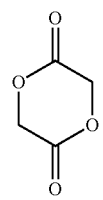

Glycolide (GLY)

The above monomers can be purified by recrystallization from a solvent such as ethyl acetate or by other known methods of purification, with particular attention being paid to removing as much water as possible from the monomer. The monomer moisture content can be from 1 to 10,000 ppm, 1 to 1,000 ppm, 1 to 500 ppm, and most specifically 1 to 100 ppm, by weight of the monomer.

ROP Initiators.

Initiators for ring opening polymerizations generally include nucleophilic groups such as alcohols, primary amines, secondary amines, and thiols. The initiator can comprise one or more nucleophilic initiator groups, as appropriate based on the above-described methods of preparing the cationic and non-charged triblock copolymers. The initiator can be a monomer, oligomer, or polymeric initiator as appropriate based on the above-described methods. The initiator can include other functional groups, including protected nucleophilic groups that include protected thiols, protected amines, and protected alcohols. Exemplary monomeric mono-nucleophilic initiators include mono-alcohols, such as methanol, ethanol, propanol, butanol, pentanol, amyl alcohol, capryl alcohol, nonyl alcohol, decyl alcohol, undecyl alcohol, lauryl alcohol, tridecyl alcohol, myristyl alcohol, pentadecyl alcohol, cetyl alcohol, heptadecyl alcohol, stearyl alcohol, nonadecyl alcohol and other aliphatic saturated alcohols, cyclopentanol, cyclohexanol, cycloheptanol, cyclooctanol and other aliphatic cyclic alcohols; phenol, substituted phenols, benzyl alcohol, substituted benzyl alcohols, and the like. Exemplary polymeric mono-nucleophilic initiators include mono-endcapped poly(ethylene glycols), and mono-endcapped poly(propylene glycols). Exemplary monomeric and oligomeric dinucleophilic initiators include benzenedimethanol, hydroquinone, resorcinol, propylene glycol, ethylene glycol, diethylene glycol, and triethylene glycol.

Other dinucleophilic initiators include monomeric diols such as 1,3-propanediol, 1,4-butanediol, 1,5-pentanediol, 1,6-hexanediol, and the like. An even more specific dinucleophilic initiator is BnMPA, a precursor used in the preparation of cyclic carbonate monomers:

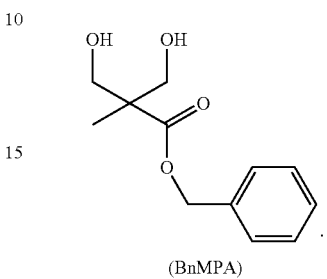

(BnMPA)

The polymeric dinucleophilic initiator can be a polyether diol, more specifically a poly(alkylene glycol) of the general formula (9):

$$HO-[CH_2(CHR^1)_xCHR^1O]_n-H \qquad (9),$$

wherein x is 0 to 8, n is an integer from 2 to 10000, each $R^1$ is a monovalent radical independently selected from the group consisting of hydrogen, and groups comprising 1 to 10 carbons. Thus, the ether repeat unit can comprise 2 to 10 backbone carbons between each backbone oxygen. As non-limiting examples, the poly(alkylene glycol) can be a poly(ethylene glycol) (PEG), having the structure HO—[CH$_2$CH$_2$O]$_n$—H, a poly(propylene glycol) (PPG), having the structure HO—[CH$_2$C(H)(CH$_3$)O]$_n$—H, or a mixture thereof.

The dinucleophilic polyether initiator can comprise nucleophilic chain end groups independently selected from the group consisting alcohols, primary amines, secondary amines, and thiols. Non-limiting examples include:

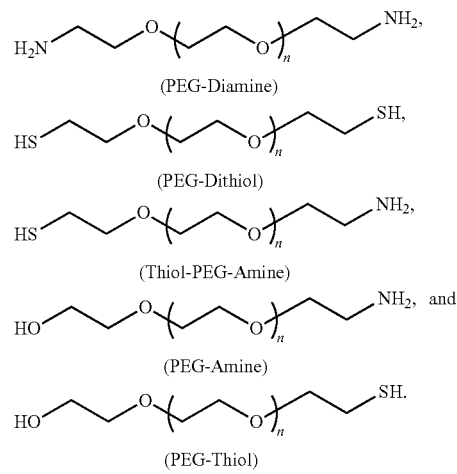

One or both end units of the dinucleophilic polyether initiator can be derivatized with substituents having a nucleophilic initiator group for ring opening polymerization, as in poly(alkylene oxide)s of general formula (10):

$$Z'-[CH_2(CHR^1)_xCHR^1O]_n-Z'' \qquad (10)$$

wherein x is 0 to 8, n is an integer from 2 to 10000, each $R^1$ is a monovalent radical independently selected from the group consisting of hydrogen and substituents comprising 1 to 10 carbons, Z' is a monovalent radical selected from the group consisting of —OH, —NH$_2$, secondary amines, —SH, and $C_1$-$C_{50}$ groups comprising a nucleophilic initiator group for ring opening polymerization, Z" is a monovalent radical selected from the group consisting of hydrogen and $C_1$-$C_{50}$ groups comprising a nucleophilic initiator group for ring opening polymerization. At least one of Z' and Z" comprises a $C_1$-$C_{50}$ group comprising a nucleophilic initiator group for ring opening polymerization, the nucleophilic initiator group selected from the group consisting of alcohols, primary amines, secondary amines, and thiols. In an embodiment, Z' and/or Z" comprises a biologically active moiety. In an embodiment x is 0 or 1, and each $R^1$ is independently hydrogen or methyl.

The number average molecular weight of the dinucleophilic polyether initiator can be from 100 to 100,000, more specifically 100 to 10000, and even more specifically, 100 to 5000.

The ROP initiator can comprise three or more nucleophilic initiator groups suitable for formation of a star polymer. As an example, G-2(OH)$_{12}$, shown below, has 12 nucleophilic hydroxy groups capable of initiating ring opening polymerization of one or more cyclic carbonyl monomers (e.g., L-lactide, D-lactide, cyclic carbonates, lactones, and the like) to form a ROP star polymer comprising 12 polymer arms, such as SP12 (Scheme 3).

Scheme 3.

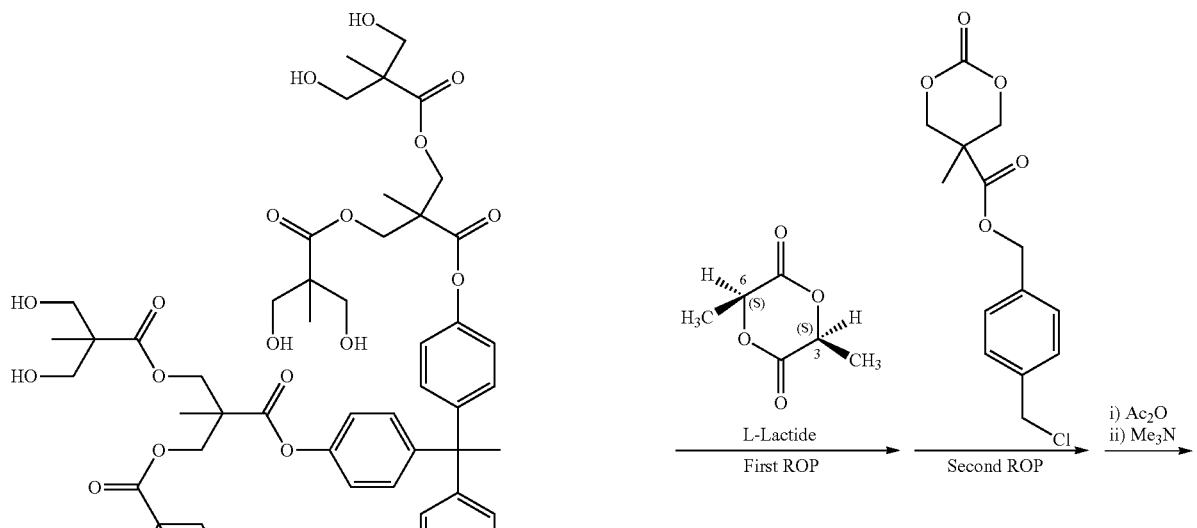

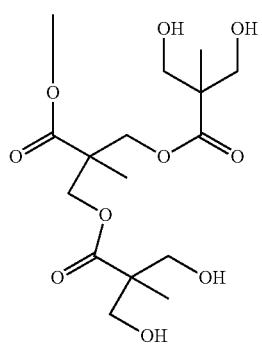

G-2(OH)$_{12}$

-continued
SP12
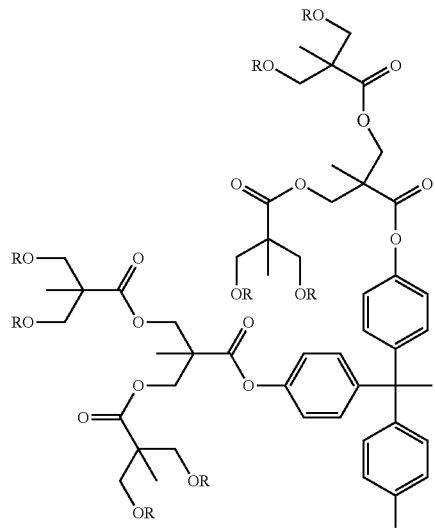
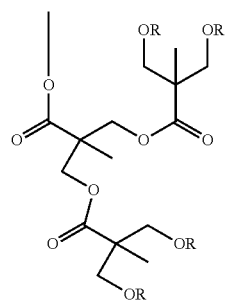
SP12
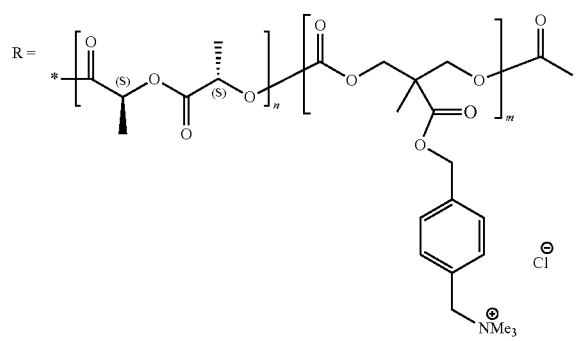

The starred bond represents the point of attachment of each R group (a polymer arm) to an oxygen in the SP12 structure. Thus, SP12 has 12 polymer arms, each polymer arm independently comprising an inner hydrophobic poly(L-lactide) block attached to a core structure derived from G-2(OH)$_{12}$, and a peripheral cationic polycarbonate block attached to the poly(L-lactide) block. The order of the foregoing ring opening polymerizations can be reversed, resulting in a star polymer having a peripheral hydrophobic block, as shown in SP13 below.

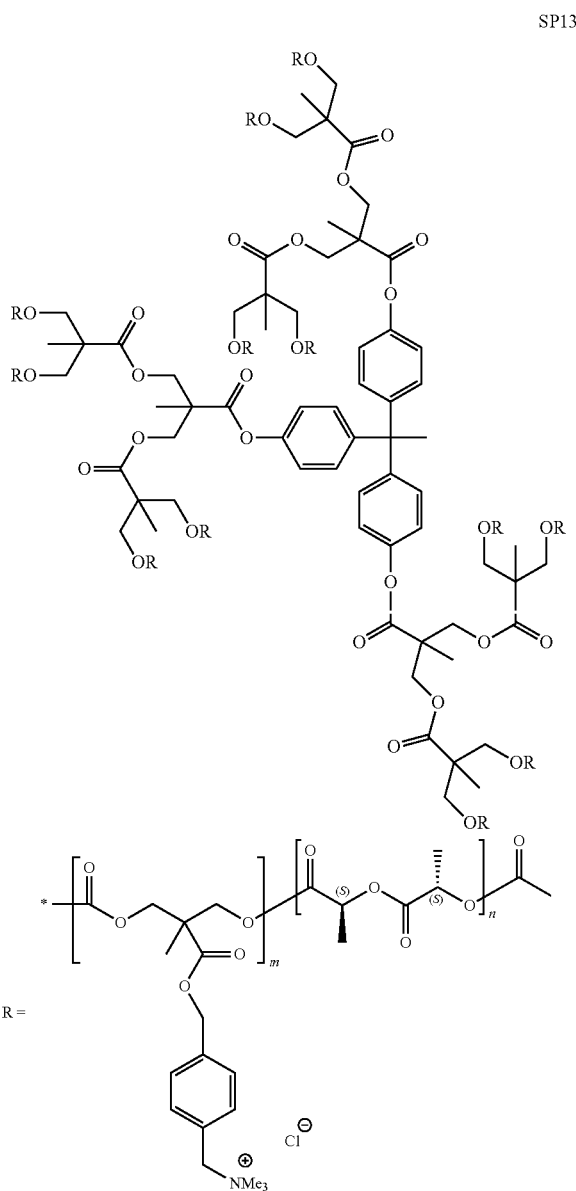

The L-lactide can be substituted with D-lactide in the ring opening polymerization to form a star polymer having opposite stereospecificity if desired.

Endcap Agents.

An endcap agent can prevent further chain growth and stabilize the reactive end groups minimize unwanted side reactions, such as chain scission. Endcap agents include, for example, materials for converting terminal hydroxyl groups to esters, such as carboxylic acid anhydrides, carboxylic acid chlorides, or reactive esters (e.g., p-nitrophenyl esters). In an embodiment, the endcap agent is acetic anhydride, which converts reactive hydroxy end groups to acetate ester groups. The endcap group can also be a biologically active moiety.

Quaternization Reaction.

The precursor triblock polymer comprises repeat units derived from the first cyclic carbonyl monomer that comprise a side chain moiety comprising a reactive monovalent leaving group capable of reacting with a tertiary amine to form a quaternary amine. The precursor triblock copolymer (Schemes 1 and 2) is treated with a tertiary amine to form the cationic triblock copolymer. The quaternization reaction is accompanied by minimal, if any, crosslinking of the cationic triblock copolymer. The quaternary nitrogen is preferentially linked to a polymer side chain carbon. Alternatively, the quaternary nitrogen can be linked directly to a backbone carbon. The positively charged quaternary amine groups provide binding strength to negatively charged biologically active materials.

No limitation is placed on the structure of the tertiary amine, as long as the tertiary amine is capable of reacting with more than 0% of the monovalent leaving groups of the precursor triblock copolymer, which are derived from the first cyclic carbonyl monomer, to form a quaternary amine, more preferably 10% or more, 20% or more, 30% or more, 40% or more, 50% or more, 60% or more, 70% or more, or more particularly 80% or more of the monovalent leaving groups of the precursor triblock copolymer.

The tertiary amine can comprise a single nitrogen such as a trialkylamine, including but not limited to trimethylamine, triethylamine, tripropylamine, and the like. The tertiary amine can further comprise additional functional groups, in particular a carboxylic acid group, for example 3-(N,N-dimethylamino)propionic acid. In such instances, the cationic triblock copolymer will comprise first repeat units comprising a side chain moiety comprising a quaternary amine group and a carboxylic acid group.

The tertiary amine can also comprise isotopically enriched versions of the tertiary amine, such as trimethylamine-$^{14}$C, trimethylamine-$^{15}$N, trimethylamine-$^{15}$N, trimethyl-$^{13}$C$_3$-amine, trimethyl-d$_9$-amine, and trimethyl-d$_9$-amine-$^{15}$N. The tertiary amine can also comprise a radioactive moiety suitable for targeting a specific cell type, such as a cancer cell. The radioactive moiety can comprise a heavy metal radioactive isotope.

In an embodiment, the tertiary amine is a bis-tertiary amine, and the cationic triblock copolymer comprises a side chain moiety comprising a quaternary amine group and a tertiary amine group. The side chain tertiary amine groups provide buffering capacity to facilitate release of the biologically active material from the loaded complex. Bis-tertiary amines have the general formula (11):

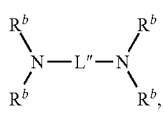

(11)

wherein L" is a divalent linking group comprising 2 to 30 carbons, and each monovalent Rb group is independently selected from alkyl groups comprising 1 to 30 carbons or aryl groups comprising 6 to 30 carbons. Each $R^b$ group can independently be branched or non-branched. Each $R^b$ group can independently comprise additional functional groups such as a ketone group, aldehyde group, hydroxyl group, alkene group, alkyne group, cycloaliphatic ring comprising 3 to 10 carbons, heterocylic ring comprising 2 to 10 carbons, ether group, amide group, ester group, and combinations of the foregoing additional functional groups. The heterocyclic ring can comprise oxygen, sulfur and/or nitrogen. Two or more Rb groups can also together form a ring. Representative L" groups include —$(CH_2)_{z'}$— where z' is an integer from 2 to 30, —$(CH_2CH_2O)_{z''}CH_2CH_2$— where z" is an integer from 1 to 10, —$CH_2CH_2SCH_2CH_2$—, —$CH_2CH_2SSCH_2CH_2$—, —$CH_2CH_2SOCH_2CH_2$—, and —$CH_2CH_2SO_2CH_2CH_2$—. L" can further comprise a monovalent or divalent cycloaliphatic ring comprising 3 to 20 carbons, a monovalent or divalent aromatic ring comprising 6 to 20 carbons, a ketone group, aldehyde group, hydroxyl group, alkene group, alkyne group, a heterocyclic ring comprising 2 to 10 carbons, ether group, amide group, ester group, and combinations of the foregoing functional groups. The heterocyclic ring can comprise oxygen, sulfur and/or nitrogen. The bis-tertiary amine can also comprise isotopically enriched forms of the bis-tertiary amine, such as deuterium, carbon-13, and/or nitrogen-15 enriched forms thereof.

More specific bis-tertiary amines include N,N,N',N'-tetramethyl-1,2-ethanediamine (TMEDA), N,N,N',N'-tetramethyl-1,3-propanediamine (TMPDA), N,N,N',N'-tetramethyl-1,4-butanediamine (TMBDA), N,N,N',N'-tetraethyl-1,2-ethanediamine (TEEDA), N,N,N',N'-tetraethyl-1,3propanediamine (TEPDA), 1,4-bis(dimethylamino)cyclohexane, 1,4-bis(dimethylaminobenzene), N,N,N',N'-tetraethyl-1,4-butanediamine (TEBDA), 4-dimethylaminopyridine (DMAP), 4,4-dipyridyl-1,4-diazabicyclo[2.2.2]octane (DABCO), 4-pyrrolidinopyridine, 1-methylbenzimidazole, and combinations thereof. In an embodiment, the bis-tertiary amine is TMEDA.

The precursor triblock copolymer is treated with the tertiary amine in a suitable organic solvent, such as acetonitrile, dimethylsulfoxide (DMSO), dimethylformamide (DMF), combinations thereof, and the like, to form the cationic triblock copolymer. The reaction is conducted under anhydrous conditions, at ambient or elevated temperature using excess tertiary amine relative to the monovalent leaving group. In general, the tertiary amine is used in an amount of from 2 to 30 moles per mole of monovalent leaving group in the precursor triblock copolymer, more particularly 3 to 20 moles per mole of monovalent leaving group in the precursor triblock copolymer. The positive charged quaternary amine forms a salt with the displaced leaving group, which becomes a negatively charged counterion. Alternatively, the negatively charged counterion can be ion exchanged with another more suitable negatively charged counterion using known methods, if desired.

The cationic triblock copolymer can be isolated by removing excess solvent and amine by vacuum, or by precipitating the cationic triblock copolymer in an organic solvent such as tetrahydrofuran, followed by filtration and drying in vacuo. More than 0% of the repeat units derived from the first cyclic carbonyl monomer comprise a side chain moiety comprising a quaternary amine group. When the precursor triblock copolymer is treated with a bis-tertiary amine, more than 0% of the repeat units derived from the first cyclic carbonyl monomer comprise a side chain moiety comprising a quaternary amine group and a tertiary amine group. When the precursor triblock copolymer is treated with a tertiary amine comprising a carboxy group or a latent carboxylic acid group, more than 0% of the first repeat units derived from the first cyclic carbonyl monomer comprise the side chain moiety comprising the quaternary amine and a carboxylic acid or a latent carboxylic acid group. The quaternary amine group is present in the cationic triblock copolymer in an amount greater than 0% of the side chain monovalent leaving groups derived from the first cyclic carbonyl monomer. More particularly, the quaternary amine group is present in the cationic triblock copolymer in an amount of 10% to 100%, 20% to 100%, 30% to 100%, 40% to 100%, 50% to 100%, 60% to 100%, 70% to 100%, or 80% to 100% of the side chain monovalent leaving groups derived from the first cyclic carbonyl monomer. When the precursor triblock copolymer is treated with a bis-tertiary amine, the tertiary amine group can be present in the cationic triblock copolymer in an amount greater than 0% of the repeat units comprising a monovalent leaving groups of the precursor triblock copolymer, more particularly 10% to 100%, 20% to 100%, 30% to 100%, 40% to 100%, 50% to 100%, 60% to 100%, 70% to 100%, or 80% to 100% of the repeat units comprising a monovalent leaving groups of the precursor triblock copolymer.

Ring Opening Polymerizations (ROP).

The following description of methods, conditions and materials for ring opening polymerizations is applicable to the preparation of the cationic triblock copolymer and non-charged triblock copolymer.

The ring-opening polymerization can be performed at a temperature that is about ambient temperature or higher, 15° C. to 200° C., and more specifically 20° C. to 200° C. When the reaction is conducted in bulk, the polymerization is performed at a temperature of 50° C. or higher, and more particularly 100° C. to 200° C. Reaction times vary with solvent, temperature, agitation rate, pressure, and equipment, but in general the polymerizations are complete within 1 to 100 hours.

The ROP reaction can be performed with or without the use of a solvent. Optional solvents include dichloromethane, chloroform, benzene, toluene, xylene, chlorobenzene, dichlorobenzene, benzotrifluoride, petroleum ether, acetonitrile, pentane, hexane, heptane, 2,2,4-trimethylpentane, cyclohexane, diethyl ether, t-butyl methyl ether, diisopropyl ether, dioxane, tetrahydrofuran, or a combination comprising one of the foregoing solvents. When a solvent is present, a suitable monomer concentration is about 0.1 to 5 moles per liter, and more particularly about 0.2 to 4 moles per liter.

Whether performed in solution or in bulk, the ROP polymerizations are conducted under an inert (i.e., dry) atmosphere, such as nitrogen or argon, and at a pressure of from 100 to 500 MPa (1 to 5 atm), more typically at a pressure of 100 to 200 MPa (1 to 2 atm). At the completion of the reaction, the solvent can be removed using reduced pressure.

Less preferred catalysts for the ROP polymerization include metal oxides such as tetramethoxy zirconium, tetra-iso-propoxy zirconium, tetra-iso-butoxy zirconium, tetra-n-butoxy zirconium, tetra-t-butoxy zirconium, triethoxy aluminum, tri-n-propoxy aluminum, tri-iso-propoxy aluminum, tri-n-butoxy aluminum, tri-iso-butoxy aluminum, tri-sec-butoxy aluminum, mono-sec-butoxy-di-iso-propoxy aluminum, ethyl acetoacetate aluminum diisopropylate, aluminum tris(ethyl acetoacetate), tetraethoxy titanium, tetra-iso-propoxy titanium, tetra-n-propoxy titanium, tetra-n-butoxy titanium, tetra-sec-butoxy titanium, tetra-t-butoxy titanium, tri-iso-propoxy gallium, tri-iso-propoxy antimony, tri-iso-butoxy antimony, trimethoxy boron, triethoxy boron, tri-iso-propoxy boron, tri-n-propoxy boron, tri-iso-butoxy boron, tri-n-butoxy boron, tri-sec-butoxy boron, tri-t-butoxy boron, tri-iso-propoxy gallium, tetramethoxy germanium, tetraethoxy germanium, tetra-iso-propoxy germanium, tetra-n-propoxy germanium, tetra-iso-butoxy germanium, tetra-n-butoxy germanium, tetra-sec-butoxy germanium and tetra-t-butoxy germanium; halogenated compound such as antimony pentachloride, zinc chloride, lithium bromide, tin(IV) chloride, cadmium chloride and boron trifluoride diethyl ether; alkyl aluminum such as trimethyl aluminum, triethyl aluminum, diethyl aluminum chloride, ethyl aluminum dichloride and tri-iso-butyl aluminum; alkyl zinc such as dimethyl zinc, diethyl zinc and diisopropyl zinc; heteropolyacids such as phosphotungstic acid, phosphomolybdic acid, silicotungstic acid and alkali metal salt thereof; zirconium compounds such as zirconium acid chloride, zirconium octanoate, zirconium stearate, and zirconium nitrate.

The catalyst is preferably an organocatalyst whose chemical formula contains none of the above-described restricted metals. Examples of organocatalysts for ring opening polymerizations include tertiary amines such as triallylamine, triethylamine, tri-n-octylamine and benzyldimethylamine 4-dimethylaminopyridine, phosphines, N-heterocyclic carbenes (NHC), bifunctional aminothioureas, phosphazenes, amidines, and guanidines.

A more specific organocatalyst is N-(3,5-trifluoromethyl)phenyl-N'-cyclohexyl-thiourea (TU):

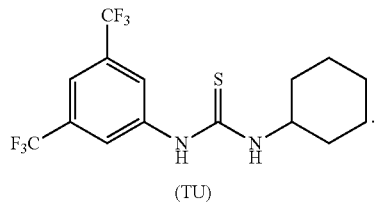

(TU)

Other ROP organocatalysts comprise at least one 1,1,1,3,3,3-hexafluoropropan-2-ol-2-yl (HFP) group. Singly-donating hydrogen bond catalysts have the formula (12):

wherein $R^2$ represents a hydrogen or a monovalent radical having from 1 to 20 carbons, for example an alkyl group, substituted alkyl group, cycloalkyl group, substituted cycloalkyl group, heterocycloalkyl group, substituted heterocycloalkyl group, aryl group, substituted aryl group, or a combination thereof. Exemplary singly-donating hydrogen bonding catalysts are listed in Table 6.

TABLE 6

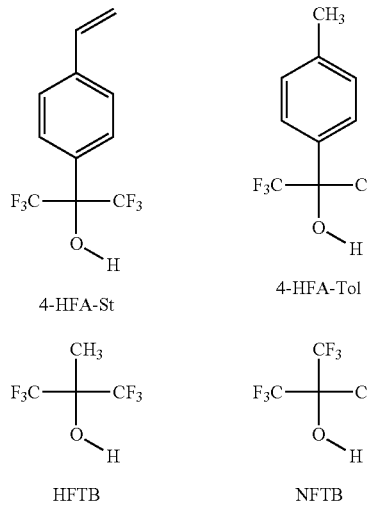

TABLE 6-continued

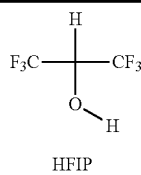

HFIP

Doubly-donating hydrogen bonding catalysts have two HFP groups, represented by the general formula (13):

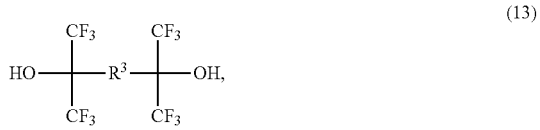

wherein $R^3$ is a divalent radical bridging group containing from 1 to 20 carbons, such as an alkylene group, a substituted alkylene group, a cycloalkylene group, substituted cycloalkylene group, a heterocycloalkylene group, substituted heterocycloalkylene group, an arylene group, a substituted arylene group, and a combination thereof. Representative double hydrogen bonding catalysts of formula (13) include those listed in Table 7. In a specific embodiment, $R^2$ is an arylene or substituted arylene group, and the HFP groups occupy positions meta to each other on the aromatic ring.

TABLE 7

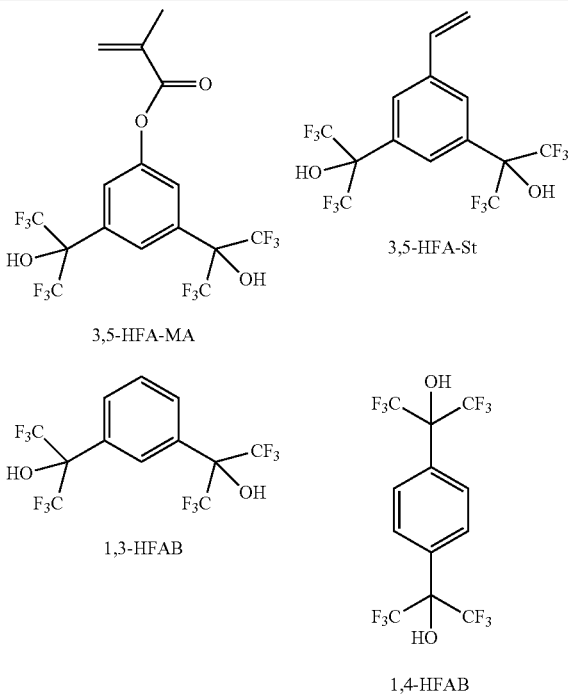

In one embodiment, the catalyst is selected from the group consisting of 4-HFA-St, 4-HFA-Tol, HFTB, NFTB, HPIP, 3,5-HFA-MA, 3,5-HFA-St, 1,3-HFAB, 1,4-HFAB, and combinations thereof.

Also contemplated are catalysts comprising HFP-containing groups bound to a support. In one embodiment, the support comprises a polymer, a crosslinked polymer bead, an inorganic particle, or a metallic particle. HFP-containing polymers can be formed by known methods including direct polymerization of an HFP-containing monomer (for example, the methacrylate monomer 3,5-HFA-MA or the styryl monomer 3,5-HFA-St). Functional groups in HFP-containing monomers that can undergo direct polymerization (or polymerization with a comonomer) include acrylate, methacrylate, alpha, alpha, alpha-trifluoromethacrylate, alpha-halomethacrylate, acrylamido, methacrylamido, norbornene, vinyl, vinyl ether, and other groups known in the art. Examples of linking groups include $C_1$-$C_{12}$ alkyl, a $C_1$-$C_{12}$ heteroalkyl, ether group, thioether group, amino group, ester group, amide group, or a combination thereof. Also contemplated are catalysts comprising charged HFP-containing groups bound by ionic association to oppositely charged sites on a polymer or a support surface.

The ROP reaction mixture comprises at least one organocatalyst and, when appropriate, several organocatalysts together. The ROP catalyst is added in a proportion of 1/20 to 1/40,000 moles relative to the cyclic carbonyl monomers, and preferably in a proportion of 1/1,000 to 1/20,000 moles relative to the cyclic carbonyl monomers.

ROP Accelerators.

The ROP polymerization can be conducted in the presence of an optional accelerator, in particular a nitrogen base. Exemplary nitrogen base accelerators are listed below and include pyridine (Py), N,N-dimethylaminocyclohexane (Me$_2$NCy), 4-N,N-dimethylaminopyridine (DMAP), trans 1,2-bis(dimethylamino)cyclohexane (TMCHD), 1,8-diazabicyclo[5.4.0]undec-7-ene (DBU), 1,5,7-triazabicyclo[4.4.0]dec-5-ene (TBD), 7-methyl-1,5,7-triazabicyclo[4.4.0]dec-5-ene (MTBD), (−)-sparteine, (Sp) 1,3-bis(2-propyl)-4,5-dimethylimidazol-2-ylidene (Im-1), 1,3-bis(2,4,6-trimethylphenyl)imidazol-2-ylidene (Im-2), 1,3-bis(2,6-di-1-propylphenyl(imidazol-2-ylidene (Im-3), 1,3-bis(1-adamantyl)imidazol-2-ylidene (Im-4), 1,3-di-1-propylimidazol-2-ylidene (Im-5), 1,3-di-t-butylimidazol-2-ylidene (Im-6), 1,3-bis(2,4,6-trimethylphenyl)-4,5-dihydroimidazol-2-ylidene (Im-7), 1,3-bis(2,6-di-1-propylphenyl)-4,5-dihydroimidazol-2-ylidene, 1,3-bis(2,6-di-1-propylphenyl)-4,5-dihydroimidazol-2-ylidene (Im-8) or a combination thereof, shown in Table 8.

TABLE 8

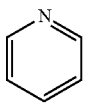

Pyridine
(Py)

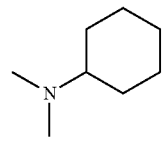

N,N-Dimethylaminocyclohexane
(Me$_2$NCy)

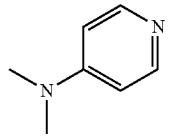

4-N,N-Dimethylaminopyridine
(DMAP)

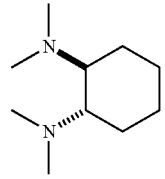

trans 1,2-Bis(dimethylamino)cyclohexane
(TMCHD)

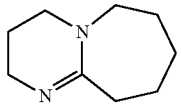

1,8-Diazabicyclo[5.4.0]undec-7-ene
(DBU)

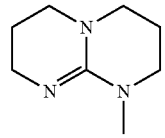

7-Methyl-1,5,7-triazabicyclo[4.4.0]dec-5-ene
(MTBD)

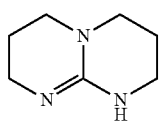

1,5,7-Triazabicyclo[4.4.0]dec-5-ene
(TBD)

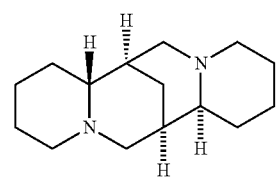

(−)-Sparteine
(Sp)

TABLE 8-continued

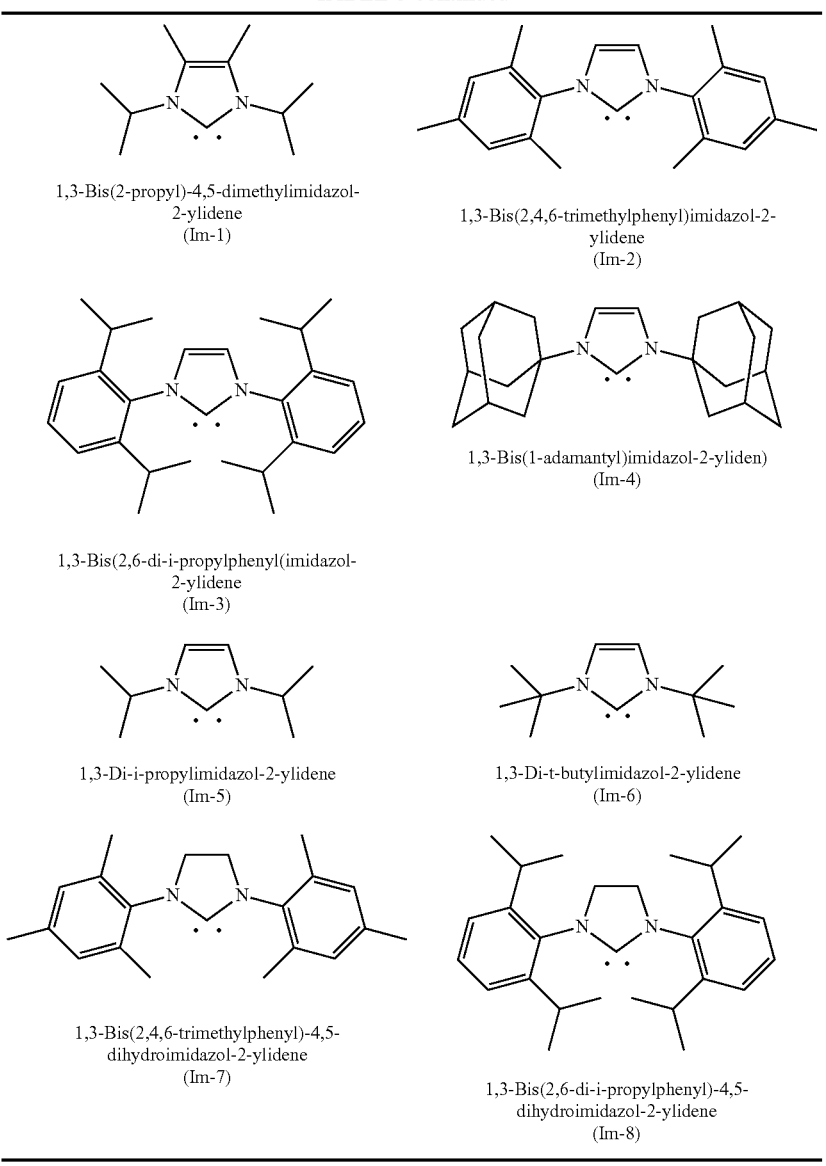

In an embodiment, the accelerator has two or three nitrogens, each capable of participating as a Lewis base, as for example in the structure (−)-sparteine. Stronger bases generally improve the polymerization rate.

The catalyst and the accelerator can be the same material. For example, some ring opening polymerizations can be conducted using 1,8-diazabicyclo[5.4.0]undec-7-ene (DBU) alone, with no another catalyst or accelerator present.

The catalyst is preferably present in an amount of about 0.2 to 20 mol %, 0.5 to 10 mol %, 1 to 5 mol %, or 1 to 2.5 mol %, based on total moles of cyclic carbonyl monomer.

The nitrogen base accelerator, when used, is preferably present in an amount of 0.1 to 5.0 mol %, 0.1 to 2.5 mol %, 0.1 to 1.0 mol %, or 0.2 to 0.5 mol %, based on total moles of cyclic carbonyl monomer. As stated above, in some instances the catalyst and the nitrogen base accelerator can be the same compound, depending on the particular cyclic carbonyl monomer.

The amount of initiator is calculated based on the equivalent molecular weight per nucleophilic initiator group in the dinucleophilic initiator. The initiator groups are preferably present in an amount of 0.001 to 10.0 mol %, 0.1 to 2.5 mol %, 0.1 to 1.0 mol %, and 0.2 to 0.5 mol %, based on total moles of cyclic carbonyl monomer. For example, if the molecular weight of the initiator is 100 g/mole and the initiator has 2 hydroxyl groups, the equivalent molecular weight per hydroxyl group is 50 g/mole. If the polymerization calls for 5 mol % hydroxyl groups per mole of monomer, the amount of initiator is 0.05×50=2.5 g per mole of monomer.

In a specific embodiment, the catalyst is present in an amount of about 0.2 to 20 mol %, the nitrogen base accelerator is present in an amount of 0.1 to 5.0 mol %, and the nucleophilic initiator groups of the initiator are present in an amount of 0.1 to 5.0 mol % based on the equivalent molecular weight per nucleophilic initiator group of the initiator.

The catalysts can be removed by selective precipitation or in the case of the solid supported catalysts, simply by filtration. The cationic triblock copolymer and/or the non-charged triblock copolymer can comprise residual catalyst in an amount greater than 0 wt. % (weight percent), based on total weight of the block copolymer and the residual catalyst. The amount of residual catalyst can also be less than 20 wt. %, less than 15 wt. %, less than 10 wt. %, less than 5 wt. %, less than 1 wt. %, or most specifically less than 0.5 wt. % based on the total weight of the block copolymer and the residual catalyst.
Average Molecular Weight.

The cationic triblock copolymer and/or the precursor triblock copolymer preferably have a number average molecular weight $M_n$ as determined by size exclusion chromatography of at least 1500 g/mol, more specifically 1500 g/mol to 1,000,000 g/mol, 4000 g/mol to 150000 g/mol, or 4000 g/mol to 50000 g/mol. In an embodiment, the cationic triblock copolymer and/or the precursor triblock copolymer has a number average molecular weight $M_n$ of 10,000 to 20,000 g/mole. The cationic triblock copolymer and/or the precursor triblock copolymer also preferably has a narrow polydispersity index (PDI), generally from 1.01 to 2.0, more particularly 1.01 to 1.30, and even more particularly 1.01 to 1.25.

The non-charged triblock copolymer preferably has a number average molecular weight $M_n$ as determined by size exclusion chromatography of at least 1500 g/mol, more specifically 1500 g/mol to 1,000,000 g/mol, 4000 g/mol to 150000 g/mol, and even more specifically 4000 g/mol to 50000 g/mol. In an embodiment, the non-charged triblock copolymer has a number average molecular weight $M_n$ of 10000 to 20000 g/mole. The non-charged triblock copolymer also preferably has a narrow polydispersity index (PDI), generally from 1.01 to 2.0, more particularly 1.01 to 1.30, and even more particularly 1.01 to 1.25.
Mixed Complexes.

In water, optionally containing a minimal amount of organic solvent (e.g., THF), the disclosed compositions self assemble to form a mixed complex. The mixed complex comprises the cationic triblock copolymer and the non-charged triblock copolymer bound by non-covalent interactions. The mixed complex is highly toxic to at least a Gram-negative microbe. The mixed complex can be a nanoparticle, such as a spherical micelle, or an elongated structure, such as a rod.

A method of preparing a mixed complex comprises forming a 0.001 wt. % to 60 wt. % aqueous mixture of the disclosed composition, based on total weight of the aqueous mixture.

Another method of preparing a mixed complex comprises i) forming an aqueous first mixture containing the cationic triblock copolymer (first polymer), the cationic triblock copolymer optionally comprising a first stereospecific repeat unit; forming an aqueous second mixture containing the non-charged triblock copolymer (second polymer) optionally comprising a second stereospecific repeat unit; and combining the first mixture and the second mixture, thereby forming a third mixture comprising the mixed complex. The mixed complex is an effective antimicrobial agent against at least a Gram-negative microbe. In an embodiment, the mixed complex is a more active antimicrobial agent against Gram-negative bacteria compared to the cationic triblock copolymer alone and the non-charged triblock copolymer alone when tested under otherwise identical conditions. The third mixture containing the mixed complex can have a low viscosity at ambient temperature (18° C. to 28° C.) and pH 4.5 to 8.0, forming a freely flowing liquid micelle solution at ambient temperature. Heating the micelle solution to 32° C. to 40° C. can produce a hydrogel. Alternatively, removing any organic solvent from the low viscosity micelle solution at ambient temperature can produce a hydrogel. In some instances, the micelle solution containing no organic solvent is a freely flowing liquid micelle solution at ambient temperature and pH 4.5 to 8.0, which forms a hydrogel when heated to 32° C. to 40° C.

In the absence of organic solvent, the non-charged triblock copolymer alone can form a hydrogel in water at ambient temperature and at a concentration of about 1% w/v (weight to volume of solvent) or more, and more particularly about 5% w/v to about 10% w/v. The hydrogel can contain rod-like structures. An aqueous mixture that includes the non-charged triblock copolymer and no cationic triblock copolymer can have a low toxicity or no toxicity toward a Gram-negative microbe compared to a control buffer solution (e.g., PBS) containing no polymer.

The cationic triblock copolymer alone typically does not form a hydrogel alone in water at a temperature from 1° C. to 40° C. and a concentration of 1% w/v or more, or more particularly at a concentration of about 5% w/v to about 10 wt. %. Additionally, an aqueous mixture that includes the cationic triblock copolymer but no non-charged triblock copolymer can have a low toxicity or no toxicity toward a Gram-negative microbe compared to a control solution (e.g., PBS) that contains no polymer.

However, the mixed complex that includes the cationic triblock copolymer and the non-charged triblock copolymer surprisingly can be highly toxic to at least a Gram-negative microbe.

The mixed complex having enhanced toxicity toward a Gram-negative microbe contains more than 0 wt. % of the cationic triblock copolymer and more than 0 wt. % of the non-charged triblock copolymer. The optimum weight ratio of the cationic triblock copolymer and non-charged triblock copolymer for mixed complex formation in water can depend on the molecular weight of the hydrophilic and hydrophobic blocks, the charge density of the hydrophilic block of the cationic triblock copolymer, and optionally the content of the stereospecific repeat unit of the hydrophobic blocks, which one of skill can readily determine for a specific combination of triblock copolymers.

For example, when the hydrophobic blocks of the cationic triblock copolymer have a similar hydrophobicity and chain length compared to the hydrophobic blocks of the non-charged triblock copolymer, in general the mixed complex preferably comprises the cationic triblock copolymer and the non-charged triblock copolymer in a weight ratio, respectively, of about 0.25:10 w/w to about 3:2 w/w, about 0.25:10 w/w to about 5.5:4.5 w/w, about 0.25:10 w/w to about 1:1 w/w, about 0.5:10 w/w to about 1:1 w/w, about 1.0:10 w/w to about 1:1 w/w, about 2:3 w/w to 3:2 w/w, or about 1:1 w/w. Under these conditions, a 1:1 weight ratio of the cationic triblock copolymer and the non-charged triblock copolymer is favorable for hydrophobic and/or stereocomplexation of the hydrophobic chain segments to form a mixed complex by non-covalent interactions.

When the hydrophobic blocks of the cationic triblock copolymer differ in hydrophobicity and/or chain length compared to the hydrophobic blocks of the non-charged triblock copolymer, the weight ratio of hydrophobic blocks of the cationic triblock copolymer to hydrophobic blocks of non-charged triblock copolymer in the mixed complex, given the empirical observation that stereocomplexation is most favored between, for example, poly(L-lactide) (PLLA) blocks and poly(D-lactide) (PDLA) blocks at a weight ratio of 1:1 w/w. The mixed complex preferably comprises a weight ratio of hydrophobic blocks of the cationic triblock copolymer to hydrophobic blocks of the non-charged triblock copolymer of about 0.25:10 w/w to about 3:2 w/w, about 2:3 w/w to about 3:2 w/w, or about 1:1 w/w.

The concentration of the mixed complex comprising the cationic triblock copolymer and the non-charged triblock copolymer in the micelle solution or hydrogel, is more than 0 wt. %, based on total weight of the micelle solution or the hydrogel. Preferably, the concentration of the mixed complex in the micelle solution or hydrogel is about 0.001 wt. % to about 60 wt. %, 1.0 wt. % to about 60 wt. %, about 1.0 wt. % to about 30 wt. %, about 1 wt. % to about 20 wt. %, about 5 wt. % to about 15 wt. %, about 5 wt. % to about 12 wt. %, or about 8 wt. % to about 12 wt. % based on total weight of the micelle solution or the hydrogel. A method comprises i) forming a first mixture with minimal organic solvent and the remaining water comprising the cationic triblock copolymer; ii) forming a second mixture with a minimal amount of organic solvent and the remaining water comprising of the non-charged triblock copolymer, and iii) combining the first mixture and the second mixture, thereby forming a micelle solution. The method can further comprise removing any organic solvent present, thereby forming a hydrogel. The method can further comprise heating the micelle solution to a temperature of 32° C. to 40° C., thereby forming a hydrogel.

As shown in the examples below, a hydrogel can be prepared using a 1:1 weight ratio of the cationic triblock copolymer to the non-charged triblock copolymer at a concentration of the mixed complex of about 5% w/v to about 12% w/v in water. This is not expected based on the charge density of the mixed complex.

Nanoparticulate micelles formed by the cationic triblock copolymer alone, non-charge triblock copolymer alone, or mixed complex before gelation preferably have an average particle size of 10 nm to 500 nm, 10 nm to 250 nm, and more particularly 50 nm to 200 nm as measured by dynamic light scattering. For the foregoing particle sizes, the aqueous solution preferably has a pH of 4.5 to 8.0, 5.0 to 7.0, or 6.0 to 7.0.

The micelle solution and/or the hydrogel can contain a mixed complex in the form of rods. The rods can have an approximate diameter of about 100 nm to about 500 nm and an approximate length of about 0.5 micrometers to about 50 micrometers.

The organic solvent used to form a mixed complex is preferably soluble in water at concentrations of 1 microliter or more of organic solvent per 100 microliters of water. Exemplary organic solvents include methanol, ethanol, propanol, 2-propanol, 1-butanol, 2-butanol, t-butyl alcohol, acetone, 2-butanone, dimethoxyethane, diglyme, diethyl ether, methyl t-butyl ether, methylene chloride, ethyl acetate, ethylene glycol, glycerin, dimethylsulfoxide, dimethylformamide, acetic acid, tetrahydrofuran (THF), and dioxane. The water:organic solvent ratio is preferably 99.9:0.1 v/v to 90:10 v/v (by volume).

Industrial Applicability.

Hydrogels have found widespread application in the field of medicine particularly in wound healing, regenerative medicine, and decolonization of MRSA or other types of microbes. Moreover, the ability to deposit from solution and have the gel formation be triggered by an external stimulus such as temperature is highly desirable for ease of application. The disclosed hydrogel forming materials can incorporate many types of chemical functionality heretofore unavailable in biodegradable hydrogel forming materials, providing a wider range of applications for these materials.

Without being bound by theory, the hydrogel forming capability of disclosed compositions comprising the cationic triblock copolymer and the non-charged triblock copolymer in water is attributed to the amphiphilicity of the two block copolymers, and is further assisted by optional stereospecificity of hydrophobic blocks of each of the two block copolymers, which favor non-covalent stereocomplexation between hydrophobic chain segments of the two block copolymers to form a gel network. The DNA binding activity of the composition is attributed primarily to the cationic hydrophilic block of the cationic block copolymer. The antimicrobial activity of the compositions toward Gram-positive microbes can also be attributed to the cationic charge density. However, the unusual superadditive effect of the compositions against Gram-negative microbes cannot be explained by charge density alone, by stereospecificity alone, or hydrogel formation alone. Without being bound by theory, the superadditive toxicity of the mixed complex toward Gram-negative microbes perhaps involves a particular morphology of the mixed complex having a favored and lethal interaction with the Gram-negative microbial membrane which might or might not include the supermolecular structure of the hydrogel itself. On the other hand, it might also be possible that the superadditive effect is due to the combination of charge density, stereospecificity, hydrophobicity and hydrogel formation.

The mixed complexes can also help mitigate unwanted protein adsorption relative to the cationic material alone.

Wound Healing.

Dressings for wound healing have become an important area of research particularly for the treatment of burns, battlefield injuries, surgical and diabetic wounds, and other injuries. The dressing must be designed to prevent loss of fluids, mitigate bacterial infection and accelerate tissue regeneration. The material requirements for such a dressing are stringent and include gas permeability, mechanical integrity and the ability to control water uptake/loss. The dressing should be easy to apply, cure or set rapidly, and adhere to the desired substrate. The dressing should show no systemic toxicity, should be comfortable, and should be easy to remove without damaging underlying tissue. The most commonly used wound dressings are gauze that tends to become trapped in the nascent tissue making the eventual removal difficult and painful. Dressings that have to be changed frequently often remove epithelial cells that have proliferated and migrated to the dressing material causing secondary damage to the wound. One important feature of the disclosed compositions is that the formation of hydrogels can be rapid without using a catalyst and solvent. Therefore, the hydrogel can be formed in situ. This allows for easy application in wound managements by simply spraying the hydrogel forming aqueous mixture of the composition onto wounds (e.g., a first aid treatment for burns, the hydrogel forming a temporary "skin" that inhibits fluid loss and infection). The hydrogels also allow for encapsulation of cells such as human dermal fibroblasts or keratinocytes to accelerate the wound healing process. Moreover, the hydrogels can be thermosensitive. At the body temperature, the disclosed compositions can form a hydrogel, which can dissolve at lower temperatures. Therefore, the hydrogels can be easily removed by washing with cold water after wounds are healed. On the other hand, the hydrogels are formed based on physical interactions and aggregation of mixed complexes (e.g., micelles). Therefore, the hydrogels can be easily removed by washing with an aqueous solution. Furthermore, the disclosed hydrogels can be substantially or wholly biodegradable. Therefore, they can be used for healing of various types of wounds in any part of the body.

Another critical component to a wound-dressing design is the ability to fight bacterial infection. Due to the increasing resistance of bacteria to conventional antibiotics, macromolecular peptide-based antimicrobial agents have received significant attention. Cationic peptides (e.g., magainins, cecropins, protegrins and defensins) do not have a specific target in microbes, and they interact with microbial membranes based on electrostatic interaction, thereby inducing damage to the microbial membranes, which is hard to repair.

The disclosed hydrogels contain cationic triblock copolymers that can inhibit growth of microbes. Therefore, they can also be used for prevention and treatment of infections caused by drug-resistant microbes such as methicillin-resistant *Staphylococcus aureus* (MRSA). For example, the hydrogel forming compositions can be sprayed onto the nares (front parts of the nose), or onto central venous catheter surface to form antimicrobial hydrogels for preventing MRSA infections. These applications are important as one-third population of the world carries MRSA colonies in the nares. Currently in the clinical settings, mupirocin ointment is used for 5 days (accompanied with a chlorhexidine wash daily) to decolonize *Staphylococcus aureus* (and MRSA) carriage. However, mupirocin resistance is creeping up worldwide. In addition, a central venous catheter is widely used in many patients who have chronic diseases. To prevent infections of the catheter, chlorhexidine-impregnated disk or sponge that is slipped over the central catheter during insertion is used, which lasts for about a week. However, chlorhexidine is a small molecular antibiotic, and chlorhexidine resistance in bacteria has been reported.

Regenerative Medicine.

The past decade has seen a surge of interest in using stem cells to regenerate diseased or damaged tissues. The defining features of stem cells make them a potentially invaluable source for cell therapy in many pathologies, but clinical use is predicated on finding ways to reliably differentiate stem cell populations into desired phenotypes. Without such direction, implanted stem cells form bodies of heterogeneous cell types that could degenerate into tumors. Recent advances in stem cell biology have revealed many of the biochemical and biophysical cues that regulate stem cell proliferation and differentiation in vivo, and this knowledge has in turn spurred the design of artificial culture platforms capable of both nurturing and directing the fate of stem cells.

Hydrogels are the most extensively studied platforms because their 3D nature and high water content most resemble the native extracellular matrix (ECM) that surrounds many types of stem cells. Synthetic hydrogels are superior to natural gels as they offer greater control of gel physical properties as well as the chemical composition and overall architecture of the gel. In particular, the disclosed compositions which utilize a bio-inert PEG can prevent non-specific protein adhesion, thus reducing immune and inflammatory responses, while on the other hand, the remarkable versatility of PEG macromer chemistry facilitates the incorporation of chemical and physical cues for stem cell adhesion and controlled differentiation. Another important design feature is the ability of the disclosed compositions to bind and deliver genetic material to promote cell differentiation. Gene delivery requires that the gel be charged to facilitate the binding of genetic material. Moreover, it is desirable that the gel change with and accommodate the growth of tissue. Therefore it is desirable to have a degradable gel that is not only protein resistant but also able to bind genetic material and incorporate cells, and be capable of remodeling itself as tissue grows. The disclosed compositions provide these capabilities.

The examples below demonstrate that compositions comprising a cationic triblock copolymer and a non-charged triblock copolymer have strong antimicrobial activity against Gram-negative microbes, such as *Escherichia Coli*, and Gram-positive microbes, such as *Staphylococcus aureus*, fungi, and yeast. In an embodiment, a method comprises contacting a microbe with the composition, thereby killing the microbe.

The compositions are attractive as antimicrobial agents that can be applied to animal tissue, which include human and/or other animal tissues, mammalian and/or non-mammalian tissues. The general term "animal tissue" includes wound tissue, burn tissue, skin, internal organ tissue, blood, bones, cartilage, teeth, hair, eyes, nasal surfaces, oral surfaces, other body cavity surfaces, and any cell membrane surfaces. In an embodiment, a method comprises contacting an animal tissue with the composition. In another embodiment, a method comprises contacting an animal tissue with an aqueous mixture of the composition.

The antimicrobial compositions are also attractive as disinfecting agents for surfaces of articles (i.e., non-living articles) such as, for example, building surfaces in homes, businesses, and particularly hospitals. Exemplary home and commercial building surfaces include floors, door surfaces, bed surfaces, air conditioning surfaces, bathroom surfaces, railing surfaces, kitchen surfaces, and wall surfaces. Other articles include medical devices, cloths, garments, and non-medical equipment. Surfaces of articles can comprise materials such as wood, paper, metal, cloth, plastic, rubber, glass, paint, leather, or combinations thereof. In an embodiment, a method comprises contacting a surface of an article with the composition. In another embodiment, a method comprises contacting a surface of an article with an aqueous mixture of the composition.

The antimicrobial compositions can be used in the form of a powder, a pill, or an aqueous mixture in the form a freely flowing liquid, spray solution, a cream, a hydrogel, or a liquid that transforms into a hydrogel after contact with animal tissue or article surface. Uses include disinfectant washes for hands, skin, hair, bone, ear, eye, nose, throat, internal tissue, wounds, and teeth (e.g., as a mouthwash). Still other uses include disinfectants for articles such as medical devices. Medical devices include swabs, catheters, sutures, stents, bedpans, gloves, facial masks, absorbent pads, absorbent garments, internal absorbent devices, and insertable mechanical devices. In an embodiment, an article comprises a medical device in contact with the composition.

The composition comprising a cationic triblock copolymer and a non-charged triblock copolymer can be used as a drug. The drug can be administered as a powder, a pill, a liquid solution, or a hydrogel. The drug can be administered orally or by way of other body cavities, by injection, intravenously, and/or topically.

Loaded Complexes.

The compositions comprising the cationic triblock copolymer and the non-charged triblock copolymer can form loaded complexes (polyplexes) with negatively charged biologically active materials such as genes, nucleotides, proteins, peptides, other drugs, or a combination thereof. In an embodiment, the biologically active material is a negatively charged genetic material. In another embodiment, the biologically active material is a drug other than the composition itself. The loaded complex can be used as a drug. The loaded complex can be administered as a powder, a pill, a liquid solution, or a hydrogel. The loaded complex can be administered orally or by way of other body cavities, by injection, intravenously, and/or topically.

A method of preparing a loaded complex for treating a cell comprises i) forming a first mixture in water of the cationic triblock copolymer; ii) forming a second mixture with minimal organic solvent and the remaining water comprising the non-charged triblock copolymer; iii) forming a third mixture comprising a negatively charged biologically active material in water; iv) combining the first, second and third mixtures in a suitable order, thereby forming a fourth mixture comprising the loaded complex; and v) optionally removing any organic solvent present. In an embodiment, the fourth mixture is a liquid comprising the loaded complex. In an embodiment, the fourth mixture is a hydrogel comprising the loaded complex. In another embodiment, the method further comprises drying the loaded complex, thereby forming a biologically active powder, which can be redispersed in water. In another embodiment, the method further comprises heating the fourth mixture in water to a temperature of 32° C. to 40° C. at a pH of from 4.5 to 8.0, thereby forming a hydrogel comprising the loaded complex.

A method of treating a cell comprises contacting the cell with an aqueous mixture comprising a loaded complex, the loaded complex comprising i) a cationic triblock copolymer, ii) a non-charged triblock copolymer, and iii) a negatively charged biologically active material, the aqueous mixture having a pH of from 4.5 to 8.0. In an embodiment, the negatively charged biologically active material is a gene. The cells can be exposed to the loaded complex in vitro, ex vivo and then subsequently placed into an animal, or in vivo (for example, an animal or human). In another embodiment, the negatively charged biologically active material is a molecular drug or a protein. In another embodiment, the loaded complex induces no hemolysis. In another embodiment, the loaded complex has no cytotoxicity.

Exemplary commercially available drugs include 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Cisplatin, Citrovorum Factor, Cladribine, Cortisone, Cosmegen®, CPT-11, Cyclophosphamide, Cytadren®, Cytarabine, Cytarabine Liposomal, Cytosar-U®, Cytoxan®, Dacarbazine, Dacogen, Dactinomycin, Darbepoetin Alfa, Dasatinib, Daunomycin, Daunorubicin, Daunorubicin Hydrochloride, Daunorubicin Liposomal, DaunoXome®, Decadron, Decitabine, Delta-Cortef®, Deltasone®, Denileukin Diftitox, DepoCyt™, Dexamethasone, Dexamethasone Acetate, Dexamethasone Sodium Phosphate Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar, Gleevec™, Gliadel® Wafer, GM-CSF, Goserelin, Granulocyte-Colony Stimulating Factor, Granulocyte Macrophage Colony Stimulating Factor, Halotestin®, Herceptin®, Hexadrol, Hexylen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan Idamycin®, Idarubicin, Ifex®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, K Kidrolase (t), Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™ Methotrexate, Methotrexate Sodium, Methylprednisolone, Meticorten®, Mitomycin, Mitomycin-C, Mitoxantrone, M-Prednisol®, MTC, MTX, Mustargen®, Mustine Mutamycin®, Myleran®, Mylocel™, Mylotarg®, Navelbine®, Nelarabine, Neosar®, Neulasta™, Neumega®, Neupogen®, Nexavar®, Nilandron®, Nilutamide, Nipent®, Nitrogen Mustard, Novaldex®, Novantrone®, Octreotide, Octreotide acetate, Oncospar®, Oncovin®, Ontak®, Onxal™, Oprevelkin, Orapred®, Orasone®, Oxaliplatin, Paclitaxel, Paclitaxel Protein-bound, Pamidronate, Panitumumab, Panretin®, Paraplatin®, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a) Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, VP-16, Vumon®, Xeloda®, Zanosar®, Zevalin™, Zinecard®, Zoladex®, Zoledronic acid, Zolinza, and Zometa.

Any cell that can be transfected by a non-viral vector can be treated with the above-described loaded complexes. In particular the cells are eukaryotic cells, mammalian cells, and more particularly rodent or human cells. The cells can be derived from various tissues, including extraembryonic or embryonic stem cells, totipotent or pluripotent, dividing or non-dividing, parenchyma or epithelium, immortalized or transformed, or the like. The cell can be a stem cell or a differentiated cell. Cell types that are differentiated include adipocytes, fibroblasts, myocytes, cardiomyocytes, endothelium, dendritic cells, neurons, glia, mast cells, blood cells and leukocytes (e.g., erythrocytes, megakaryotes, lymphocytes, such as B, T and natural killer cells, macrophages, neutrophils, eosinophils, basophils, platelets, granulocytes), epithelial cells, keratinocytes, chondrocytes, osteoblasts, osteoclasts, hepatocytes, and cells of the endocrine or exocrine glands, as well as sensory cells.

The above-described loaded complexes can be used as non-viral transfection vectors. The target gene is not limited to any particular type of target gene or nucleotide sequence. For example, the target gene can be a cellular gene, an endogenous gene, an oncogene, a transgene, a viral gene, or translated and non-translated RNAs. Exemplary possible target genes include: transcription factors and developmental genes (e.g., adhesion molecules, cyclin-dependent kinase inhibitors, Wnt family members, Pax family members, Winged helix family members, Hox family members, cytokines/lymphokines and their receptors, growth/differentiation factors and their receptors, neurotransmitters and their receptors); oncogenes (e.g., ABLI, BCLI, BCL2, BCL6, CBFA2, CBL, CSFIR, ERBA, ERBB, ERBB2, ETSI, ETV6, FGR, FOS, FYN, HCR, HRAS, JUN, KRAS, LCK, LYN, MDM2, MLL, MYB, MYC, MYCLI, MYCN, NRAS, PIMI, PML, RET, SKP2, SRC, TALI, TCL3, and YES); tumor suppressor genes (e.g., APC, BRAI, BRCA2, CTMP, MADH4, MCC, NFI, NF2, RBI, TP53, and WTI); and enzymes (e.g., ACP desaturases and hydroxylases, ADP-glucose pyrophorylases, ATPases, alcohol dehydrogenases, amylases, amyloglucosidases, catalases, cyclooxygenases, decarboxylases, dextrinases, DNA and RNA polymerases, galactosidases, glucose oxidases, GTPases, helicases, integrases, insulinases, invertases, isomerases, kinases, lactases, lipases, lipoxygenases, lysozymes, peroxidases, phosphatases, phospholipases, phosphorylases, proteinases and peptidases, recombinases, reverse transcriptases, telomerase, including RNA and/or protein components, and topoisomerases).

Charge Shifting

The release of a biologically active material can be facilitated by cationic polymers capable of charge-shifting. In charge shifting, the net positive charge of the cationic triblock copolymer is reduced by the conversion of a non-charged group on the cationic triblock copolymer side chain into a negatively charged group after the loaded complex has entered the cell. A cationic polymer capable of charge-shifting can comprise, for example, a latent carboxylic acid group, such as an acetal ester, in addition to the quaternary amine. The acetal ester group has the general formula (14):

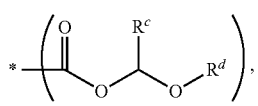

(14)

wherein the starred bond represents the attachment point to a cyclic carbonyl moiety, and $R^c$ and $R^d$ are monovalent radicals independently comprising from 1 to 20 carbons. In an embodiment, $R^c$ is methyl and $R^d$ is ethyl. In another embodiment, a diluent cyclic carbonyl monomer is MTCOEE:

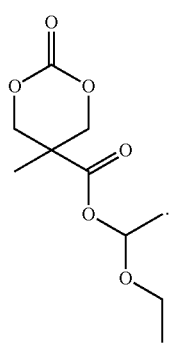

(MTCOEE)

Acetal esters can be hydrolyzed under the mildly acidic conditions of the endosomal environment (about pH 5) to form a carboxylic acid group. In the more basic environment of the cytosol, the carboxylic acid groups become ionized, thereby lowering the net positive charge of the cationic triblock copolymer and allowing the release of the negatively charged biologically active material. Thus, the cationic triblock copolymers can be easily modified to tune the charge and the buffering strength for a specific biologically active material.

Another strategy for facilitating endosomal release involves non-covalent interactions to stabilize a biologically active cargo, for example, using diluent cyclic carbonyl monomers comprising a fluorinated tertiary alcohol group. Fluorinated tertiary alcohol groups are known to bind to phosphates and related structures, but with interaction energies that are lower than electrostatic interactions, and hence more easily released.

Other functional groups can be used to facilitate the release of the biologically active material from the loaded complex, such as secondary amine groups, citraconic amide groups, ester groups, and imine groups.

The following examples demonstrate the preparation and uses of the disclosed antimicrobial compositions comprising cationic triblock copolymers and non-charged triblock copolymers produced by organocatalytic ring-opening polymerization.

EXAMPLES

Materials used in the following examples are listed in Table 9.

TABLE 9

| ABBRE-VIATION | DESCRIPTION | SUPPLIER |
|---|---|---|
| PEG1 | Poly(ethylene glycol) (Mn 6000) | Fluka |
| PEG2 | Poly(ethylene glycol) (Mn 8000) | Fluka |
| TU | N-(3,5-bis(trifluoromethyl)-phenyl)-3-cyclohexyl-2-thiourea | |
| DLA | D-Lactide | Aldrich |
| LLA | L-Lactide | Aldrich |
| DBU | 1,8-diazabicyclo[5,4,0]undec-7-ene | Aldrich |
| b-CD | Beta Cyclodextrin | Aldrich |

PEG1, having a number average molecular weight (Mn) of 6000 g/mol, and PEG2, Mn 8000 g/mol (MPEG2), obtained from Fluka, were azeotropically distilled and recrystallized from toluene prior to use. Sparteine was distilled from calcium hydride prior to use. Dry THF and $CH_2Cl_2$ were obtained by using a solvents drying system from Innovative.

N-(3,5-trifluoromethyl)phenyl-N'-cyclohexyl-thiourea (TU) was prepared as reported by R. C. Pratt, B. G. G. Lohmeijer, D. A. Long, P. N. P. Lundberg, A. Dove, H. Li, C. G. Wade, R. M. Waymouth, and J. L. Hedrick, Macromolecules, 2006, 39 (23), 7863-7871, and dried by stirring in dry THF over $CaH_2$, filtering, and removing solvent under vacuum.

Monomer Syntheses.

Cyclic carbonate monomers were prepared from 2,2-bis(methylol)propionic (BisMPA) according to Scheme 1.

Scheme 1.

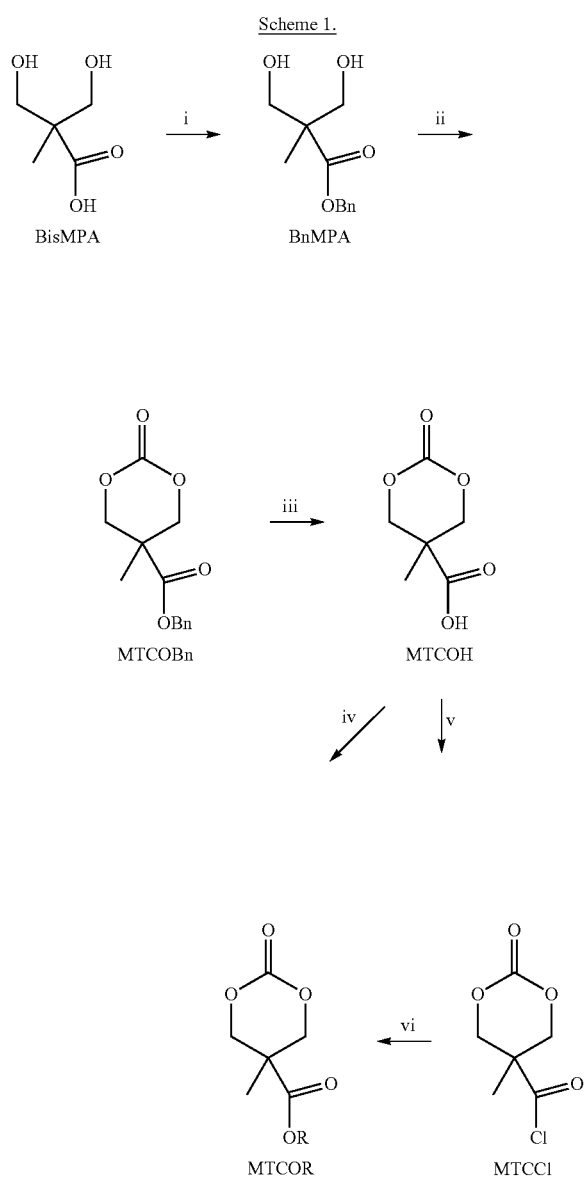

BisMPA can be converted (i) to the benzyl ester BnMPA using known methods. Reaction of BnMPA with triphosgene (ii) produces cyclic carbonyl monomer, MTCOBn. Debenzylation of MTCOBn (iii) produces 5-methyl-5-carboxyl-1,3-dioxan-2-one (MTCOH). Two pathways are shown for forming an ester from MTCOH. In the first pathway, (iv), MTCOH is treated with a suitable carboxy activating agent, such as dicyclohexylcarbodiimide (DCC), which reacts with ROH to form MTCOR in a single step. Alternatively, MTCOH can be converted first (v) to the acid chloride MTCC1 followed by treatment (vi) of MTCC1 with ROH in the presence of a base to form MTCOR. Both pathways are illustrative and are not meant to be limiting. The following conditions are typical for the reactions shown in Scheme 1: (i) Benzylbromide (BnBr), KOH, DMF, 100° C., 15 hours, 62% yield of the benzyl ester of bisMPA; (ii) triphosgene, pyridine, $CH_2Cl_2$, −78° C. to 0° C., 95% yield of MTCOBn; (iii) Pd/C (10%), $H_2$ (3 atm), EtOAc, room temperature, 24 hours, 99% yield of MTCOH; (iv) ROH, DCC, THF, room temperature, 1 to 24 hours; (v) $(COCl)_2$, THF, room temperature, 1 hour, 99% yield of MTCC1; (vi) ROH, $NEt_3$, RT, 3 hours yields MTCOR.

Preparation of 5-methyl-5-(3-chloropropyl)oxycarboxyl-1,3-dioxan-2-one, (MTCOPrCl), MW 236.65

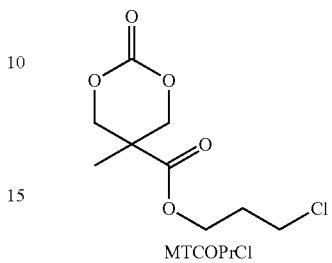

MTCOPrCl

A catalytic amount (3 drops) of DMF was added to a THF solution (200 mL) of MTCOH (11.1 g, 69 mmol), followed by a solution of oxalyl chloride (7.3 mL, 87 mmol) in THF (100 mL), gently added over 20 min under $N_2$ atmosphere. The solution was stirred for 1 hour, bubbled with $N_2$ flow to remove volatiles, and evaporated under vacuum to give the intermediate MTCC1. A mixture of 3-chloro-1-propanol (5.4 mL, 76 mmol) and pyridine (6.2 mL, 65 mmol) in dry THF (50 mL) was added dropwise to a dry THF solution (100 mL) of MTCC1 over 30 min, while maintaining a solution temperature below 0° C. with an ice/salt bath. The reaction mixture was kept stirring for another 3 hours at room temperature before it was filtered and the filtrate evaporated. The residue was dissolved in methylene chloride and washed with 1N HCl aqueous solution, saturated $NaHCO_3$ aqueous solution, brine and water, stirred with $MgSO_4$ overnight, and the solvent evaporated. The crude product was passed through a silica gel column by gradient eluting of ethyl acetate and hexane (50/50 to 80/20) to provide the product as a colorless oil that slowly solidified to a white solid (9.8 g, 60%).

Preparation of 5-methyl-5-(3-bromopropyl)oxycarboxyl-1,3-dioxan-2-one, (MTCOPrBr), MW 281.10

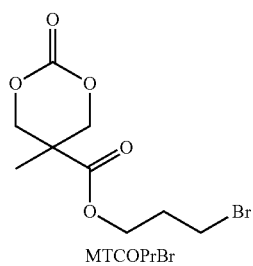

MTCOPrBr

MTCOPrBr was prepared by the procedure of Example 1 on a 45 mmol scale using 3-bromo-1-propanol as the alcohol. The product was purified by column chromatography, and subsequently recrystallized to yield white crystals (6.3 g, 49%). $^1H$ NMR (400 MHz, $CDCl_3$): delta 4.69 (d, 2H; $CH_2OCOO$), 4.37 (t, 2H; $OCH_2$), 4.21 (d, 2H; $CH_2OCOO$), 3.45 (t, 2H; $CH_2Br$), 2.23 (m, 2H; $CH_2$), 1.33 (s, 3H; $CH_3$). $^{13}C$ NMR (100 MHz, $CDCl_3$): delta 171.0, 147.3, 72.9, 63.9, 40.2, 31.0, 28.9, 17.3.

The corresponding iodopropyl cyclic carbonyl monomer compound can be prepared by substituting 3-chloro-1-propanol with 3-iodo-1-propanol in the procedure of Example 1.

Examples 1 to 16

Typical Synthesis of Non-Charged Triblock Copolymers

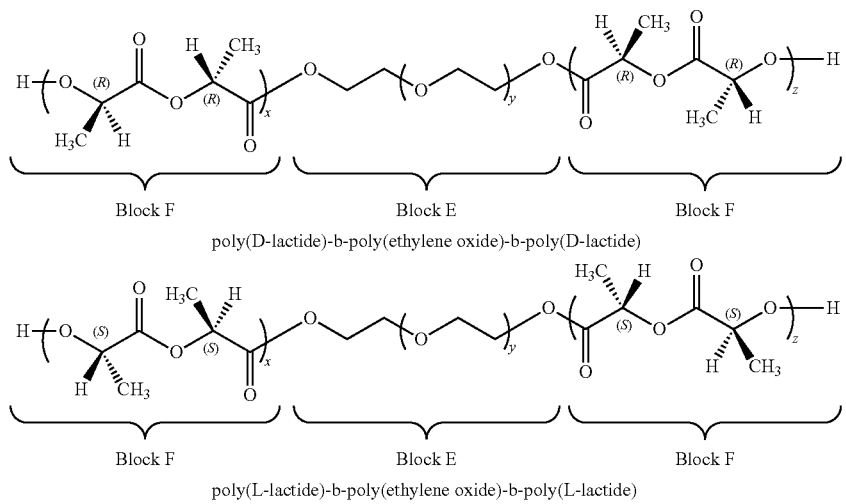

poly(D-lactide)-b-poly(ethylene oxide)-b-poly(D-lactide)

poly(L-lactide)-b-poly(ethylene oxide)-b-poly(L-lactide)

These triblock copolymers were prepared via organocatalytic ring-opening polymerization (ROP). The poly(ethylene oxide) blocks, which in the following examples have a number average molecular weight of 10,000 or lower, are biocompatible but are not enzymatically biodegradable. The poly(lactide) blocks are biocompatible and enzymatically biodegradable. Diol functional poly(ethylene glycol) oligomer having a number average molecular weight (Mn) 6000 g/mol (PEG1) or 8000 g/mol (PEG2) was used as initiator for the ROP of either L-lactide or D-lactide using a mixture of the Lewis acid N-(3,5-bis(trifluoromethyl)-phenyl)-3-cyclohexyl-2-thiourea (TU) and sparteine as catalysts in methylene chloride. As an example, PEG2 oligomer (Mn=8K, 0.40 g, 0.05 mmol) was dissolved in 2 ml of methylene chloride. In a separate vial, D-lactide (0.20 g, 1.38 mmol) was charged along with catalysts TU (0.025 g, 0.007 mol) and sparteine (0.016 g, 0.007 mol), and dissolved in methylene chloride. The D-lactide solution was added to the PEG2 initiator solution and the polymerization was followed for 6 hours by $^1$H NMR, at which time the D-lactide consumption was complete. The product was precipitated in ether, isolated by filtration, and dried. The non-charged triblock copolymer was characterized by $^1$H NMR and GPC.

Table 10 summarizes the results for Examples 1 to 16.

TABLE 10

| Example | Non-charged Triblock Copolymer Name | Lactide Isomer | PEG Oligomer (KDalton/mol) | Each PLA block (KDalton/mol) | Mn g/mol (GPC) | Polydispersity Index (PDI) |
|---|---|---|---|---|---|---|
| 1 | PEG2D20 | D | PEG2 (8.0) | 2.0 | 14000 | 1.07 |
| 2 | PEG2L20 | L | PEG2 (8.0) | 2.0 | 15000 | 1.08 |
| 3 | PEG2D15 | D | PEG2 (8.0) | 1.5 | 10900 | 1.05 |
| 4 | PEG2L15 | L | PEG2 (8.0) | 1.5 | 10900 | 1.04 |
| 5 | PEG2D10 | D | PEG2 (8.0) | 1.0 | 9750 | 1.05 |
| 6 | PEG2L10 | L | PEG2 (8.0) | 1.0 | 9750 | 1.04 |
| 7 | PEG1D20 | D | PEG1 (6.0) | 2.0 | 8900 | 1.03 |
| 8 | PEG1L20 | L | PEG1 (6.0) | 2.0 | 9000 | 1.04 |
| 9 | PEG1D15 | D | PEG1 (6.0) | 1.5 | 8400 | 1.04 |
| 10 | PEG1L15 | L | PEG1 (6.0) | 1.5 | 8500 | 1.05 |
| 11 | PEG1D10 | D | PEG1 (6.0) | 1.0 | 16000 | 1.05 |
| 12 | PEG1L10 | L | PEG1 (6.0) | 1.0 | 11000 | 1.05 |
| 13 | PEG1L85 | L | PEG1 (6.0) | 0.85 | 9000 | 1.06 |
| 14 | PEG1L12 | L | PEG1 (6.0) | 1.2 | 10700 | 1.05 |
| 15 | PEG1L14 | L | PEG1 (6.0) | 1.4 | 16300 | 1.05 |
| 16 | PEG1L16 | L | PEG1 (6.0) | 1.6 | 16500 | 1.05 |

Preparation of Precursor Polycarbonate Triblock Copolymers.

The precursor triblock copolymers were prepared by sequential ring-opening polymerizations of a first cyclic carbonate monomer bearing a pendant haloester group to form the precursor core block, followed by polymerization of D-lactide or L-lactide to form the peripheral hydrophobic blocks. The initiator was a diol, BnMPA. The polymerization was catalyzed by organocatalysts N-(3,5-trifluoromethyl) phenyl-N'-cyclohexyl-thiourea (TU) and 1,8-diazabicyclo[5,4,0]undec-7-ene (DBU) in methylene chloride at room temperature (1 to 2 hours).

Two distinctive precursor triblock copolymers were synthesized, one having L-stereocenters in the backbone of the peripheral blocks and a second having D-stereocenters in the backbone of the peripheral blocks. The core block of the precursor triblock copolymer is a polycarbonate having a haloalkyl ester side chain that can be readily quaternized.

Example 17

Precursor Triblock Copolymer I (Precursor I)

MTCOPrCl (365 mg, 1.54 mmol), BnMPA (22.2 mg, 0.10 mmol), and TU (14.5 mg, 0.039 mmol) were dissolved in methylene chloride (1.0 mL), and this solution was transferred to a vial containing DBU (6.0 mg, 0.039 mmol) to start polymerization at room temperature ([MTCOPrCl]$_0$/[I]$_0$=16). After 5 hours (conversion of MTCOPrCl ~93% to form PMTCCl), the solution was transferred to a vial containing D-lactide (DLA) (261 mg, 1.81 mmol) to start the second polymerization. The second polymerization was stirred for 19 hours at room temperature ([DLA]$_0$/[I]$_0$=18). Conversion of DLA was about 95%. Acetic anhydride (57 mg, 0.56 mmol)

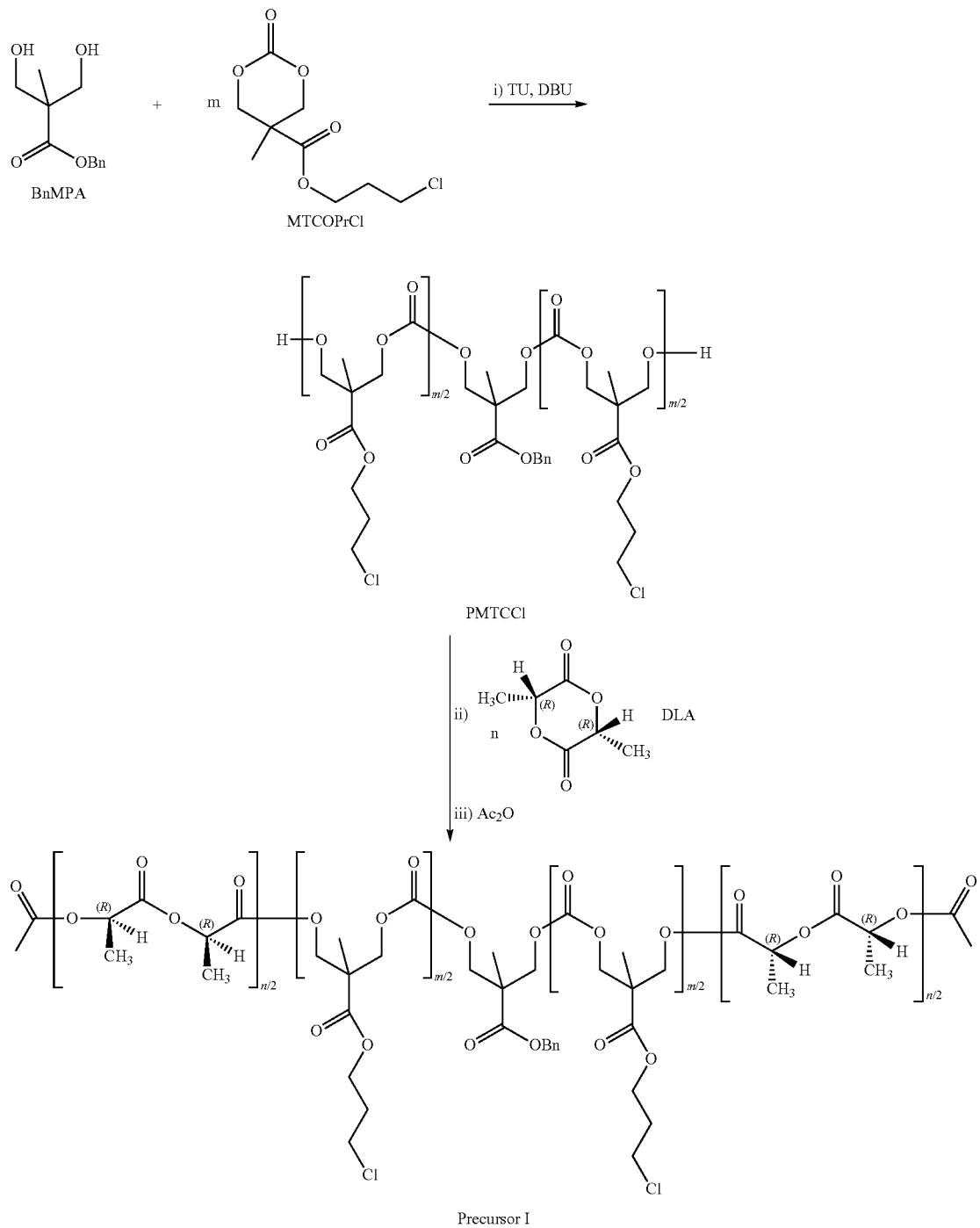

was added to the reaction mixture, and stirring was continued 96 hours, thereby forming an acetyl endcapped precursor triblock copolymer, Precursor I. The endcapped block copolymer was precipitated in cold methanol, centrifuged, and dried in vacuum. Yield of Precursor I: 497 mg (77%), GPC (THF): Mn 12700 g/mol, PDI 1.15, $^1$H NMR (400 MHz, CDCl$_3$): delta 7.39-7.28 (m, ArH$_{initiator}$), 5.23-5.05 (m, PhCH$_{2\ initiator}$, CH$_{PDLA}$), 4.40-4.17 (m, CH$_2$OCOO$_{MTCOPrCl}$, OCH$_{2\ PCCP}$), 3.65-3.53 (m, CH$_2$Cl$_{MTCOPrCl}$), 2.17-2.03 (m, CH$_{2\ MTCOPrCl}$, OCH$_{3\ end\ group}$), 1.64-1.46 (m, CH$_{3\ PDLA}$) 1.31-1.19 (m, CH$_{3\ MTCOPrCl}$).

Example 18

Precursor Triblock Copolymer II (Precursor II)

This polymer was prepared by the procedure of Example 17 (Precursor I), using L-lactide (LLA) at the second polymerization. Yield: 543 mg (83%), GPC (THF): Mn 11900 g/mol, PDI 1.15.

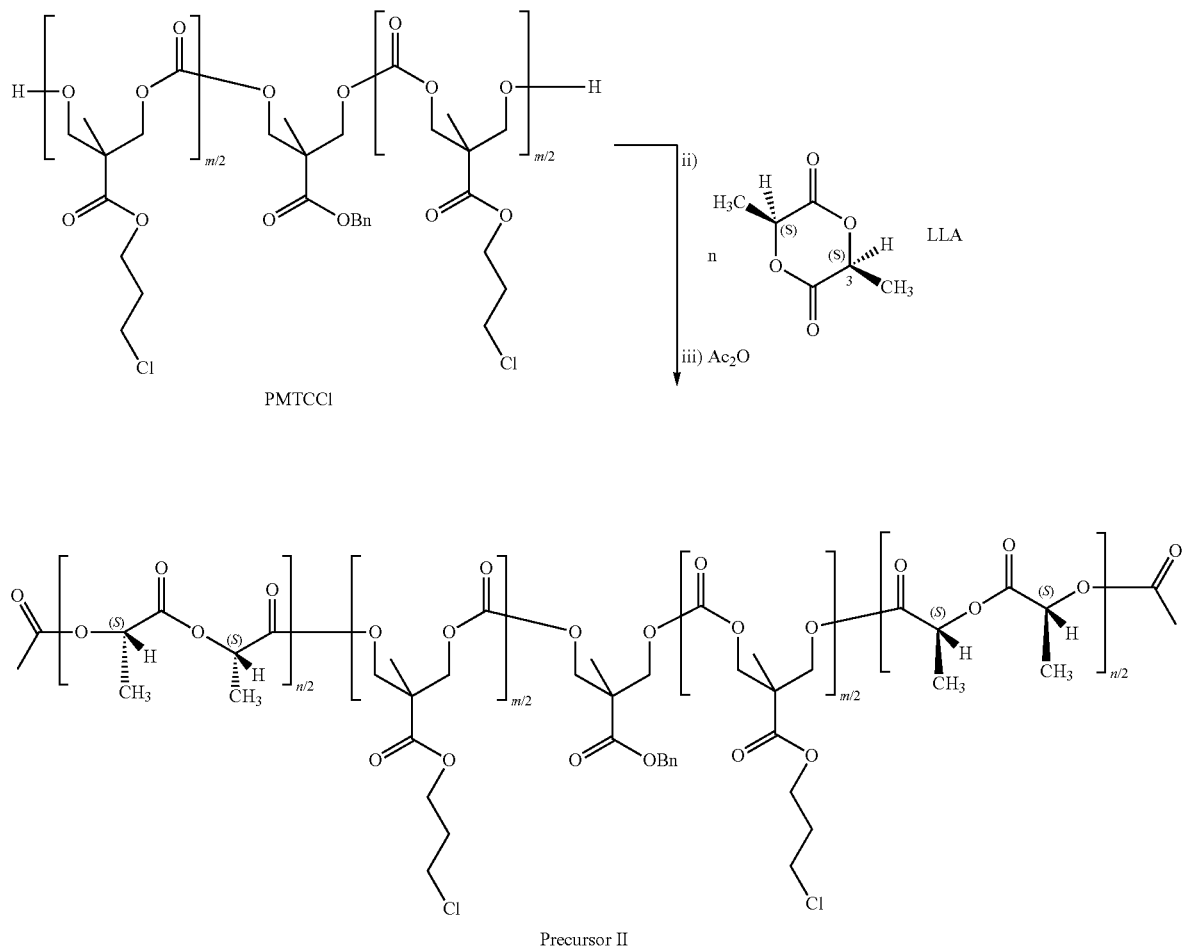

Precursor II

Example 19

Precursor Triblock Copolymer III (Precursor III)

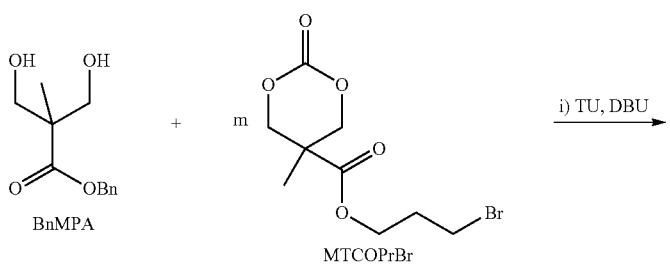

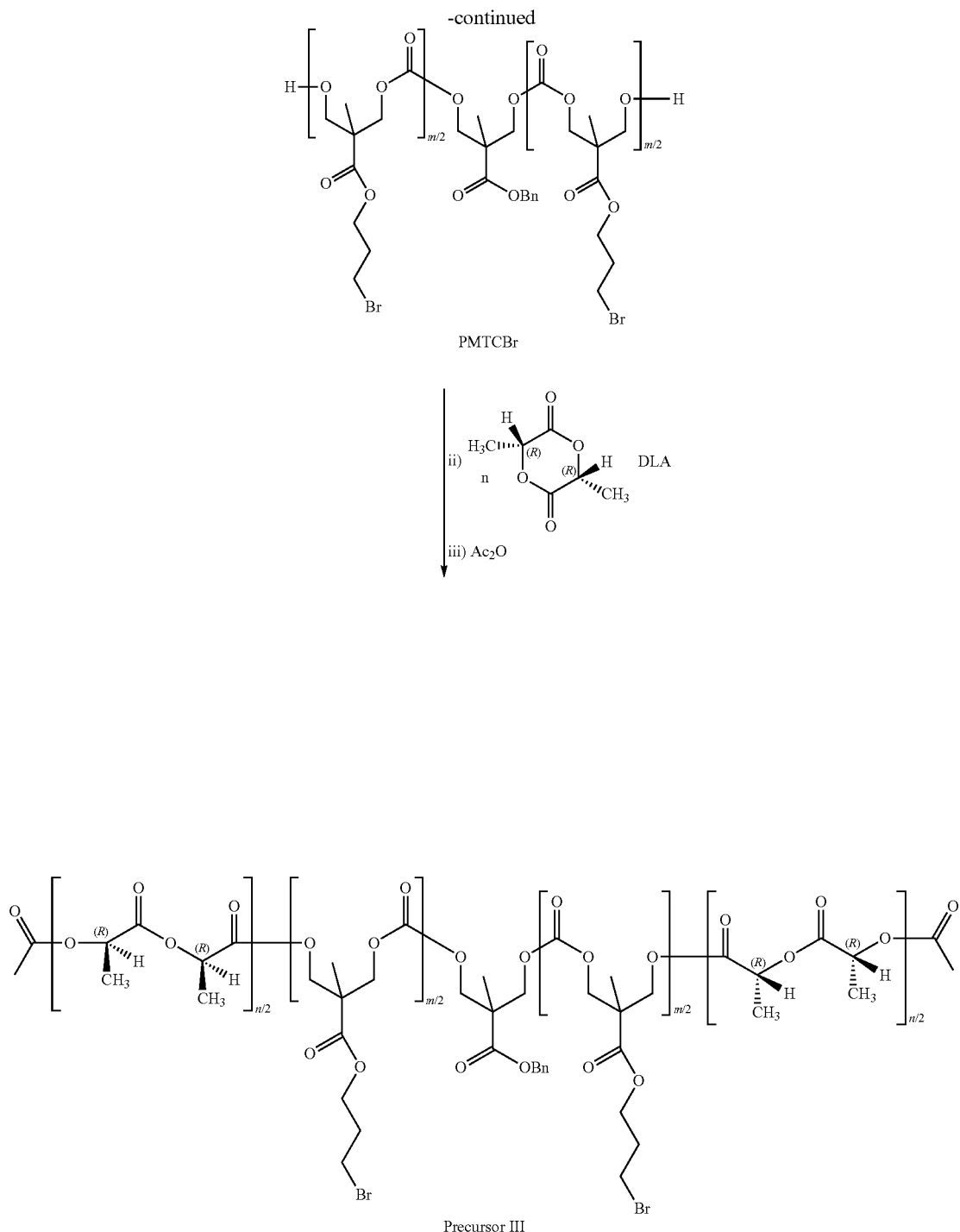

MTCOPrBr (325 mg, 1.15 mmol), BnMPA (14.5 mg, 0.065 mmol), and TU (11.9 mg, 0.032 mmol) were dissolved in methylene chloride (1.6 mL), and this solution was transferred to a vial containing DBU (5.1 mg, 0.033 mmol) to start polymerization at room temperature ([MTCOPrBr]$_0$/[I]$_0$=18). After 3 hours (conversion of MTCOPrBr was about 92%), the solution was transferred to a vial containing D-lactide (DLA) (146 mg, 1.01 mmol) to start the second polymerization. The reaction was stirred for 3 hours at room temperature ([DLA]$_0$/[I]$_0$=16). Conversion of DLA was about 97%. Acetic anhydride (54 mg, 0.53 mmol) was added to the reaction mixture and stirring was continued 72 hours. The product was precipitated in cold methanol after additional 72 hours stirring. The precipitate was centrifuged and dried in vacuum. Yield: 307 mg (63%), GPC (THF): Mn 4400 g/mol, PDI 1.08, $^1$H NMR (400 MHz, CDCl$_3$): delta 7.40-7.28 (m, Ar H$_{initiator}$), 5.26-5.04 (m, PhCH$_{2\ initiator}$, CH$_{PLA}$), 4.41-4.16 (m, CH$_2$OCOO$_{MTCOPrBr}$, OCH$_{2\ MTCOPrBr}$), 3.53-3.37 (m, CH$_2$Br$_{MTCOPrBr}$), 2.25-2.14 (m, CH$_{2\ PCBP}$), 2.13 (s, OCH$_{3\ end\ group}$), 1.64-1.46 (m, CH$_{3\ PLA}$), 1.33-1.19 (m, CH$_{3\ MTCOPrBr}$).

Example 20

Precursor Triblock Copolymer IV (Precursor IV)

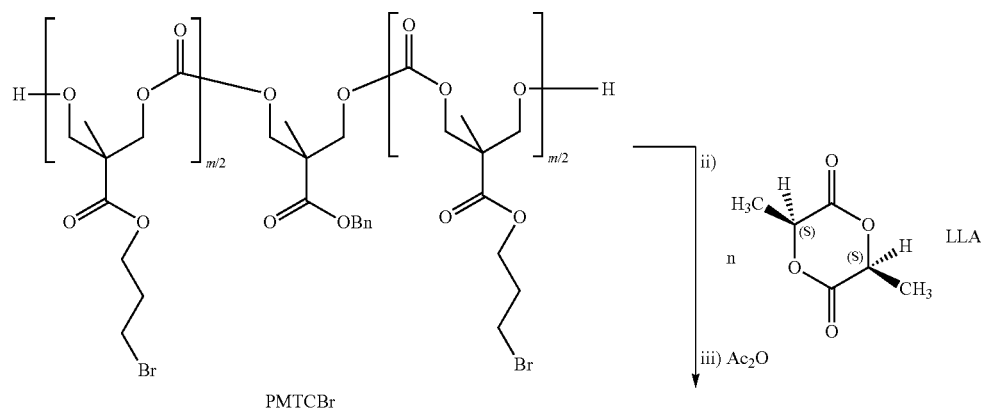

PMTCBr

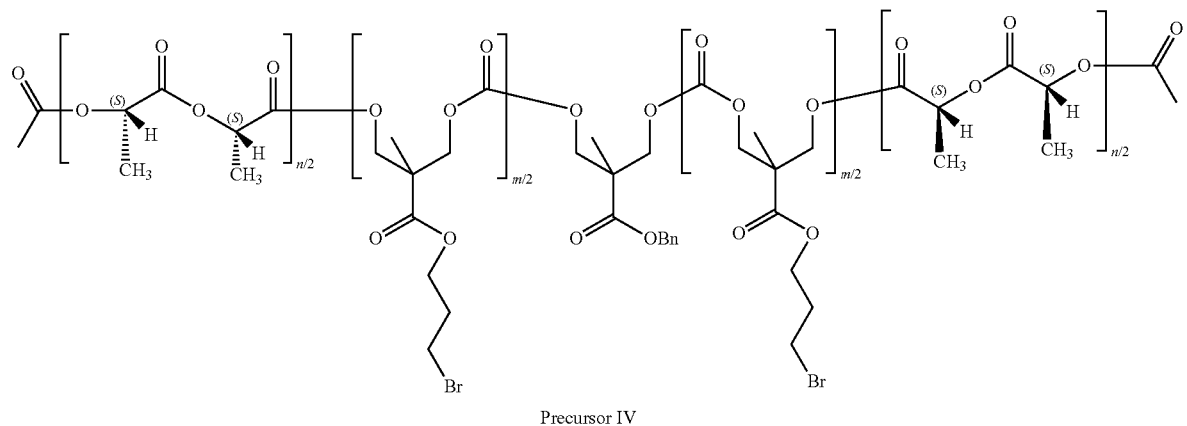

Precursor IV

Precursor IV was prepared by the procedure of Example 17 (Precursor III), using L-lactide (LLA) at the second polymerization instead of D-lactide. Yield: 314 mg (65%), GPC (THF): Mn 4900 g/mol, PDI 1.09.

Quaternization of Precursor Triblock Copolymers I to IV (Examples 17 to 20).

Quaternization of the core polycarbonate block (block B) with trimethylamine produced cationic triblock copolymers. The polymer backbone is biodegradable. In the four cationic triblock copolymer structures below, Block A is shown as not including the endcap group, as these can differ in each Block A. Block B includes the initiator fragment derived from the diol initiator BnMPA.

Example 21

Quaternization of Example 11 (Precursor I) to Form PCC1

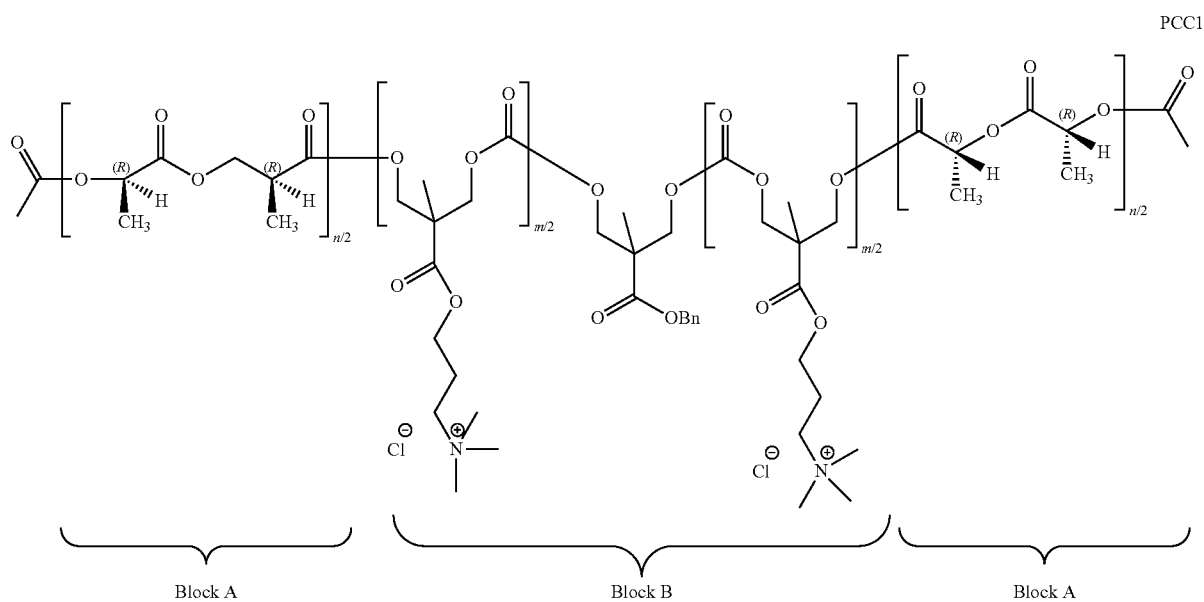

PCC1

Trimethylamine gas (782 mg, 13.2 mmol) was charged to an acetonitrile solution (4 mL) of Precursor I of Example 11 (466 mg, [Cl]=0.98 mmol) immersed in a dry-ice/acetone bath. The solution was then allowed to warm up to 50° C. and kept stirring for 14 hours before acetonitrile and excess gasses were removed under vacuum. The concentrated residue was dried in vacuum (~88% quaternized). Yield of PCC1: 461 mg (88%), GPC (DMF): Mn 8900 g/mol, PDI 1.17, $^1$H NMR (400 MHz, MeOH-$d_4$): delta 7.44-7.31 (m, ArH$_{initiator}$), 5.27-5.03 (m, PhCH$_2$ $_{initiator}$, CH$_{P(DLA)}$), 4.48-4.18 (m, CH$_2$OCOO$_{P(MTCOPr+NMe3\ Cl-)}$, CH$_2$O$_{P(MTCOPr+NMe3\ Cl-)}$), 3.59-3.41 (br, N$^+$CH$_2$ $_{P(MTCOPr+NMe3\ Cl-)}$), 3.25-3.13 (br, N$^+$CH$_3$ $_{P(MTCOPr+NMe3\ Cl-)}$), 2.29-2.16 (br, CH$_2$ $_{P(MTCOPr+NMe3\ Cl-)}$), 2.09 (s, OCH$_3$ $_{end\ group}$), 1.60-1.40 (m, CH$_3$ $_{P(DLA)}$), 1.35-1.24 (m, CH$_3$ $_{P(MTCOPr+NMe3\ Cl-)}$).

Example 22
Quaternization of Example 18 (Precursor II) to Form PCC2
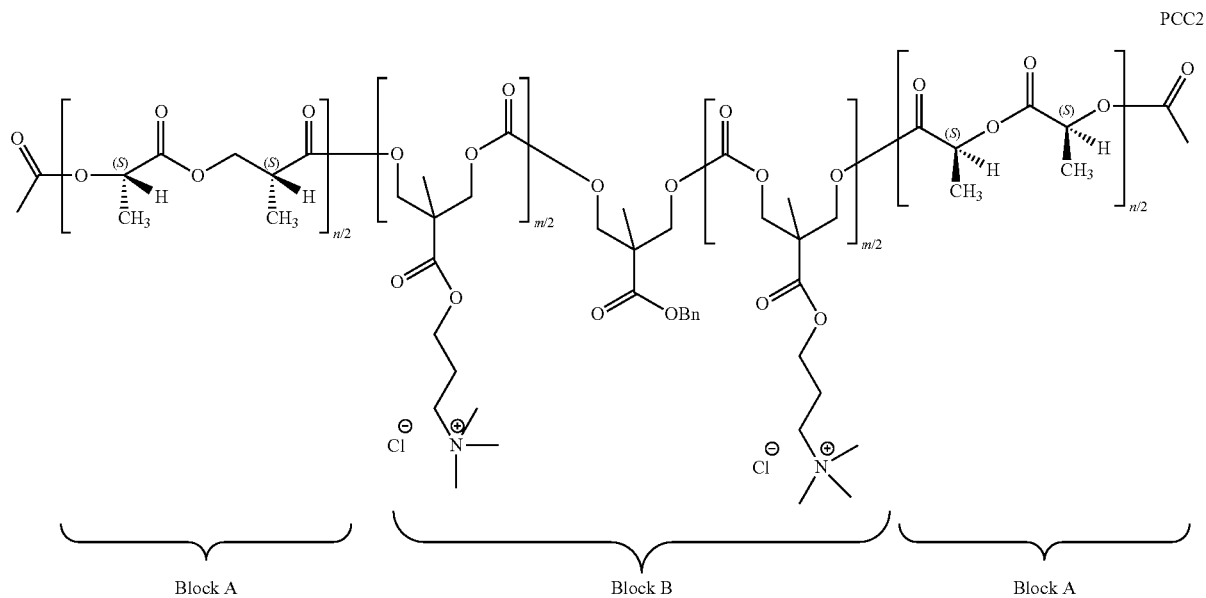
PCC2 (~89% quaternized) was prepared by the procedure of Example 21 using Precursor II. Yield of PCC2: 471 mg (81%), GPC (DMF): Mn 9400 g/mol, PDI 1.15.
Example 23
Quaternization of Example 19 (Precursor III) to Form PCC3
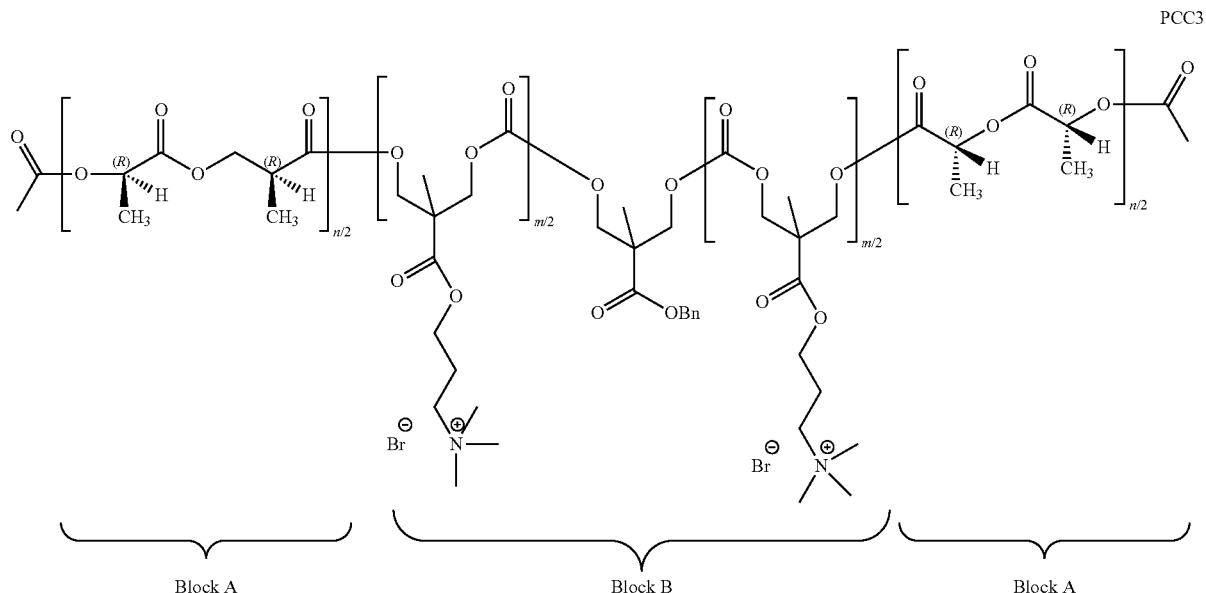

Trimethylamine gas (844 mg, 14.3 mmol) was charged to a mixed solution of acetonitrile (4 mL) and DMF (2 mL) dissolving Precursor III (Example 19) (250 mg, [Br]=0.56 mmol) immersed in a dry-ice/acetone bath. The solution was then allowed to warm to room temperature and kept stirring for 18 hours before acetonitrile and excess gasses were removed under vacuum (~92% quaternized). The concentrated residue was then precipitated in diethylether and the precipitates were collected by centrifugation and dried in vacuum. Yield of PCC3: 221 mg (78%), $^1$H NMR (400 MHz, MeOH-$d_4$): delta 7.42-7.34 (m, ArH$_{initiator}$), 5.26-5.04 (m, PhCH$_2$ $_{initiator}$, CH$_{P(DLA)}$), 4.45-4.20 (m, CH$_2$ OCOO$_{P(MTCOPr+NMe3\ Br—)}$, CH$_2$O$_{P(MTCOPr+NMe3\ Br—)}$), 3.63-3.43 (br, N$^+$CH$_2$ $_{P(MTCOPr+NMe3\ Br—)}$) 3.28-3.13 (br, N$^+$CH$_3$ $_{P(MTCOPr+NMe3\ Br—)}$), 2.31-2.15 (br, CH$_2$ $_{P(MTCOPr+NMe3\ Br—)}$), 2.09 (s, OCH$_3$ $_{end\ group}$), 1.62-1.40 (m, CH$_3$ $_{P(DLA)}$), 1.36-1.24 (m, CH$_3$ $_{P(MTCOPr+NMe3\ Br—)}$).

Example 24

Quaternization of Example 20 (Precursor IV) to Form PCC4

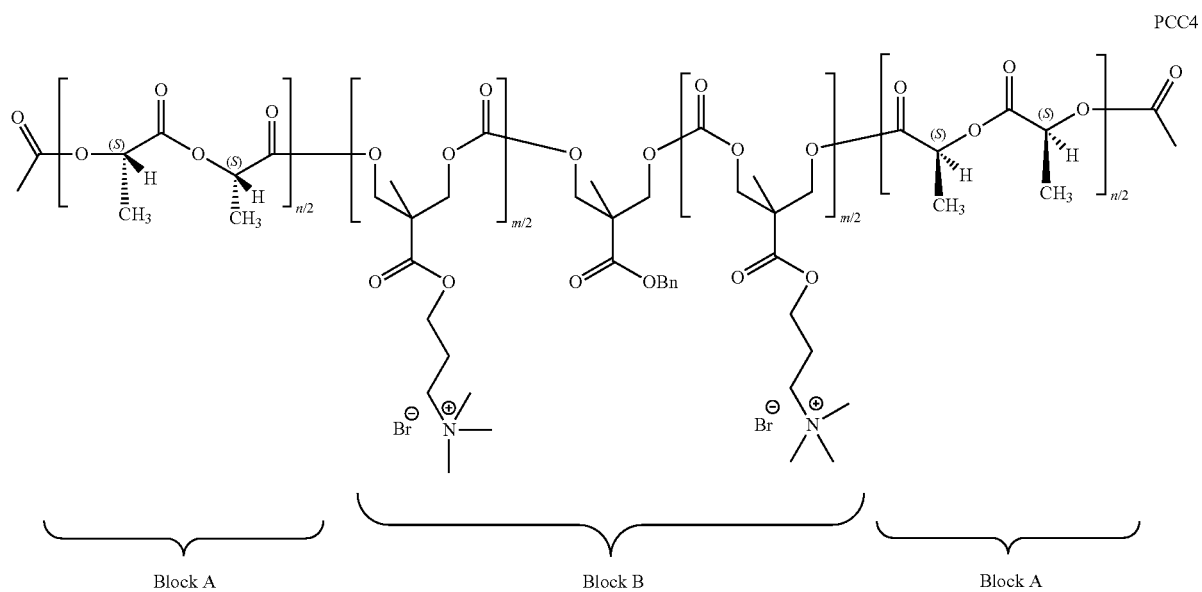

PCC4

PCC4 (~92% quaternized) was prepared by the procedure used in Example 23 using Precursor IV (Example 20). Yield: 243 mg (83%).

The characteristics of the cationic triblock copolymers formed in Examples 15 to 18 are shown in Table 11.

TABLE 11

| Example | Cationic Triblock Copolymer | Lactide isomer | X[1] | Block B Kdalton/mol (polycarbonate) | Each Block A Kdalton/mol (polylactide) | Mn g/mol (NMR) | PDI[2] | N$^+$ %[3] |
|---|---|---|---|---|---|---|---|---|
| 21 | PCC1 | D | Cl | 4.3 | 1.3 | 6800 | 1.15 | 88 |
| 22 | PCC2 | L | Cl | 4.4 | 1.2 | 6900 | 1.15 | 89 |
| 23 | PCC3 | D | Br | 5.6 | 1.1 | 7800 | 1.08 | 92 |
| 24 | PCC4 | L | Br | 5.8 | 1.1 | 8000 | 1.09 | 92 |

[1]Counter ion.
[2]The values of precursor triblock copolymers.
[3]percentage of quaternization in the polycarbonate blocks.

Examples 25 to 27

Repeats of Example 23 using different molecular weights of block A and block B. Example 23 was repeated to form cationic triblock copolymers having different polycarbonate (block B) and poly(D-lactide) (block A) molecular weights. The results are summarized in Table 12.

TABLE 12

| Example | Cationic Triblock Copolymer | Lactide Isomer | $X^1$ | Block B Kdalton/ mol (polycarbonate) | Each Block A Kdalton/ mol (polylactide) | Mn g/mol (GPC) | PDI |
|---|---|---|---|---|---|---|---|
| 25 | PCC5 | D | Br | 6 | 1 | 6200 | 1.29 |
| 26 | PCC6 | D | Br | 12 | 2 | 8700 | 1.28 |
| 27 | PCC7 | D | Br | 8 | 1.5 | 6700 | 1.21 |

Preparation of Hydrogels

Example 28C (Comparison)

A 10 wt. % aqueous solution of the cationic triblock copolymer PCC3 (Example 23) and a 10 wt. % aqueous solution of the cationic triblock copolymer PCC4 (Example 24) were prepared by dissolving the respective polymers directly in DI water. The polymer solutions were then combined. The concentration of the combined polymers was 100 mg/ml, or 10% w/v (5% w/v for each polymer). Interestingly, upon mixing, the solutions remain clear and formed micelles. The combined solution was heated at 40° C. for 1 hour.

Example 29

Non-charged triblock copolymer PEG1D20 (Example 7) (50 mg) was dissolved in tetrahydrofuran (THF) (0.25 mL) and the solution was added dropwise into deionized (DI) water (0.5 mL) to form a suspension. The THF was removed under vacuum to formulate a 10% (w/v) aqueous mixture. This was combined with a 10% w/v aqueous solution of PCC4 (50 mg/0.5 ml) in water. The concentration of the mixed complex was 100 mg/ml, or 10% w/v (5% w/v for each polymer). The weight ratio of the cationic polymer to the non-charged polymer was 1:1 w/w in the hydrogel. The combined solution was heated at 40° C. for 1 hour to form a hydrogel.

The results for Examples 28C and 29 are summarized in Table 13.

TABLE 13

| Example | Solution 1 (10% w/v) | Solution 2 (10% w/v) | Hydrogel at 40° C.? (Yes/No) |
|---|---|---|---|
| 28C | PCC3 (Example 23) | PCC4 (Example 24) | No |
| 29 | PEG1D20 (Example 7) | PCC4 (Example 24) | Yes |

Figure 1B:
FIG. 1B is a photograph of the solution of Example 28C (FIG. 1A) after heating the solution for 1 hour at 40° C. The combination of the two cationic triblock copolymers, PCC3 and PCC4, did not form a hydrogel.
Figure 1C:
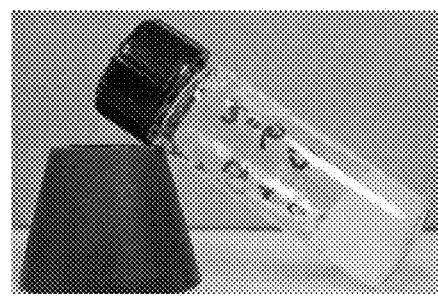
FIG. 1C is a photograph of a hydrogel formed in Example 29 after heating the aqueous mixture 1 hour at 40° C. The aqueous mixture contained equal amounts of the non-charged triblock copolymer of PEG1D20 (Example 7) and the cationic triblock copolymer PCC4 (Example 24).

Example 28C, which contained a mixture of two cationic triblock copolymers, PCC3 and PCC4, did not form a hydrogel. FIG. 1A is a photograph of the resulting solution of Example 28C before heating. FIG. 1B is a photograph of Example 28C after heating the combined solutions for 1 hour at 40° C. Example 29, which contained a mixed complex of non-charged triblock copolymer PEG1D20 and cationic triblock copolymer PCC4, formed a hydrogel. FIG. 1C is a photograph of the hydrogel formed in Example 29 after heating the aqueous mixture 1 hour at 40° C.

Micelle Characterization

Examples 30C, 31C, 32C, 33C, 34C, and 35 to 40

Examples 30C, 31C, and 32C are comparison examples containing only a cationic triblock copolymer in water. Examples 33C and 34C are comparison examples containing only a non-charged triblock copolymer in water. Examples 35 to 40 are inventive examples containing a mixed complex of a non-charged triblock copolymer and a cationic triblock copolymer in water. The following procedure was used to form polymer solutions for particle size and zeta potential analyses (Table 14 below). Aqueous solutions of cationic triblock copolymer and non-charged triblock copolymer were formed by wetting the triblock copolymer with tetrahydrofuran (THF) (1 mg/microliter), and then adding DI water to make a 0.1% w/v (1 mg/mL) solution of the triblock copolymer. For Examples 35 to 40, the aqueous solutions were then combined to form a mixed complex. Each sample contained 1 microliter THF per milliliter of aqueous solution. The THF was removed by vacuum drying for 10 minutes. The final aqueous solutions contained a total polymer concentration of 1 mg/mL (0.1% w/v). At this total polymer concentration, a hydrogel was not formed. Examples 35 to 40 contained a 1:1 w/w mixture of the non-charged triblock copolymer and charged triblock copolymer, respectively. The samples were equilibrated for 1 hour. Hydrodynamic particle size of the samples was measured using a Zetasizer (3000 HAS, Malvern Instrument, U.K.) at room temperature (about 25° C.). Each measurement was repeated five times. An average value was obtained from the five measurements. Table 14 lists the general characteristics of the samples after removing the organic solvent, where S.D. is the standard deviation of the measurement in the adjacent column to the left. The formation of particles with sizes ranging from about 40 nm to about 181 nm confirm the formation of micelles and the charge on the micelles is in an appropriate range to serve as a good antimicrobial agent. PDI in Table 14 is a polydispersity index of the micelles. A lower value indicates a more narrowly dispersed system.

TABLE 14

| Example | Cationic triblock Copolymer | Non-Charged Triblock Copolymer | Particle Size (nm) | S.D. | PDI | Zeta Potential (mV) | S.D. |
|---|---|---|---|---|---|---|---|
| 30C | PCC5 (Example 25) | | 133.7 | 6.0 | 0.53 | 58.2 | 1.25 |
| 31C | PCC6 (Example 26) | | 181.1 | 36.9 | 0.34 | 69.2 | 0.56 |
| 32C | PCC7 (Example 27) | | 147.6 | 2.0 | 0.21 | 25.3 | 2.6 |
| 33C | | PEG1L10 (Example 12) | 54.6 | 17.2 | 0.36 | −5.9 | 1.9 |
| 34C | | PEG1L20 (Example 8) | 132.7 | 7.9 | 0.52 | −4.8 | 0.58 |
| 35 | PCC5 (Example 25) | PEG1L10 (Example 12) | 41.3 | 1.8 | 0.43 | 21.3 | 2.1 |
| 36 | PCC6 (Example 26) | PEG1L10 (Example 12) | 37.4 | 0.22 | 0.37 | 24.1 | 2.7 |
| 37 | PCC7 (Example 27) | PEG1L10 (Example 12) | 46.0 | 1.1 | 0.43 | 27.2 | 1.9 |
| 38 | PCC5 (Example 25) | PEG1L20 (Example 8) | 136.7 | 19.1 | 0.40 | 20.4 | 0.47 |
| 39 | PCC6 (Example 26) | PEG1L20 (Example 8) | 99.6 | 13.4 | 0.59 | 26.8 | 0.46 |
| 40 | PCC7 (Example 27) | PEG1L20 (Example 8) | 101.8 | 8.7 | 0.56 | 20.0 | 0.12 |

Hydrogel Formation.

Examples 41C, 42C, 43C, 44C, 45C, and 46 to 51 demonstrate hydrogel formation, or lack thereof, of the single polymers and mixed polymer examples of Table 14, respectively. Examples 41C to 45C are comparison examples containing single triblock copolymer in water. Examples 46 to 51 are inventive examples containing a mixed complex of a non-charged triblock copolymer and a cationic triblock copolymer in water. In each example, the total polymer concentration was 10% w/v (100 mg/ml), and in Examples 46 to 51, the non-charged:charged polymer ratio was 1:1 w/w.

The aqueous solutions were prepared as follows. The individual polymers were wetted with tetrahydrofuran (THF) (1 mg/microliter) individually, and DI water was then added to make a polymer concentration of 10% w/v (100 mg/mL). For the mixed complexes (Examples 46 to 51), the polymer solutions were then combined, followed by vacuum drying for 10 min to remove THF. Table 15 summarizes the results. Examples 41C to 43C (cationic triblock copolymer alone) did not form a hydrogel at ambient temperature or when heated to 40° C. Examples 44C and 45C (non-charged triblock alone), and Examples 46 to 51 (combination of cationic triblock copolymer and non-charged triblock copolymer) formed a hydrogel at ambient temperature. The resultant hydrogel was equilibrated at 37° C. for 1 hour. Upon gel formation, the solutions became cloudy, typical of a higher ordered or larger structure. The formation of a hydrogel by Examples 44C and 45C (non-charged triblock copolymers alone) demonstrates that opposite stereochemistry of the hydrophobic chains in a mixed complex is not necessary for the formation of a hydrogel.

TABLE 15

| Example | Solution 1, Cationic Polymer (10% w/v) | Solution 2, Non-Charged Polymer (10% w/v) | Hydrogel at ambient temperature or 40° C.? (Yes/No) |
|---|---|---|---|
| 41C | PCC5 (Example 25) | | No |
| 42C | PCC6 (Example 26) | | No |
| 43C | PCC7 (Example 27) | | No |
| 44C | | PEG1L10 (Example 12) | Yes |
| 45C | | PEG1L20 (Example 8) | Yes |
| 46 | PCC5 (Example 25) | PEG1L10 (Example 12) | Yes |
| 47 | PCC6 (Example 26) | PEG1L10 (Example 12) | Yes |
| 48 | PCC7 (Example 27) | PEG1L10 (Example 12) | Yes |
| 49 | PCC5 (Example 25) | PEG1L20 (Example 8) | Yes |
| 50 | PCC6 (Example 26) | PEG1L20 (Example 8) | Yes |
| 51 | PCC7 (Example 27) | PEG1L20 (Example 8) | Yes |

Table 16 summarizes the weight percents of D-lactide and L-lactide contributed by each triblock copolymer in the mixed complexes of Example 29, and Examples 46 to 51.

TABLE 16

| Example | Cationic triblock Copolymer | Non-Charged Triblock Copolymer | Cationic Triblock Copolymer (Wt. % Lactide in Mixed Complex) | | Non-Charged Triblock Copolymer (Wt. % Lactide in Mixed Complex) | | Lactide Weight Ratio in Mixed Complex Cationic Triblock:Non-Charged Triblock w/w |
|---|---|---|---|---|---|---|---|
| | | | L-Lactide (wt. %) | D-Lactide (wt. %) | L-Lactide (wt. %) | D-Lactide (wt. %) | |
| 29 | PCC4 (Example 24) | PEG1D20 (Example 7) | 11.1 | | | 22.2 | 1.0:2.0 |
| 46 | PCC5 (Example 25) | PEG1L10 (Example 12) | | 12.5 | 12.5 | | 1.0:1.0 |
| 47 | PCC6 (Example 26) | PEG1L10 (Example 12) | | 18.2 | 9.1 | | 1.0:0.5 |
| 48 | PCC7 (Example 27) | PEG1L10 (Example 12) | | 15.8 | 10.5 | | 1.0:0.66 |
| 49 | PCC5 (Example 25) | PEG1L20 (Example 8) | | 11.1 | 22.2 | | 1.0:2.0 |
| 50 | PCC6 (Example 26) | PEG1L20 (Example 8) | | 16.7 | 16.7 | | 1.0:1.0 |
| 51 | PCC7 (Example 27) | PEG1L20 (Example 8) | | 14.3 | 19.0 | | 1.0:1.33 |

As stated above, removing the organic solvent from the aqueous mixtures of Examples 44C and 45C (non-charged triblock alone), and Examples 46 to 51 (combination of cationic triblock copolymer and non-charged triblock copolymer) resulted in formation of a hydrogel at ambient temperature. Example 29 did not form a hydrogel until heated to 40° C. Examples 29 and 49 have opposite stereochemistry but otherwise the same composition and molecular weight, yet show different gel forming behavior.

Figure 2A:
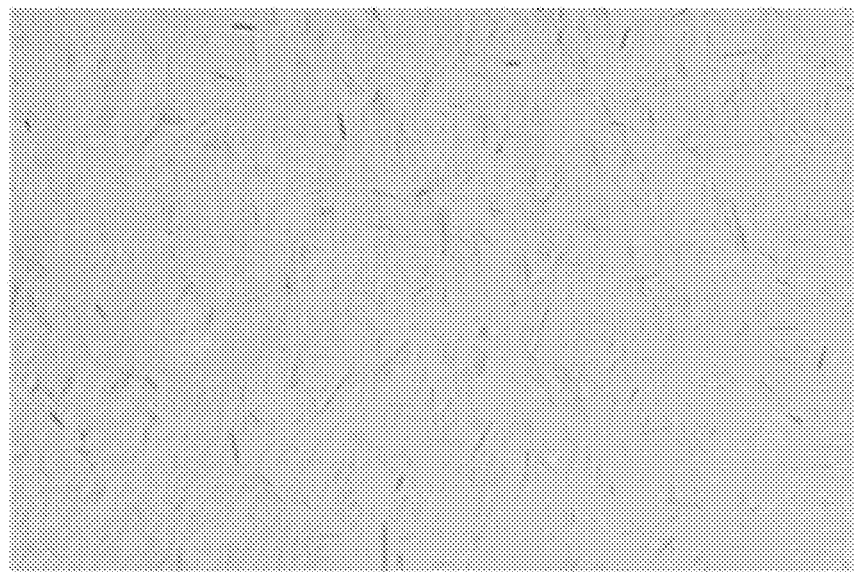
FIGS. 2A to 2C are optical micrographs of hydrogels formed in Examples 49 to 51, respectively, which contain a mixed complex of a cationic triblock copolymer and a non-charged triblock copolymer. The optical micrographs show a rod-like structure suspended in the watery hydrogel.
Figure 2B:
Figure 2C:
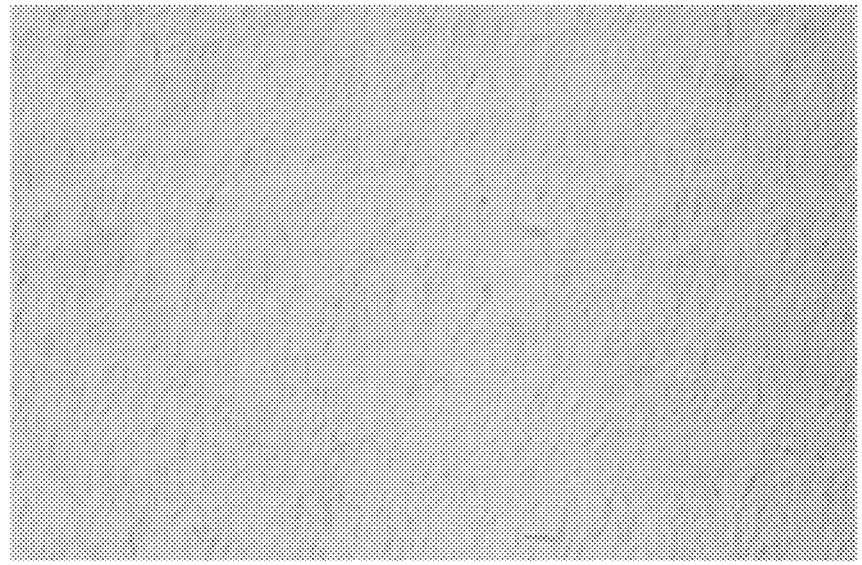
Figure 2D:
FIG. 2D is an optical micrograph of the hydrogel formed by Comparative Example 45C, which contains only a non-charged triblock copolymer, PEG1L20. The rod-like structure is observed.

A closer look at the hydrogels clearly reveals the formation of a supramolecular structure, as seen in the optical micrographs of FIG. 2A (Example 49), FIG. 2B (Example 50), FIG. 2C (Example 51) and FIG. 2D (Example 45C). The hydrogels were opaque. The optical micrographs show a rod-like structure suspended in the watery hydrogel. Surprisingly, the rod-like structures are of uniform width (100 nm to 500 nm) and have high aspect ratios, varying in length from about 0.5 micrometer to about 50 micrometers. The generation of this rod-like structure also likely gives rise to the gel and controls the mechanical properties. FIGS. 2A to 2D show that the rod-like structures were formed by the non-charged triblock copolymer alone in water (Example 45C), and by the mixture of the cationic and non-charged triblock copolymers (Examples 49 to 51). The cationic triblock copolymers alone (Examples 41C to 43C) did not form rod-like structures in water.

TEM Observation of Hydrogel.

Figure 3A:
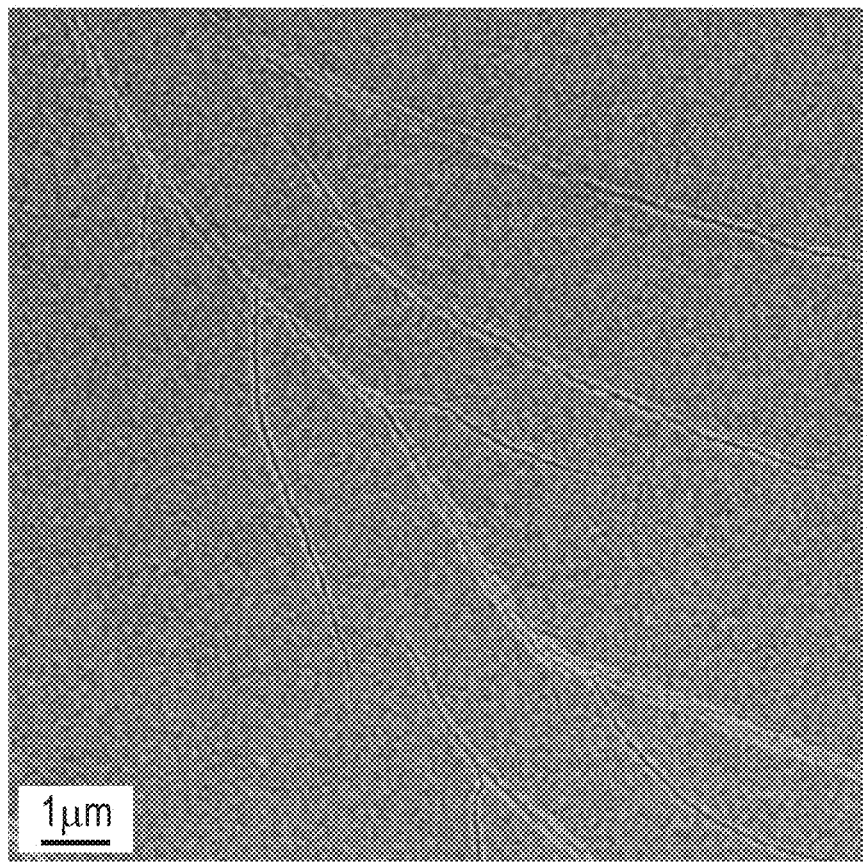
FIGS. 3A to 3C are higher resolution TEM images of the rod-like structure of the hydrogel formed by Example 45C (non-charged PEG1L20 alone).
Figure 3B:
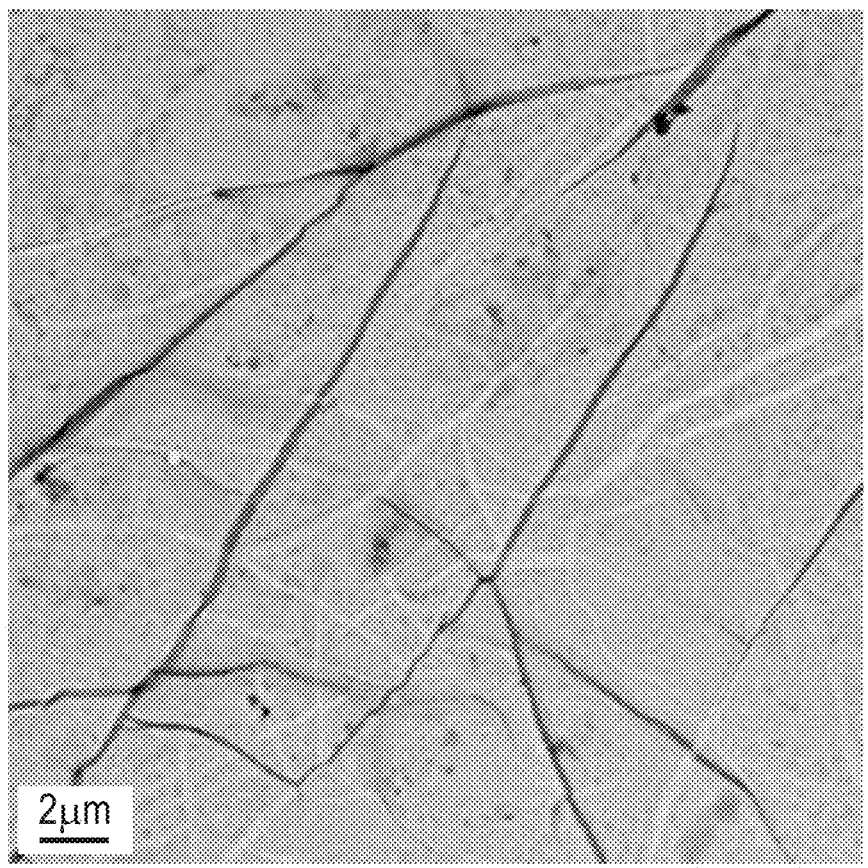
Figure 3C:
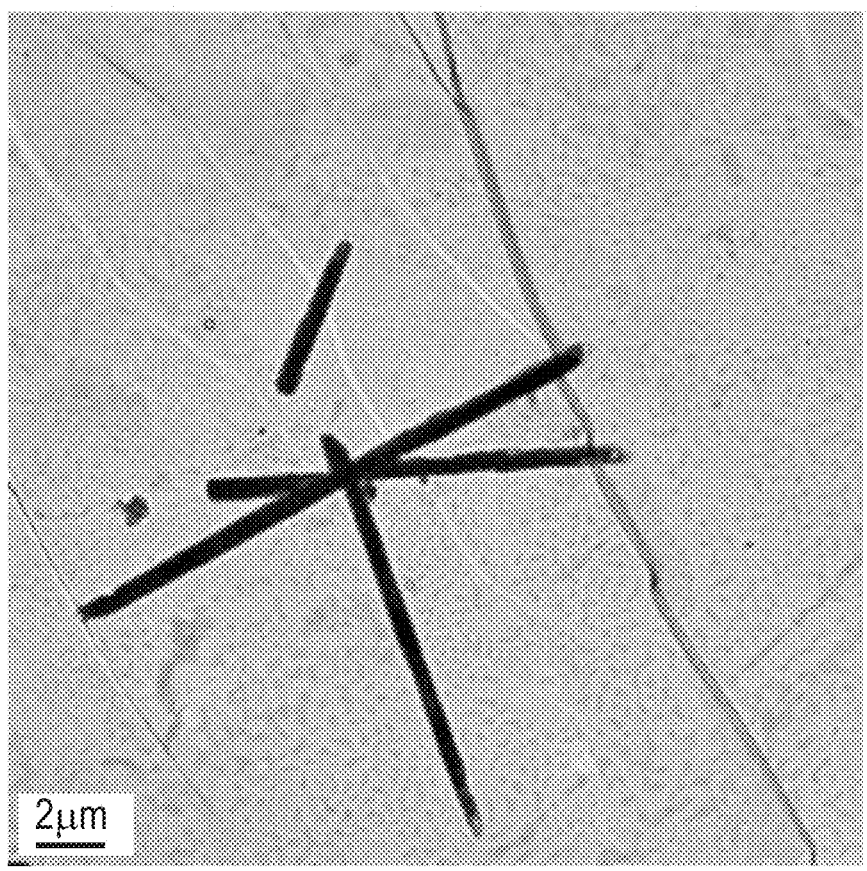

The rod-like structure was also observed under a FEI Tecnai G2 F20 transmission electron microscope (TEM) using an acceleration voltage of 200 KeV. To prepare the TEM sample, several drops of the aqueous polymer solution at a concentration of 1000 mg/L containing 0.2% (w/v) of phosphotungstic acid were placed on a formcar/carbon-coated 200 mesh copper grid and left to dry under room temperature prior to TEM observation. FIGS. 3A to 3C are TEM images of the hydrogel structure obtained with Example 45C (non-charged PEG1L20 alone) in this manner. The images clearly show the rod-like structures in the hydrogel.

Antimicrobial Activity of Hydrogels.

The efficacy of the aqueous mixtures as antimicrobial agents was investigated against Gram-negative bacteria and against Gram-positive bacteria and fungi. Generally, Gram-positive bacteria and fungi are easier to kill owing to their single highly charged membrane. Gram-negative bacteria are more difficult to destroy as they have a dual membrane and their charge is significantly less making electrostatics as a means to lyse the membrane less likely.

Examples 52C, 53C, and 54 to 59

The following general procedure was used to prepare hydrogels for antimicrobial testing (see also Table 17 below). The cationic and non-charged triblock copolymers were individually wetted with tetrahydrofuran (THF) (1 mg/microliter), and DI water was then added to make a total polymer concentration of 10% w/v (100 mg/mL). Hydrogel was then formed by combining the two polymer solutions, and vacuum drying for 10 min to remove THF. The hydrogel was equilibrated at 37° C. for 1 hour. The concentration of the mixed complex (cationic polymer plus non-charged polymer) in the hydrogel was 100 mg/mL, or 10% w/v (5% w/v for each polymer). The weight ratio of cationic triblock copolymer to non-charged triblock copolymer in the mixed complex was 1:1 w/w. Examples 52C and 53C are hydrogels formed from non-charged triblock copolymer alone at a concentration of 10% w/v.

30 microliters of microorganism solution at a concentration that gave an optical density reading of approximately 0.1 to 0.2 at 600 nm was then added into each hydrogel. The non-charged triblock copolymer alone and phosphate buffer solution (PBS) (pH 7.4) containing cells were used as a negative control. The cell cultures were then incubated for 8 hours and the optical density was monitored at 2 hour intervals. After 8 hour incubation, 10 microliters of the microorganism with or without dilution using medium was taken out from the hydrogel and streaked on the agar plate. The agar plates were inverted and incubated in a 37° C. incubator for 24 hours and the colony forming units (CFUs) were counted.

Figure 4:
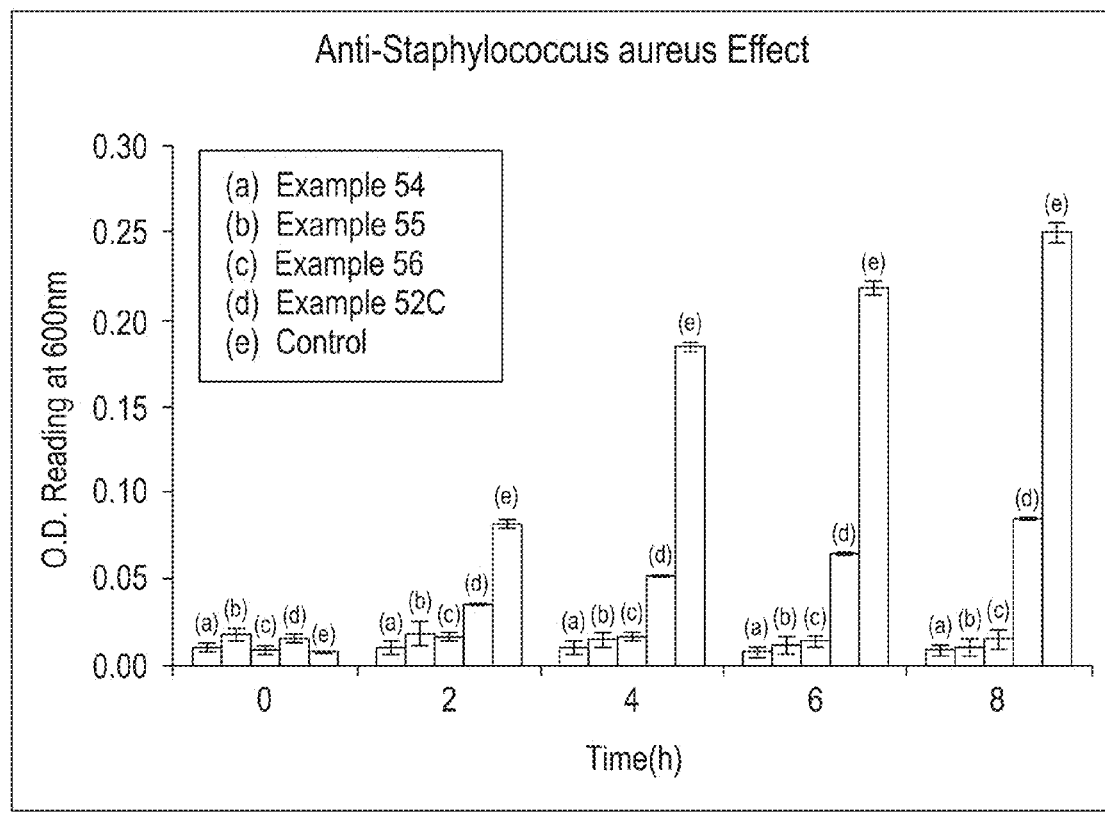
FIG. 4 is a bar graph comparing the antimicrobial activity of Example 52C (PEG1L10 alone) and Examples 54 to 56 (mixed complexes) against Gram-positive *Staphylococcus aureus*. A lower optical density indicates greater antimicrobial activity.
Figure 5:
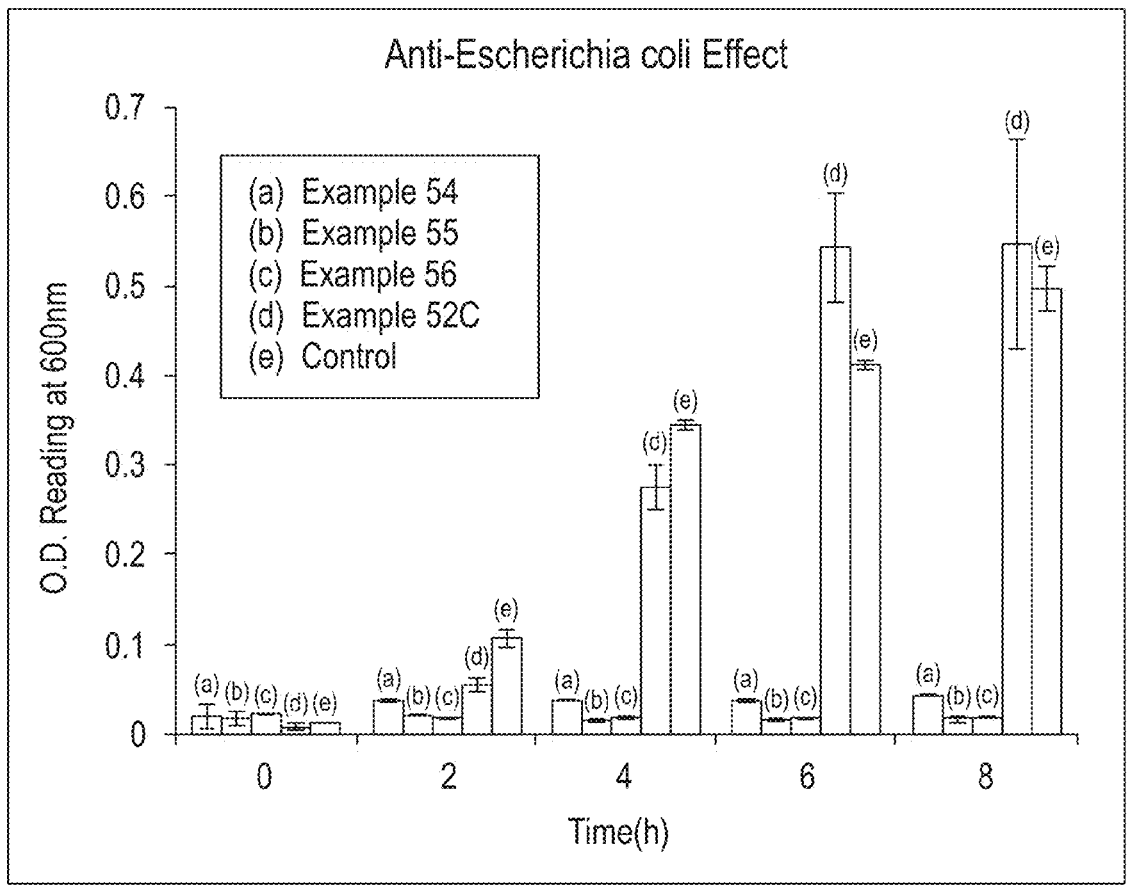
FIG. 5 is a bar graph comparing the antimicrobial activity of Example 52C (PEG1L10 alone), and Examples 54 to 56 (mixed complexes) against Gram-negative *Escherichia coli*.
Figure 6:
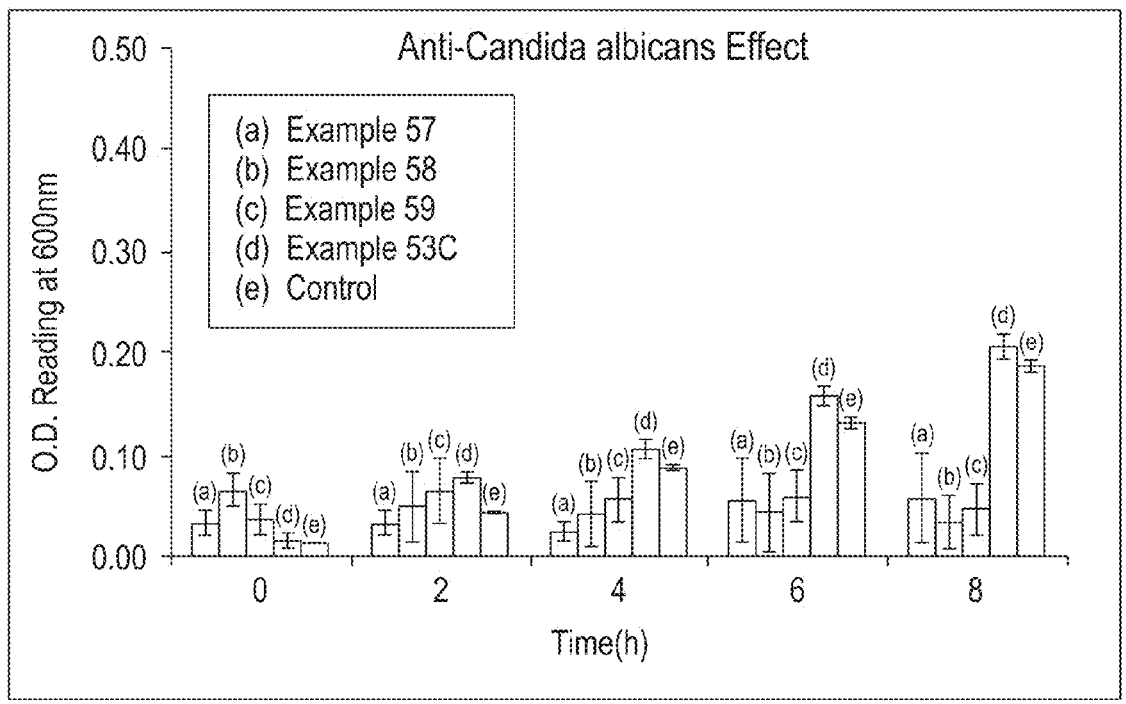
FIG. 6 is a bar graph comparing the antimicrobial activity of Example 53C (PEG1L20 alone), and Examples 57 to 59 (mixed complexes) against the fungus *Candida albicans* (a diploid fungus, a form of yeast).

FIGS. 4 to 6 below are bar graphs showing the antimicrobial activity of various hydrogel forming samples against Gram-positive and Gram-negative bacteria. The data in FIGS. 4 to 6 is also summarized below in Table 17 for the 8 hour incubation times. The control used in FIGS. 4 to 6 was 30 microliters of microbial solution plus 50 microliters of phosphate buffered saline (PBS) (pH 7.4), which was cultured in a 96-well plate. FIG. 4 compares the activity of the hydrogels formed with Example 52C (PEG1L10 alone), and Examples 54 to 56 (mixed complexes) against Gram-positive *Staphylococcus aureus* (*S. aureus*). FIG. 5 compares the activity of the hydrogels formed with Ex. 52C (PEG1L10 alone), and Examples 54 to 56 (mixed complexes) against Gram-negative *Escherichia coli* (*E. coli*). FIG. 6 compares the activity of the hydrogels formed with Examples 53C (PEG1L20 alone), and Examples 57 to 59 (mixed complexes) against the fungus *Candida albicans* (*C. albicans*). *C. albicans* is a diploid fungus, a form of yeast. A lower optical density at 600 nm indicates higher antimicrobial activity. Clearly, this data shows the hydrogels containing the mixed complexes (Examples 54 to 59) at a concentration of 100 mg/mL, or 10% w/v, are more toxic to Gram-negative and Gram-positive bacteria and fungus than either the Control (PBS solution) or a hydrogel formed by the non-charged polymer alone at the same concentration. The hydrogels formed by the non-charged triblock copolymers alone, Examples 52C and 53C, were not effective against *E. coli* and *C. albicans*, respectively, as evidenced by the O.D. at 600 nm at 8 hours being about the same as the Control PBS solution. Agar plating experiments also demonstrated that these stereocomplex hydrogels (Examples 54 to 59) are microbiocidal, as no CFU was observed.

Table 17 summarizes the antimicrobial activity observed in FIGS. 4 to 6 after 8 hours of incubation.

at the concentration at which no growth was observed. Broth containing cells alone was used as control.

Examples 60C to 63C are comparison examples in which the MIC was determined for individual cationic triblock copolymers (Examples 25 to 27) and non-charged triblock copolymer PEG1L10 (Example 12). A lower MIC count indicates greater microbiocidal activity. Table 18 lists the MIC data for Examples 60C to 63C.

TABLE 18

| | | MIC (mg/L) | |
| --- | --- | --- | --- |
| Example | Triblock Copolymer | Gram-positive *S. aureus* | Gram-negative *E. coli* |
| 60C | PCC5 (Example 25) | 10,000 | 10,000 |
| 61C | PCC6 (Example 26) | >25,000 | >25,000 |
| 62C | PCC7 (Example 27) | >25,000 | >25,000 |
| 63C | PEG1L10 (Example 12) | >25,000 | >25,000 |

TABLE 17

| Example | Polymer 1 Cationic (10% w/v) | Polymer 2 Non-Charged (10% w/v) | Polymer 1:Polymer 2 ratio (w/w) | *S. aureus*. (O.D$^a$ @ 8 h) | *E. coli* (O.D$^a$ @ 8 h) | *C. albicans* (O.D$^a$ @ 8 h) |
| --- | --- | --- | --- | --- | --- | --- |
| Control$^b$ | | | | ~0.25 | >0.45 | ~0.19 |
| 52C | | PEG1L10 (Example 12) | No Polymer 1 (10% w/v in Polymer 2) | ~0.08 | >0.50 | |
| 53C | | PEG1L20 (Example 8) | No Polymer 1 (10% w/v in Polymer 2) | | | ~0.20 |
| 54 | PCC5 (Example 25) | PEG1L10 (Example 12) | 1:1 | <0.03 | <0.05 | |
| 55 | PCC6 (Example 26) | PEG1L10 (Example 12) | 1:1 | <0.03 | <0.05 | |
| 56 | PCC7 (Example 27) | PEG1L10 (Example 12) | 1:1 | ~0.03 | <0.05 | |
| 57 | PCC5 (Example 25) | PEG1L20 (Example 8) | 1:1 | | | ~0.06 |
| 58 | PCC6 (Example 26) | PEG1L20 (Example 8) | 1:1 | | | ~0.04 |
| 59 | PCC7 (Example 27) | PEG1L20 (Example 8) | 1:1 | | | ~0.05 |

$^a$Optical Density at 600 nm after 8 hours incubation with the corresponding microbe. A lower optical density indicates greater antimicrobial activity.
$^b$The control was phosphate buffered saline (PBS) solution.

Minimal Inhibitory Concentration (MIC).

General Procedure. *Staphylococcus aureus* (*S. aureus*), *Candida albicans* (*C. albicans*) and *Escherichia coli* (*E. coli*) were obtained from ATCC. The bacteria *S. aureus* and *E. coli* were grown in tryptic soy broth at 37° C. and the fungus *C. albicans* was cultured in yeast mould broth at 24° C. The MICs of single polymers were measured using a broth microdilution method. 100 microliters of polymer solution with various concentrations was placed into each well of 96-well plates. 100 microliters of microorganism solution at a concentration that gave an optical density reading of about 0.1 to 0.2 at 600 nm was added into each well. The cell cultures were then incubated for 8 hours and the optical density was monitored at 2 hour intervals. The minimum inhibitory concentration (MIC) in mg/L of polymer was taken The results show that the cationic triblock copolymers alone (Examples 61C and 62C) and the non-charged triblock copolymer alone (Example 63C) were not effective against Gram-negative *Escherichia coli* and Gram-positive *Staphylococcus aureus*, having a MIC greater than 25,000 mg/L.

Examples 64 to 66

The MIC was also determined for mixed complexes having a ratio of non-charged triblock copolymer to cationic triblock copolymers of 1:1 w/w. Table 19 lists the MIC data for Examples 64 to 66.

TABLE 19

| Example | Mixed Complexes Cationic Polymer:Non-charged Polymer (1:1 w/w) | MIC (mg/L) | |
|---|---|---|---|
| | | Gram-positive S. aureus | Gram-negative E. coli |
| 64 | PCC5:PEG1L10 | 500 | 5000 |
| 65 | PCC6:PEG1L10 | 1000 | 25000 |
| 66 | PCC7:PEG1L10 | 1000 | 25000 |

The data of Tables 18 and 19 indicate the mixed complexes show a synergistic effect in antimicrobial activity over the individual polymers, having a MIC less than or equal to 25000 mg/L. That is, the antimicrobial activity of the mixed complex is greater than the antimicrobial activity of the non-charged triblock copolymer alone and the cationic triblock copolymer alone when tested under otherwise identical conditions. The mixed complexes not only suppressed microbial growth, but also killed the microbes. The mixed complexes were more effective antimicrobial agents than the cationic polymer alone and the non-charged polymer alone.

Concentration Series

Examples 67C, and 68 to 70

Figure 7:
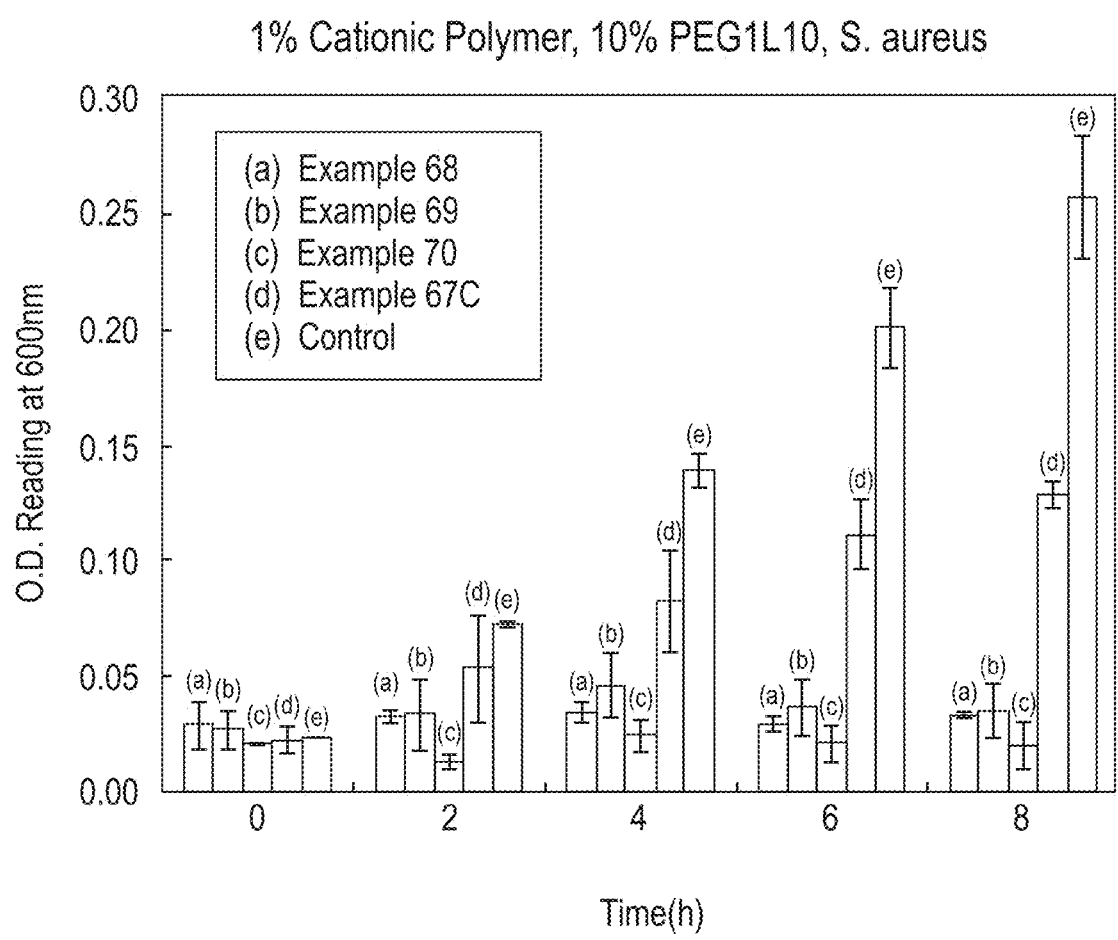
FIG. 7 is a bar graph comparing the antimicrobial activity of Example 67C (PEG1L10 alone), and Examples 68 to 70 (mixed complexes) against Gram-positive *Staphylococcus aureus* (*S. aureus*). The ratio of cationic triblock copolymer to non-charged triblock copolymer was 1:10 w/w.
Figure 8:
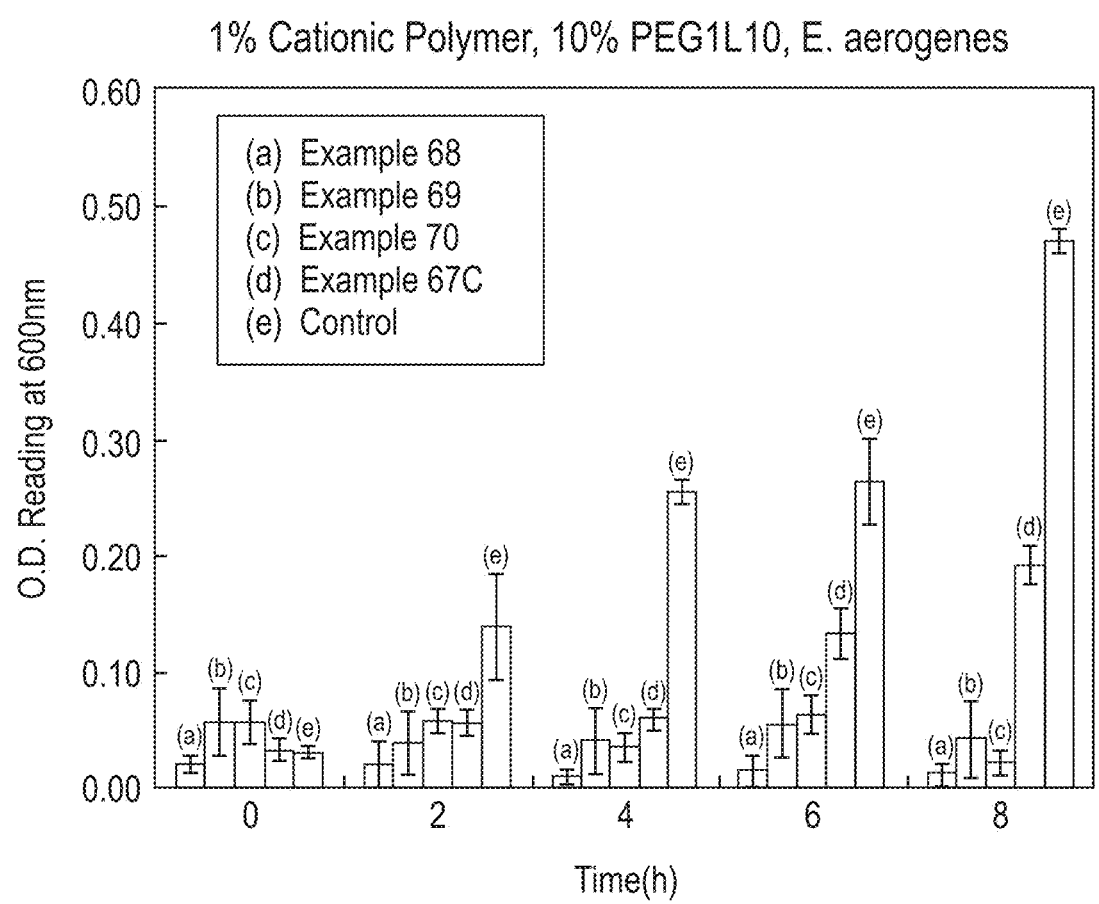
FIG. 8 is a bar graph comparing the antimicrobial activity of Example 67C (PEG1L10 alone), and Examples 68 to 70 (mixed complexes) against Gram-negative *Enterobacter aerogenes* (*E. aerogenes*). The ratio of cationic triblock copolymer to non-charged triblock copolymer was 1:10 w/w.
Figure 9:
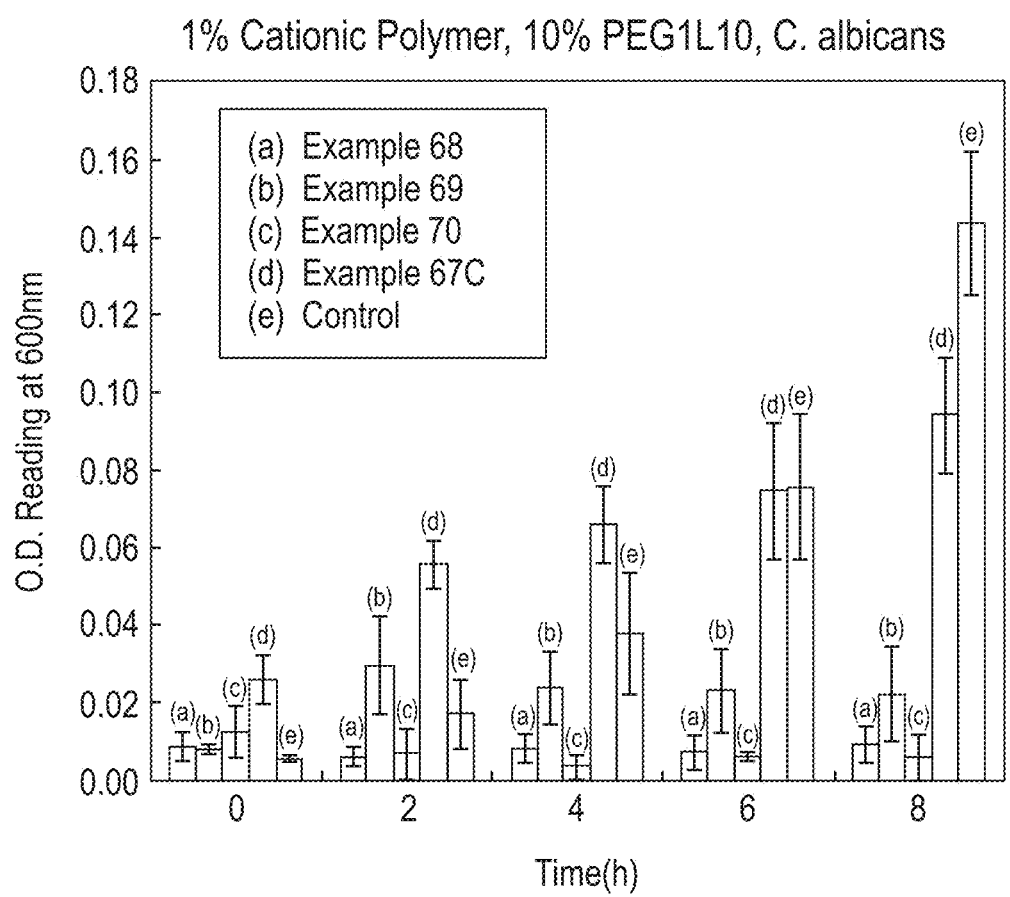
FIG. 9 is a bar graph comparing the antimicrobial activity of Example 67C (PEG1L10 alone), and Examples 68 to 70 (mixed complexes) against *Candida albicans* (*C. albicans*). The ratio of cationic triblock copolymer to non-charged triblock copolymer was 1:10 w/w.
Figure 10:
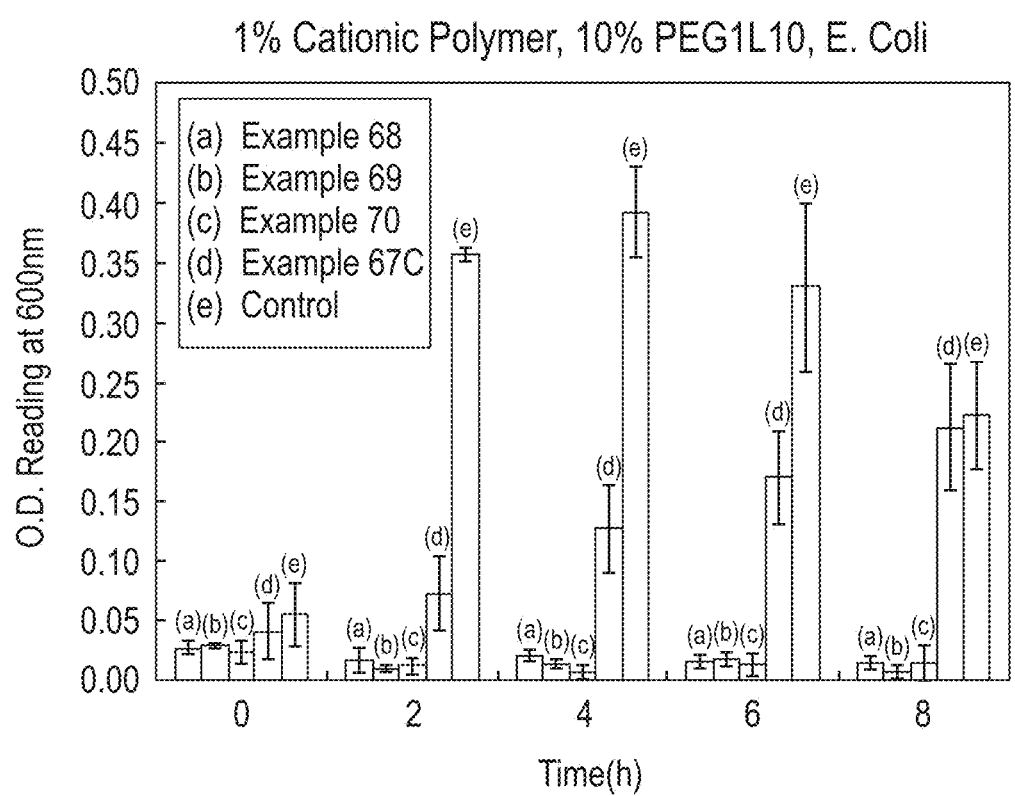
FIG. 10 is a bar graph comparing the antimicrobial activity of Example 67C (PEG1L10 alone), and Examples 68 to 70 (mixed complexes) against Gram-negative *Escherichia coli* (*E. coli*). The ratio of cationic triblock copolymer to non-charged triblock copolymer was 1:10 w/w.

1% w/v Cationic Polymer, 10% w/v PEG1L10. The above-described procedure used to test the antimicrobial activity of Examples 52C, 53C, and 54 to 59 was repeated using a mixed complex containing cationic polymer and non-charged polymer in a weight ratio of 1:10 w/w, respectively. The concentration of the cationic polymer was 1% w/v (10,000 mg/L) in the hydrogel. The concentration of the non-charged polymer was 10% w/v (100,000 mg/L) in the hydrogel. Thus, the concentration of the mixed complex was 11% w/v in the hydrogel. Four microbes were screened: S. aureus (FIG. 7), Enterobacter aerogenes (E. aerogenes) (FIG. 8), C. albicans (FIG. 9), and E. coli (FIG. 10). E. aerogenes is a Gram-negative rod-shaped bacterium. The compositions and antimicrobial activities are summarized in Table 20. A lower optical density (O.D.) at 600 nm indicates greater antimicrobial activity. At a cationic polymer concentration of 1% w/v (10,000 mg/L), the mixtures containing a mixed complex of the cationic polymer and PEG1L10 (Examples 68 to 70) killed each microbe efficiently. PEG1L10 alone (Example 67C) was not effective against E. coli, having an O.D. at 600 nm about the same as the PBS Control.

TABLE 20

| | | | | 1.0% w/v Cationic Polymer, 10% w/v PEG1L10 | | | |
|---|---|---|---|---|---|---|---|
| Example | Polymer 1 (Cationic) | Polymer 2 (Non-Charged) | Polymer 1:Polymer 2 ratio (w/w) | S. aureus. (O.D$^a$ @ 8 h) | E. aerogenes (O.D$^a$ @ 8 h) | E. coli (O.D$^a$ @ 8 h) | C. albicans (O.D$^a$ @ 8 h) |
| Control$^b$ | | | | ~0.25 | ~0.48 | ~0.22 | ~0.14 |
| 67C | | PEG1L10 (Example 12) | No Polymer 1 (10% w/v in Polymer 2) | >0.10 | ~0.20 | ~0.2 | ~0.09 |
| 68 | PCC5 (Example 25) | PEG1L10 (Example 12) | 1:10 | <0.05 | <0.05 | <0.05 | <0.02 |
| 69 | PCC6 (Example 26) | PEG1L10 (Example 12) | 1:10 | <0.05 | <0.05 | <0.05 | ~0.02 |
| 70 | PCC7 (Example 27) | PEG1L10 (Example 12) | 1:10 | <0.05 | <0.05 | <0.05 | <0.02 |

$^a$Optical Density at 600 nm after 8 hours incubation with the corresponding microbe.
$^b$50 microliters PBS buffer solution and microbe.

Examples 71C, 72 and 73

Figure 11:
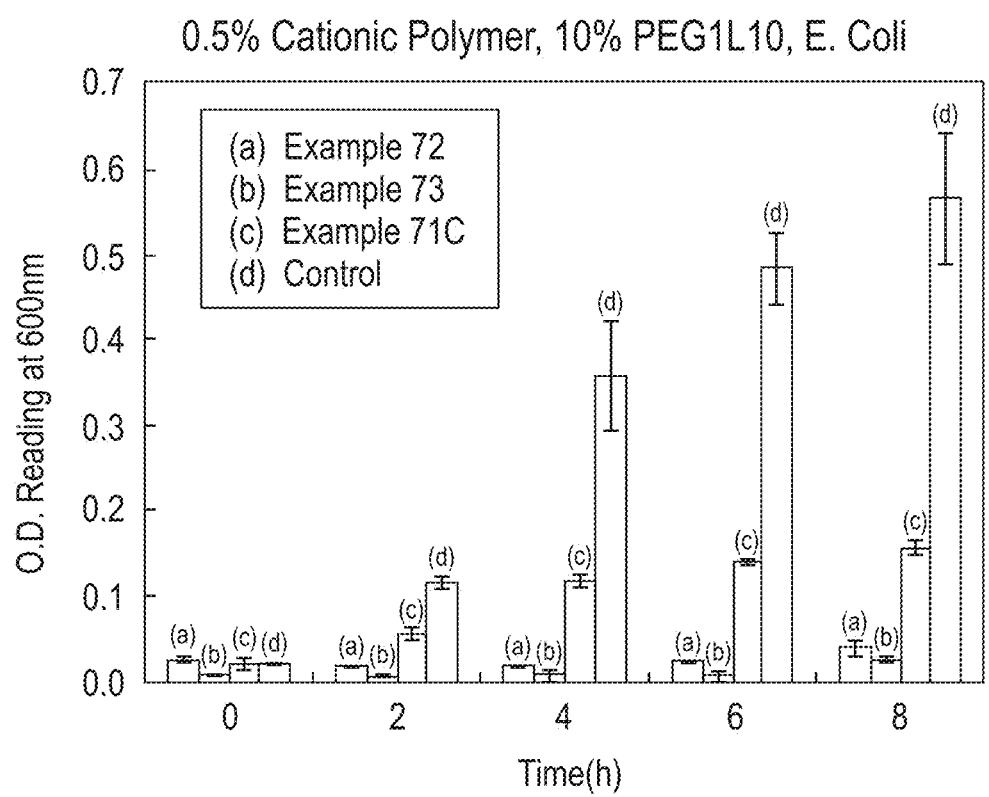
FIG. 11 is a bar graph comparing the antimicrobial activity of Example 71C (PEG1L10 alone), and Examples 72 to 73 (mixed complexes) against Gram-negative *Escherichia coli* (*E. coli*). The ratio of cationic triblock copolymer to non-charged triblock copolymer was 0.5:10 w/w.

0.5% w/v Cationic Polymer, 10% w/v PEG1L10. The above-described procedure used to test the antimicrobial activity of Examples 52C, 53C, and 54 to 59) was repeated using a mixed complex containing cationic polymer to non-charged polymer in a weight ratio of 0.5:10 w/w, respectively. The non-charged triblock copolymer concentration was 10% w/v (100,000 mg/L), and the cationic triblock copolymer concentration was 0.5% w/v (5,000 mg/L). Thus, the concentration of the mixed complex was 10.5% w/v in the hydrogel. The compositions were tested against E. coli (FIG. 11), and the antimicrobial activity is summarized in Table 21. In each case, the mixed complex (Examples 72 and 73) killed the microbe efficiently, and was more effective than PEG1L10. A lower optical density (O.D.) at 600 nm indicates greater antimicrobial activity.

TABLE 21

| | | 0.5% w/v Cationic Polymer, 10% w/v PEG1L10. | | |
|---|---|---|---|---|
| Example | Polymer 1 (Cationic) | Polymer 2 (Non-Charged) | Polymer 1:Polymer 2 ratio (w/w) | E. coli (O.D$^a$ @ 8 h) |
| Control$^b$ | | | | ~0.56 |
| 71C | | PEG1L10 (Example 12) | No Polymer 1 (10% w/v in Polymer 2) | ~0.15 |

TABLE 21-continued 0.5% w/v Cationic Polymer, 10% w/v PEG1L10.

| Example | Polymer 1 (Cationic) | Polymer 2 (Non-Charged) | Polymer 1:Polymer 2 ratio (w/w) | E. coli (O.D[a] @ 8 h) |
|---|---|---|---|---|
| 72 | PCC6 (Example 26) | PEG1L10 (Example 12) | 0.5:10 | ~0.05 |
| 73 | PCC7 (Example 27) | PEG1L10 (Example 12) | 0.5:10 | <0.05 |

[a]Optical Density at 600 nm after 8 hours incubation with the corresponding microbe.
[b]50 microliters PBS buffer solution and microbe.

Examples 74C, 75 and 76

Figure 12:
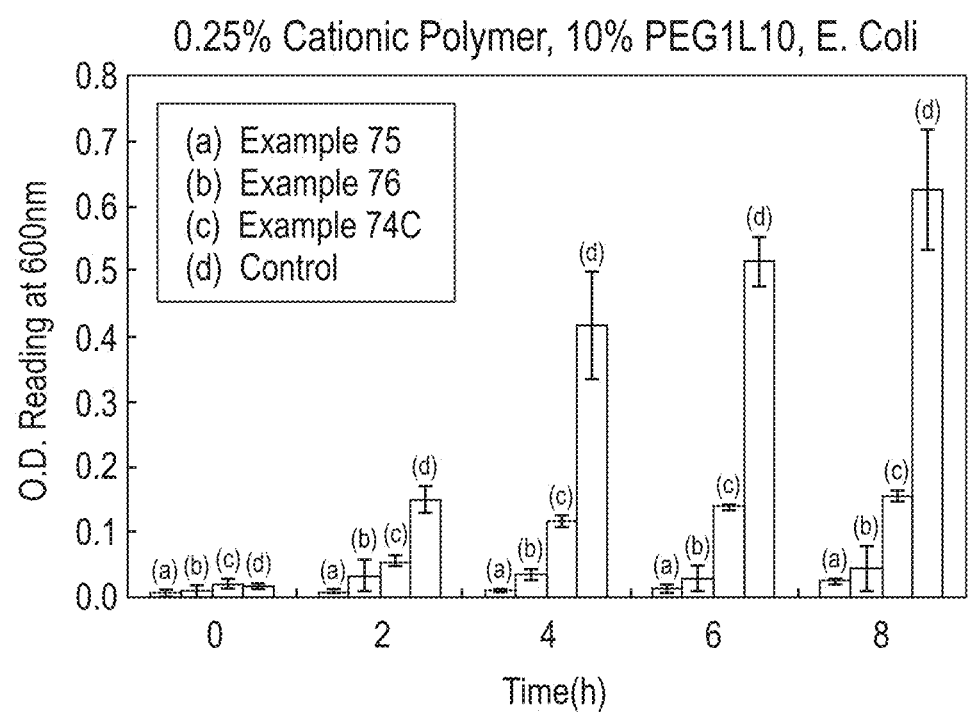
FIG. 12 is a bar graph comparing the antimicrobial activity of Example 74C (PEG1L10 alone), and Examples 75 to 76 (mixed complexes) against Gram-negative *Escherichia coli* (*E. coli*). The ratio of cationic triblock copolymer to non-charged triblock copolymer was 0.25:10 w/w.

0.25% w/v Cationic Polymer, 10% w/v PEG1L10. The above-described procedure used to test the antimicrobial activity of Examples 52C, 53C, and 54 to 59) was repeated using a mixed complex containing cationic triblock copolymer and non-charged triblock copolymer in a weight ratio of 0.25:10 w/w, respectively. The non-charged triblock copolymer concentration was 10% w/v (100,000 mg/L), and the cationic triblock copolymer concentration was 0.25% w/v (2,500 mg/L) in the hydrogel, making the concentration of the mixed complex 10.25% w/v in the hydrogel. The compositions were tested against E. coli (FIG. 12), and the antimicrobial activity is summarized in Table 22. In each case, the mixed complex (Examples 75 and 76) killed the microbe efficiently. A lower optical density (O.D.) at 600 nm indicates greater antimicrobial activity.

TABLE 22

0.25% w/v Cationic Polymer, 10% w/v PEG1L10.

| Example | Polymer 1 (Cationic) | Polymer 2 (Non-Charged) | Polymer 1:Polymer 2 ratio (w/w) | E. coli (O.D[a] @ 8 h) |
|---|---|---|---|---|
| Control[b] | | | | ~0.62 |
| 74C | | PEG1L10 (Example 12) | No Polymer 1 (10% w/v in Polymer 2) | ~0.15 |
| 75 | PCC6 (Example 26) | PEG1L10 (Example 12) | 0.25:10 | <0.05 |
| 76 | PCC7 (Example 27) | PEG1L10 (Example 12) | 0.25:10 | ~0.05 |

[a]Optical Density at 600 nm after 8 hours incubation with the corresponding microbe.
[b]50 microliters PBS buffer solution and microbe.

Figures 13A, 13B, 13C:
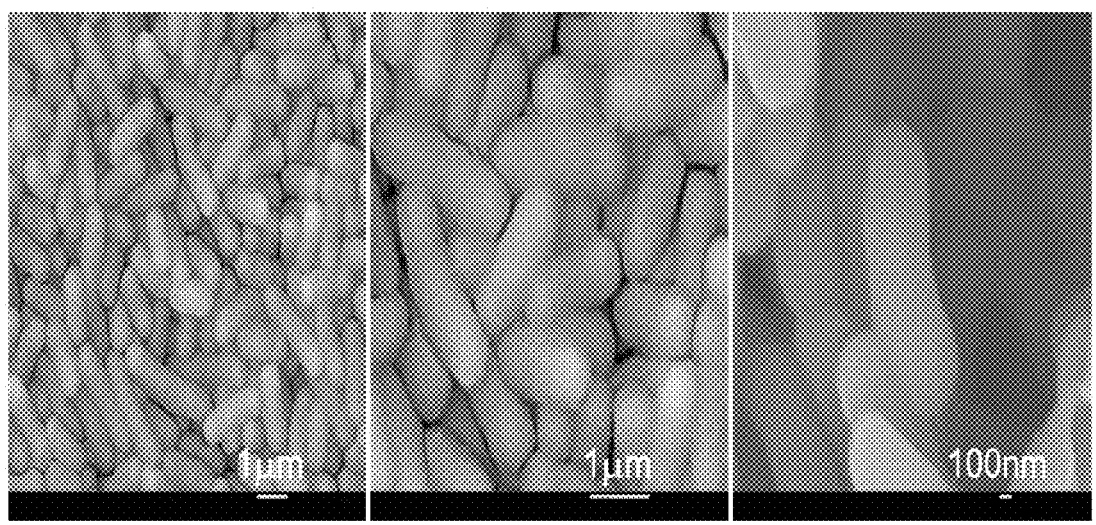
FIGS. 13A to 13C are SEMs of *E. coli* cells at magnifications 10 k, 20 k, and 40 k, respectively, after incubation 2 hours in control solution of phosphate buffer saline (PBS). No damage to the cell wall was seen.
Figure 14A:
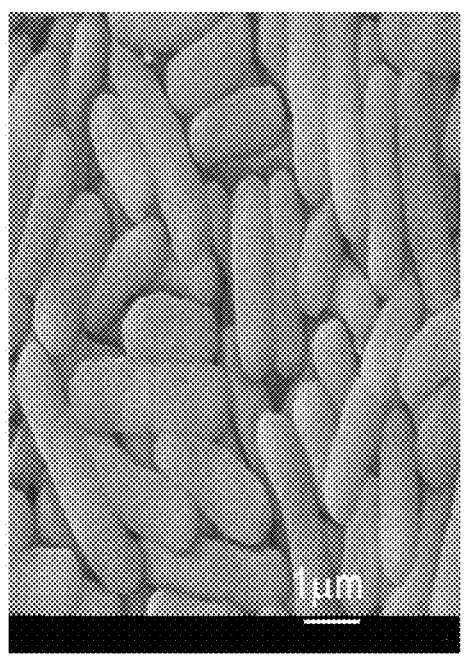
FIGS. 14A to 14B are SEMs of *E. coli* cells at magnifications 15 k and 35 k, respectively, after incubation 2 hours with a hydrogel prepared from non-charged triblock copolymer PEG1L10 alone (Example 74C). No damage was observed to the cell wall.
Figure 14B:
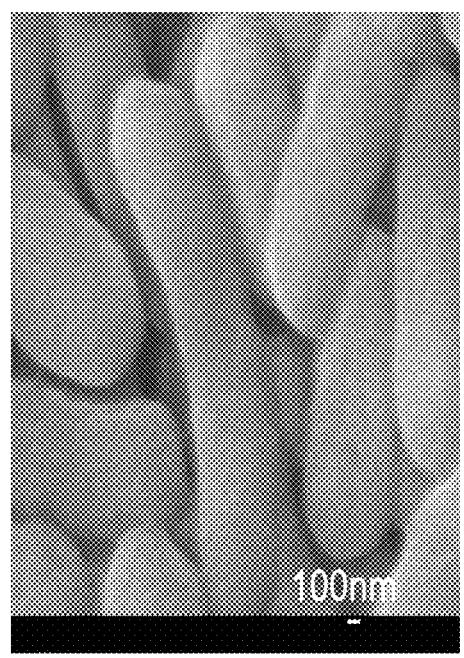
Figures 15A, 15B, 15C:
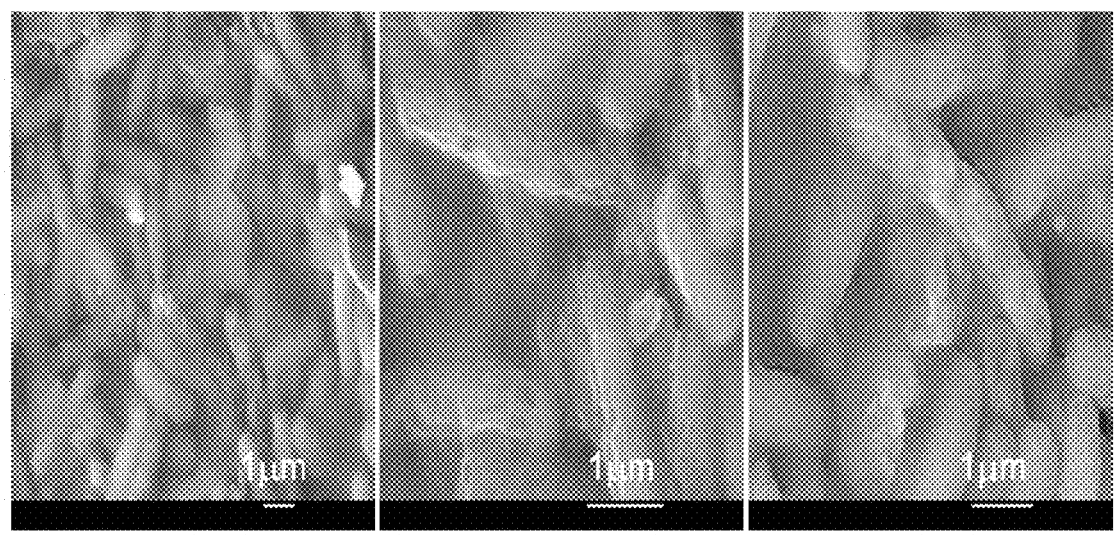
FIGS. 15A to 15C are SEMs of *E. coli* cells at magnifications 15 k, 25 k, and 20 k, respectively, after incubation 2 hours with a hydrogel of a mixed complex prepared from charged triblock copolymer PCC5 and non-charged triblock copolymer PEG1L10 (Example 68). Damage to the cell wall/membrane can be seen.

FIGS. 13A to 13C are SEMs of E. coli cells at magnifications 10 k, 20 k, and 40 k, respectively, after incubation 2 hours in PBS control solution. No damage to the cell wall was seen. FIGS. 14A to 14B are SEMs of E. coli cells at magnifications 15 k and 35 k, respectively, after incubation 2 hours with a hydrogel formed by PEG1L10 alone (Example 74C). No damage was observed to the cell wall. FIGS. 15A to 15C are SEMs of E. coli cells at magnifications 15 k, 25 k, and 20 k, respectively, after incubation 2 hours with a hydrogel formed by PCC5 and PEG1L10 (Example 68). Damage to the cell wall/membrane can be seen.

Summarizing the above examples, effective antimicrobial activity was obtained using mixed complexes containing cationic triblock copolymer and non-charged triblock copolymer in a ratio of 0.25:10 to 1:1 w/w, respectively. Effective antimicrobial activity was obtained using mixed complexes that contained cationic triblock copolymer at a concentration of about 0.25% w/v to about 5.0% w/v, and non-charged triblock copolymer at a concentration of about 5.0% w/v to about 10% w/v. At these non-charged triblock copolymer concentrations, the mixed complexes also formed hydrogels. The cationic triblock copolymers alone and the non-charged triblock copolymers alone were not as effective antimicrobial agents against Gram-positive and Gram-negative microbes compared to the mixed complexes, even when the individual non-charged triblock copolymer formed a hydrogel. The minimum inhibitory concentration (MIC) of a mixed complex prepared using a 1:1 weight ratio of the cationic triblock copolymer and non-charged triblock copolymer was about 500 mg/L to less than or equal to 25000 mg/L, or about 0.05% w/v to less than or equal to 2.5% w/v for Gram-positive and Gram-negative microbes.

DNA Binding

Examples 77 and 78

The following general procedure can be used for preparing a hydrogel/DNA complex. Cationic triblock copolymer/DNA complexes were prepared at N/P ratios (molar ratio of N content in the polymer to the DNA phosphorus content) in the range of 0 to 15 by dripping equal volume of DNA solution into the cationic triblock copolymer solution. Example 77 utilized PCC5 (Example 25) and Example 78 utilized PCC6 (Example 26). After equilibration of the mixture for 30 minutes at room temperature, the complexes were electrophoresed on 0.7% agarose gel (stained with 5 microliters of 10 mg/mL ethidium bromide per 50 mL of agarose solution) in 0.5×TBE buffer at 80V for 50 min. The gel was then analyzed under an UV illuminator (Chemi Genius, Evolve, Singapore) to reveal the relative position of DNA in the complexes to the naked DNA.

Figure 16:
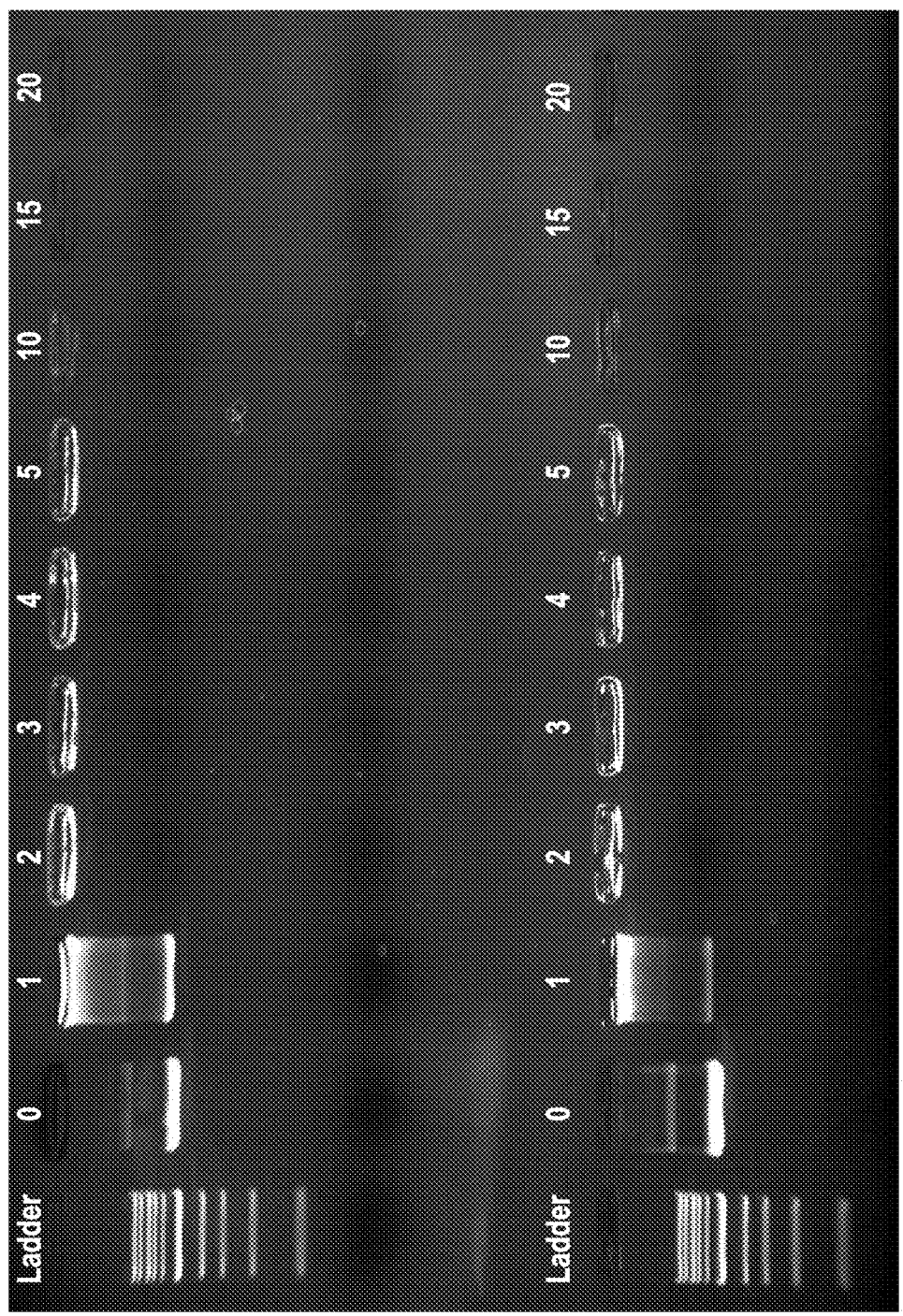
FIG. 16 is a photograph showing the electrophoretic mobility of DNA in Example 77 using cationic triblock copolymers PCC5 (Example 25) and in Example 78 using PCC6 (Example 26).

FIG. 16 is a photograph showing the electrophoretic mobility of DNA in Example 77 using cationic triblock copolymer PCC5, and Example 78 using PCC6. The polymers bind DNA efficiently. The complete retardation of DNA mobility was achieved at N/P 2.

Cationic Star Polymer

Example 79

Preparation of cationic star polymer CSP1. The following preparation demonstrates the cationic block copolymer can be a highly branched structure prepared by ring opening polymerization using a cyclic initiator comprising one or more ROP initiator groups. This example further demonstrates the initiator can also be stereospecific. In this instance, the ROP initiator is beta cyclodextrin (b-CD):

87 b-CD

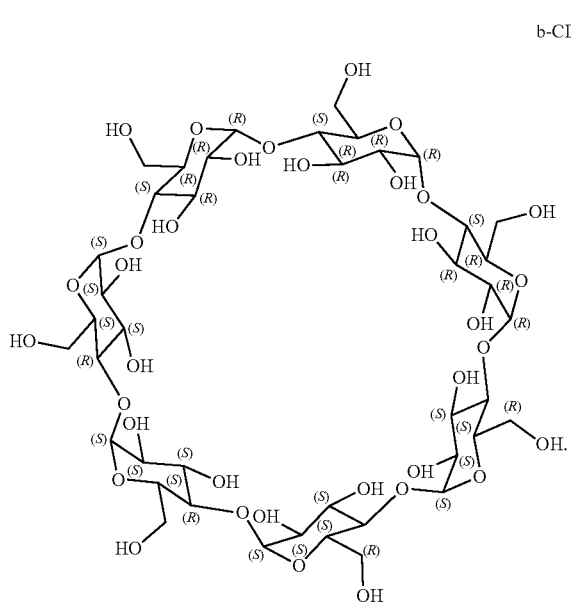

b-CD has 21 hydroxy groups independently capable of initiating a ring opening polymerization. In this instance, the initiator is also stereospecific. The R,S symmetry of each tetravalent carbon center of b-CD is labeled in the above structure. Using the above described methods of making a cationic triblock copolymer, a first ring opening polymerization of L-lactide was performed using b-CD as the initiator. The resulting first living star polymer has 21 poly(L-lactide) arms, and each arm has an alcohol initiator group on the end unit. The first living star polymer was used to initiate a second ring opening polymerization of cyclic carbonate monomer MTCOPrCl. The resulting living second star polymer comprises 21 polymer arms, and each polymer arm comprises an inner hydrophobic poly(L-lactide) block and a peripheral polycarbonate block having an alcohol initiator group on the end unit. The polycarbonate repeat unit has a side chain moiety comprising an active chloride group. The living second star polymer was endcapped using acetic anhydride. The peripheral polycarbonate block was then quaternized using trimethylamine to form cationic star polymer CSP1 having the following structure:

CSP1

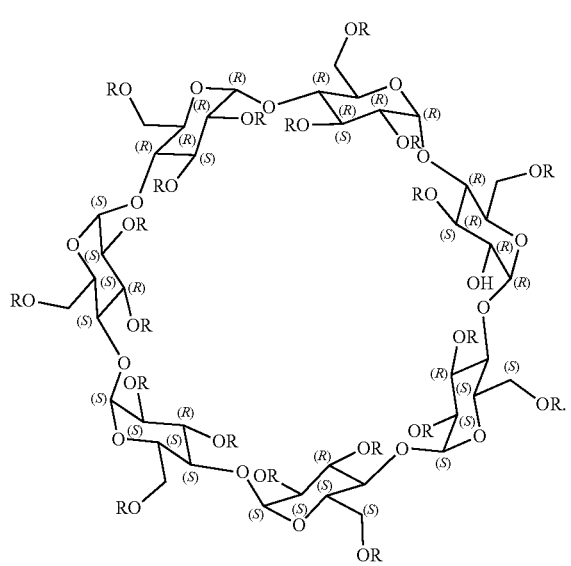

88

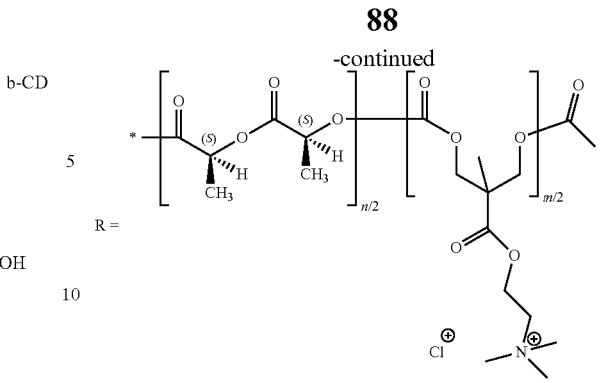

The starred bond represents the attachment point of the group R to the oxygen of the cyclodextrin moiety. Each polymer arm CSP1 has a peripheral cationic polycarbonate block and an inner hydrophobic poly(L-lactide) block linked to the cyclodextrin moiety. CSP1 has a number average molecular weight (Mn) of 68 kDa, and a PDI of 1.06.

Antimicrobial Activity of Hydrogels of CSP1 and PEG1L10

Examples 80 to 83, 84C and 85C

The following procedure was used to prepare four hydrogels containing CSP1 and PEG1L10. PEG1L10 and CSP1 were separately dissolved in deionized water without the use of an organic solvent. Hydrogel was then formed by mixing the two polymer solutions. Four hydrogel samples were prepared having a CSP1 to PEG1L10 weight ratio of 0.25:1 (Example 80), 0.5:1 (Example 81), 0.75:1 (Example 82) and 1:1 (Example 83). The PEG1L10 concentration was 5% w/v in the four hydrogels. The CSP1 concentration was 1.25% w/v, 2.5% w/v, 3.75% w/v, and 5% w/v, respectively, in the four hydrogels. The total polymer concentration was 6.25% w/v, 7.5% w/v, 8.75% w/v, and 10% w/v, respectively, in the four hydrogels. Hydrogels containing PEG1L10 alone at 5% w/v (Example 84C) and 10% w/v (Example 85C) were also prepared as controls for the following antimicrobial tests. The hydrogels were equilibrated at 37° C. for 1 hour. Example 84C (5% w/v PEG1L10 alone) and Example 85C (10% w/v PEG1L10 alone) appeared cloudy. The hydrogel formed by Example 84C (5% w/v PEG1L10) could still flow when a test tube containing the hydrogel was inverted. The hydrogel formed by Example 85C (10% w/v PEG1L10) did not flow when a test tube containing the hydrogel was inverted. The hydrogels of Examples 80 to 83 were clear rather than cloudy. The hydrogels of Examples 80 to 83 did not flow when the individual test tubes containing the hydrogels were inverted.

Figure 17:
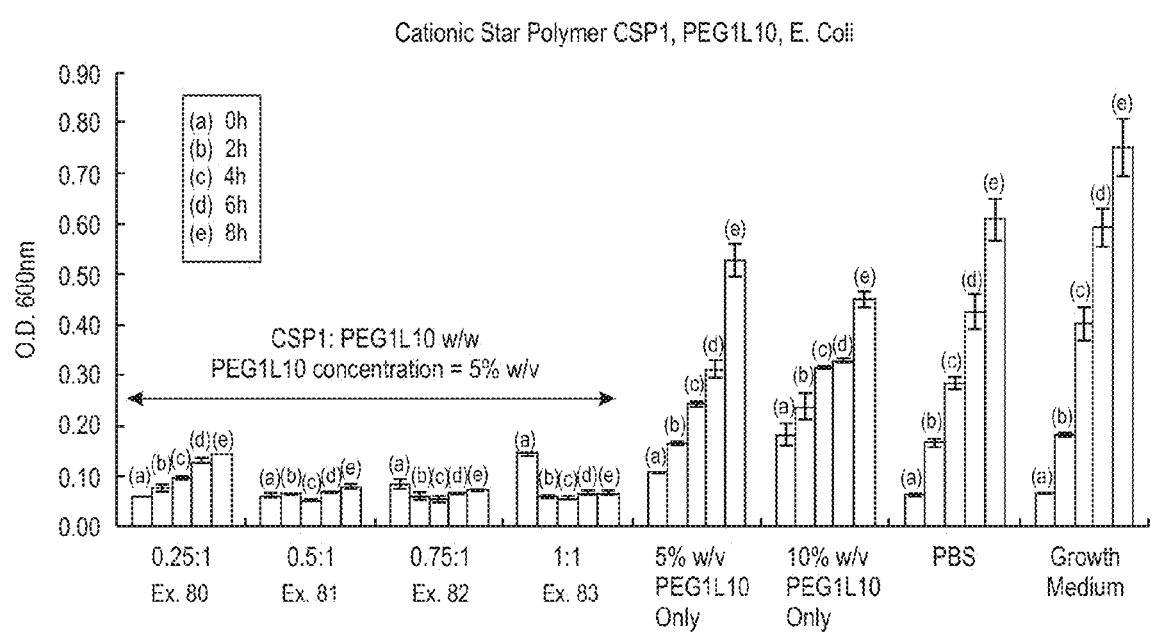
FIG. 17 is a bar graph showing the antimicrobial activity of Examples 80 to 83 (hydrogels formed with cationic star polymer CSP1 and PEG1L10 at several CSP1:PEG1L10 weight ratios and at fixed PEG1L10 concentration of 5% w/v in each sample) against Gram-negative *Escherichia coli* (*E. coli*). Control samples include Example 84C (PEG1L10 alone, 5% w/v), Example 85C (PEG1L10 alone, 10% w/v), PBS, and Growth Medium.

30 microliters of microorganism solution, at a concentration that gave an optical density reading of about 0.1 to 0.2 at 600 nm, was then added into each hydrogel (Examples 80 to 83, 84C and 85C). PBS (pH 7.4) solution and bacterial growth medium containing bacterial cells were also used as negative controls. The cell cultures were then incubated for 8 hours and the optical density was monitored at 2 hour intervals. The results are shown in the bar graph of FIG. 17. A lower optical density (O.D.) at 600 nm indicates greater antimicrobial activity. No E. Coli growth was observed for Examples 81 to 83 (CSP1:PEG1L10 weight ratios of 0.5:1 to 1:1, respectively) after 8 hours. Slight E. coli growth was observed with Example 80 after 8 hours, although much less than the E. coli growth observed with the two PEG1L10 samples (Examples 84C and 85C) and the PBS and Growth Medium controls after 8 hours. The results are summarized in Table 23.

TABLE 23

CSP1, PEG1L10, various weight ratios.

| Example | Polymer 1 (Cationic) | Polymer 2 (Non-Charged) | Polymer 1:Polymer 2 weight ratio (w/w) | E. coli (O.D[a] @ 8 h) |
|---|---|---|---|---|
| Growth Medium | | | | ~.75 |
| PBS[b] | | | | ~0.60 |
| 84C | | PEG1L10 (Example 12) | No Polymer 1 (5% w/v in Polymer 2) | ~0.54 |
| 85C | | PEG1L10 (Example 12) | No Polymer 1 (10% w/v in Polymer 2) | ~0.45 |
| 80 | CSP1 (Example 80) | PEG1L10 (Example 12) | 0.25:1 | ~0.16 |
| 81 | CSP1 (Example 80) | PEG1L10 (Example 12) | 0.5:1 | <0.10 |
| 82 | CSP1 (Example 80) | PEG1L10 (Example 12) | 0.75:1 | <0.10 |
| 83 | CSP1 (Example 80) | PEG1L10 (Example 12) | 1:1 | <0.10 |

[a]Optical Density at 600 nm after 8 hours incubation with the corresponding microbe.
[b]50 microliters PBS buffer solution and microbe.

The above examples demonstrate that a mixture of a cationic triblock copolymer and a non-charged triblock copolymer can self-assemble in aqueous solution to form a mixed complex in the form of a micelle and/or a hydrogel that are superior antimicrobial agents compared to the non-charged triblock copolymer alone and the cationic triblock copolymer alone when tested under otherwise identical conditions. The cationic triblock copolymers effectively bind DNA, indicating the mixed complexes are good candidates for forming loaded complexes with anionic materials, including genes and drugs. Similarly, a mixture of a non-charged triblock copolymer and a cationic star polymer, which comprises polymer arms that include a stereoregular hydrophobic block and a cationic hydrophilic block, can self-assemble in aqueous solution to form a mixed complex in the form of a micelle and/or a hydrogel having effective antimicrobial activity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. When a range is used to express a possible value using two numerical limits X and Y (e.g., a concentration of X ppm to Y ppm), unless otherwise stated the value can be X, Y, or any number between X and Y.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and their practical application, and to enable others of ordinary skill in the art to understand the invention.

What is claimed is:

1. A composition of matter, comprising:
    a cationic triblock copolymer having an ABA block structure, wherein a block A is a hydrophobic peripheral block comprising a first polyester chain segment, and a block B is a hydrophilic cationic core block comprising a polycarbonate chain segment, the polycarbonate comprising a repeat unit comprising a cationic side chain moiety, the cationic side chain moiety comprising a quaternary amine group; and
    a non-charged triblock copolymer having a FEF block structure, wherein block E is a hydrophilic non-charged core block comprising a poly(alkylene oxide) chain segment, and block F is a peripheral hydrophobic block comprising a second polyester chain segment;
    wherein i) the non-charged triblock copolymer and the cationic triblock copolymer are amphiphilic and biocompatible, ii) the non-charged triblock copolymer and the cationic triblock copolymer form a mixed complex by non-covalent interactions in water, and iii) the mixed complex is a more effective antimicrobial agent against at least a Gram-negative microbe compared to the cationic triblock copolymer alone and the non-charged triblock copolymer alone when tested using otherwise identical conditions.

2. The composition of claim 1, wherein the cationic triblock copolymer and the non-charged triblock copolymer are present in the composition in a weight ratio of about 0.25:10 w/w to about 3:2 w/w.

3. The composition of claim 1, wherein block A, block B, block F, and optionally block E are enzymatically biodegradable.

4. The composition of claim 1, wherein the composition comprises water and the composition is a hydrogel.

5. The composition of claim 1, wherein block A comprises a first stereospecific repeat unit, and the block F comprises a second stereospecific repeat unit.

6. The composition of claim 5, wherein the first stereospecific repeat unit is a non-superposable mirror image of the second stereospecific repeat unit.

7. The composition of claim 1, wherein block A comprises a poly(D-lactide) chain segment and the block F comprises a poly(L-lactide) chain segment.

8. The composition of claim 1, wherein the block A comprises a poly(L-lactide) chain segment and the block F comprises a poly(D-lactide) chain segment.

9. The composition of claim 1, wherein the poly(alkylene oxide) chain segment is a poly(ethylene oxide) chain segment.

10. The composition of claim 1, wherein the composition is toxic to a Gram-negative microbe and to a Gram-positive microbe selected from the group consisting of bacteria, fungi, yeasts, and combinations thereof.

11. The composition of claim 1, wherein the cationic triblock copolymer alone and the non-charged triblock copolymer alone are individually not effective antimicrobial agents against the Gram-negative microbe.

12. The composition of claim 1, wherein the Gram-negative microbe is *Escherichia coli*.

13. A loaded complex comprising i) the composition of claim 1 and ii) a drug and/or a gene.

14. A method, comprising contacting a microbe with the composition of claim 1, thereby killing the microbe.

15. A method, comprising:
    forming an aqueous mixture of the composition of claim 1, the aqueous mixture being an effective antimicrobial agent against at least a Gram-negative microbe.

16. The method of claim 15, wherein at a temperature of 18° C. to 28° C. and a pH of 4.5 to 8.0, the aqueous mixture is a liquid micelle solution.

17. The method of claim 15, wherein at a temperature of 18° C. to 28° C. and a pH of 4.5 to 8.0, the aqueous mixture is a hydrogel.

18. The method of claim 15, further comprising heating the aqueous mixture to a temperature of 32° C. to 40° C., the aqueous mixture having a pH of 4.5 to 8.0, thereby forming a hydrogel.

19. The method of claim 15, wherein the aqueous mixture is a hydrogel, and the hydrogel comprises a rod-like structure comprising the cationic triblock copolymer and the non-charged triblock copolymer.

20. The method of claim 19, wherein the rod-like structure has a diameter of about 100 nm to 500 nm and a length of about 0.5 micrometer to about 50 micrometers.

21. The method of claim 15, further comprising contacting a microbe with the aqueous mixture, thereby killing the microbe.

22. The method of claim 15, further comprising contacting an animal tissue with the aqueous mixture.

23. The method of claim 15, further comprising contacting a surface of an article with the aqueous mixture.

24. A method, comprising:
    forming an aqueous first mixture of a cationic triblock copolymer having an ABA block structure, wherein a block A is a peripheral hydrophobic block comprising a first polyester chain segment, and a block B is a hydrophilic cationic core block comprising a polycarbonate chain segment, the polycarbonate comprising a repeat unit comprising a cationic side chain moiety, the cationic side chain moiety comprising a quaternary amine group;
    forming an aqueous second mixture of a non-charged triblock copolymer having a FEF block structure, wherein a block E is a hydrophilic non-charged core block comprising a poly(alkylene oxide) chain segment, and a block F is a peripheral hydrophobic block, comprising a second polyester chain segment; and
    combining the first mixture and the second mixture, thereby forming a third mixture comprising a mixed complex of the cationic triblock copolymer and the non-charged triblock copolymer bound by non-covalent interactions;
    wherein i) the non-charged triblock copolymer and the cationic triblock copolymer are amphiphilic and biocompatible, and ii) the mixed complex is a more effective antimicrobial agent against at least a Gram-negative microbe compared to the cationic triblock copolymer alone and the non-charged triblock copolymer alone when tested using otherwise identical conditions.

25. The method of claim 24, wherein the cationic triblock copolymer and the non-charged triblock copolymer are present in the third mixture in a weight ratio of about 0.25:10 w/w to about 3:2 w/w.

26. The method of claim 24, wherein the cationic triblock copolymer alone and the non-charged triblock copolymer alone are individually not effective antimicrobial agents against the Gram-negative microbe when tested under otherwise identical conditions.

27. The method of claim 24, wherein heating the third mixture to 32° C. to 40° C. produces a hydrogel.

28. The method of claim 24, wherein removing any organic solvent at ambient temperature from the third mixture produces a hydrogel.

29. The method of claim 24, wherein block A comprises a first stereospecific repeat unit, and the block F comprises a second stereospecific repeat unit.

30. The method of claim 24, wherein the cationic triblock copolymer and/or the non-charged triblock copolymer are formed by an organocatalyzed ring opening polymerization of one or more cyclic carbonyl monomers.

31. The method of claim 24, wherein block A, B, F, and optionally E are enzymatically biodegradable.

32. An article comprising a medical device in contact with the composition of claim 1.

33. The article of claim 32, wherein the medical device includes at least one of the following: a swab, a catheter, a suture, a stent, a bedpan, a glove, a facial mask, an absorbent pad, an absorbent garment, an internal absorbant device, and an insertable mechanical device.

34. A composition of matter, comprising:
    a cationic triblock polymer comprising a polycarbonate chain fragment, the polycarbonate chain fragment comprising a repeat unit comprising a side chain moiety containing a quaternary amine group; and
    a non-charged triblock polymer comprising a polyester chain segment and a poly(alkylene oxide) chain segment;
    wherein i) the cationic triblock polymer and the non-charged triblock polymer are amphiphilic and biocompatible, ii) the cationic triblock polymer and the non-charged triblock polymer form a mixed complex by non-covalent interactions in water, and iii) the mixed complex is a more effective antimicrobial agent against at least a Gram-negative microbe compared to the cationic triblock polymer and the non-charged triblock polymer alone when tested using otherwise identical conditions.

35. The composition of claim 34, wherein the composition comprises water.

36. The composition of claim 35, wherein the composition is a hydrogel.

37. The composition of claim 34, wherein the cationic triblock polymer comprises a first stereospecific repeat unit, and the non-charged triblock polymer comprises a second stereospecific repeat unit.

38. The composition of claim 34, wherein the cationic triblock polymer and the non-charged triblock polymer alone are individually not effective antimicrobial agents against the Gram-negative microbe when tested under otherwise identical conditions.

39. The composition of claim 34, wherein the cationic triblock polymer is enzymatically biodegradable, and the non-charged triblock polymer is substantially or wholly enzymatically biodegradable.

40. The composition of claim 34, wherein the cationic triblock polymer is a star polymer comprising three or more polymer arms.

41. A method, comprising contacting a microbe with the composition of claim 34, thereby killing the microbe.

42. A loaded complex comprising i) the composition of claim 34 and ii) a drug and/or a gene.

43. A method, comprising:
    forming an aqueous mixture of the composition of claim 34 wherein the aqueous mixture is an effective antimicrobial agent against at least a Gram-negative microbe.

44. A method, comprising:
    forming an aqueous first mixture containing a cationic triblock polymer comprising a polycarbonate chain fragment, the polycarbonate chain fragment comprising a repeat unit comprising a side chain quaternary amine group;

forming an aqueous second mixture containing a non-charged triblock polymer comprising a polyester chain segment and a poly(alkylene oxide) chain segment; and combining the first mixture and the second mixture, thereby forming a third mixture comprising a mixed complex of the cationic triblock polymer and the non-charged triblock polymer bound by non-covalent interactions;

wherein i) the cationic triblock polymer and the non-charged triblock polymer are amphiphilic and biocompatible, and ii) the mixed complex is a more effective antimicrobial agent against at least a Gram-negative microbe compared to the cationic triblock polymer alone and the non-charged triblock polymer alone when tested under otherwise identical conditions.

* * * * *